US010682442B2

(12) United States Patent
Puleo et al.

(10) Patent No.: US 10,682,442 B2
(45) Date of Patent: Jun. 16, 2020

(54) SMALL MOLECULE DRUG RELEASE FROM IN SITU FORMING DEGRADABLE SCAFFOLDS INCORPORATING HYDROGELS AND BIOCERAMIC MICROPARTICLES

(71) Applicant: University of Kentucky Research Foundation, Lexington, KY (US)

(72) Inventors: David Puleo, Lexington, KY (US);
Todd Milbrandt, Lexington, KY (US);
James Zach Hilt, Lexington, KY (US);
Paul Fisher, Lexington, KY (US);
Vishwas Talwalkar, Lexington, KY (US)

(73) Assignee: UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 0 days.

(21) Appl. No.: 14/678,479

(22) Filed: Apr. 3, 2015

(65) Prior Publication Data
US 2015/0290361 A1 Oct. 15, 2015

Related U.S. Application Data

(60) Provisional application No. 61/975,139, filed on Apr. 4, 2014.

(51) Int. Cl.
*A61L 27/54* (2006.01)
*A61L 27/52* (2006.01)
*A61L 27/18* (2006.01)
*A61K 31/65* (2006.01)
*A61K 31/366* (2006.01)
*A61K 47/36* (2006.01)
*A61L 27/12* (2006.01)
*A61K 9/00* (2006.01)
*A61K 31/663* (2006.01)

(52) U.S. Cl.
CPC ............ *A61L 27/54* (2013.01); *A61K 9/0024* (2013.01); *A61K 31/366* (2013.01); *A61K 31/65* (2013.01); *A61K 31/663* (2013.01); *A61K 47/36* (2013.01); *A61L 27/12* (2013.01); *A61L 27/18* (2013.01); *A61L 27/52* (2013.01); *A61L 2300/602* (2013.01); *A61L 2400/06* (2013.01); *A61L 2430/02* (2013.01)

(58) Field of Classification Search
USPC ........................................................ 424/426
See application file for complete search history.

(56) References Cited

U.S. PATENT DOCUMENTS

| | | | |
|---|---|---|---|
| 4,818,542 | A | 4/1989 | DeLuca et al. |
| 5,656,298 | A | 8/1997 | Kitchell et al. |
| 6,743,446 | B2 | 6/2004 | Schwendeman et al. |
| 6,863,899 | B2 | 3/2005 | Koblish et al. |
| 7,022,522 | B2 | 4/2006 | Guan et al. |
| 8,163,030 | B2 | 4/2012 | Maspero et al. |
| 8,173,148 | B2 | 5/2012 | Dadey et al. |
| 8,337,816 | B2 | 12/2012 | Brown et al. |
| 8,394,488 | B2 | 3/2013 | Dave et al. |
| 8,546,521 | B2 | 10/2013 | Ramstack et al. |
| 8,663,677 | B2 | 3/2014 | Fu et al. |
| 2004/0105878 | A1 | 6/2004 | Schwendeman et al. |
| 2006/0018942 | A1 | 1/2006 | Rowe et al. |
| 2009/0149873 | A1 | 6/2009 | Zhou et al. |
| 2010/0041770 | A1 | 2/2010 | Liu et al. |
| 2010/0047318 | A1 | 2/2010 | Kumar |
| 2012/0107383 | A1 | 5/2012 | McKay |
| 2012/0195952 | A1 | 8/2012 | King |
| 2013/0071326 | A1 | 3/2013 | Martinez et al. |
| 2013/0078312 | A1 | 3/2013 | Kunjachan |
| 2013/0295186 | A1 | 11/2013 | Loo et al. |
| 2013/0323294 | A1 | 12/2013 | Farrar et al. |

FOREIGN PATENT DOCUMENTS

| | | |
|---|---|---|
| CN | 102114271 A | 7/2011 |
| JP | 2008106024 A | 5/2008 |
| WO | 2010036919 A1 | 4/2010 |
| WO | 2013014677 A1 | 1/2013 |

OTHER PUBLICATIONS

Schloegl (European Journal of Pharmaceutics and Biopharmaceutics 82 (2012) 554-562).*
Park (Med Oral Patol Oral Cir Bucal. Sep. 1, 2009;14 (9):e485-8).*
Hawkins (Acta Biomaterialia 7 (2011) 1956-1964).*
Sigma (http://www.sigmaaldrich.com/materials-science/polymer-science/resomer.html, accessed Jun. 26, 2016).*
Fedorovich (Biomed Mater Res Part A 2012:100A:2342-2347).*
Tachaboonyakiat (Polymer Journal 33, 177-181 (2001)).*
Liang (ChemPhysChem 2007, 8, 2367-2372).*
Orellana (Journal of the mechanical behavior of biomedical materials 26 (2013) 43-53).*
English machine translation for 102114271CN.
English machine translation for 2008106024JP.

* cited by examiner

*Primary Examiner* — Devang K Thakor
(74) *Attorney, Agent, or Firm* — King & Schickli PLLC

(57) ABSTRACT

The present invention relates to an injectable system combining a hydrogel, a bioceramic and a degradable matrix that provides for sustained drug delivery and structural support to recovering tissue, such as bone and the periodontium.

12 Claims, 26 Drawing Sheets

FIGURE 1
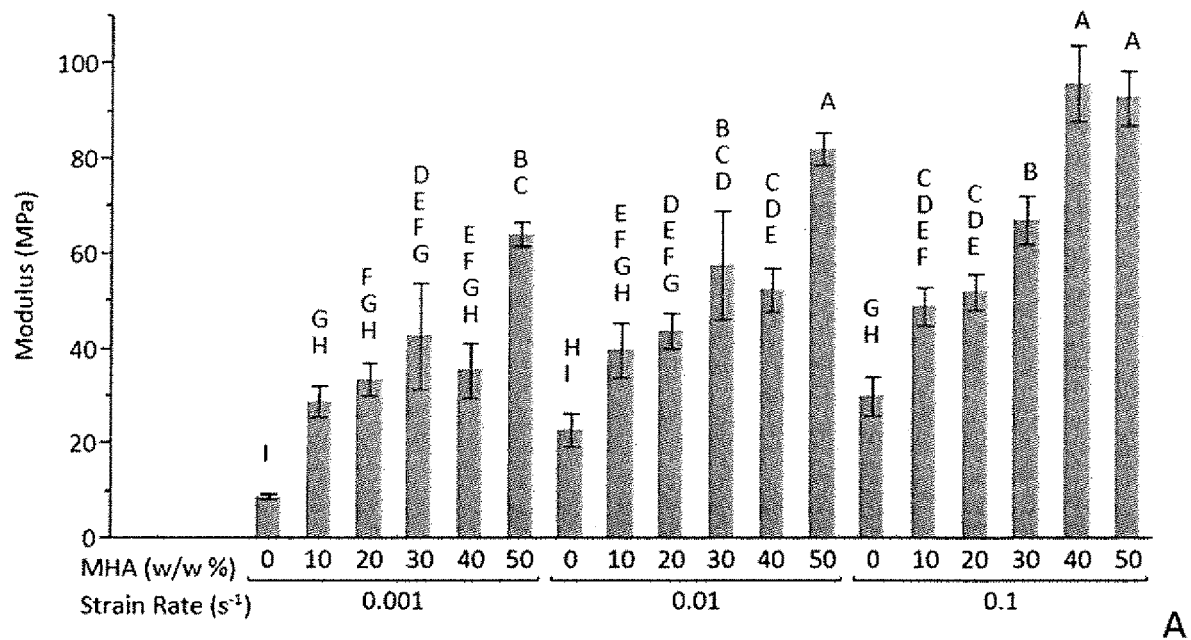
A
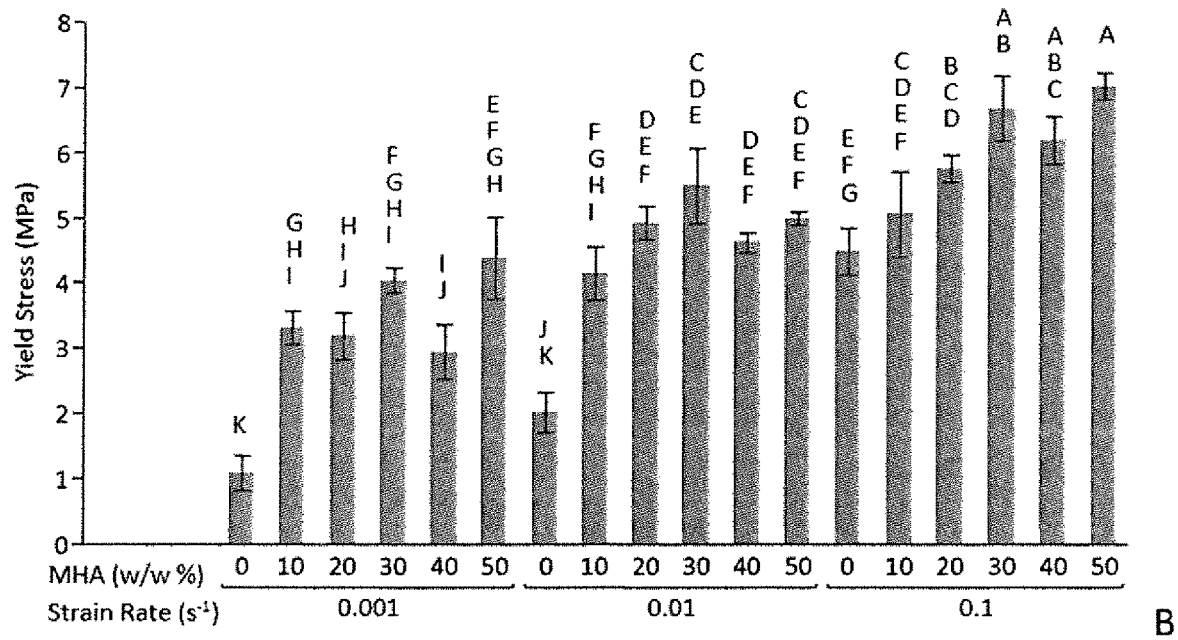
B

FIGURE 2
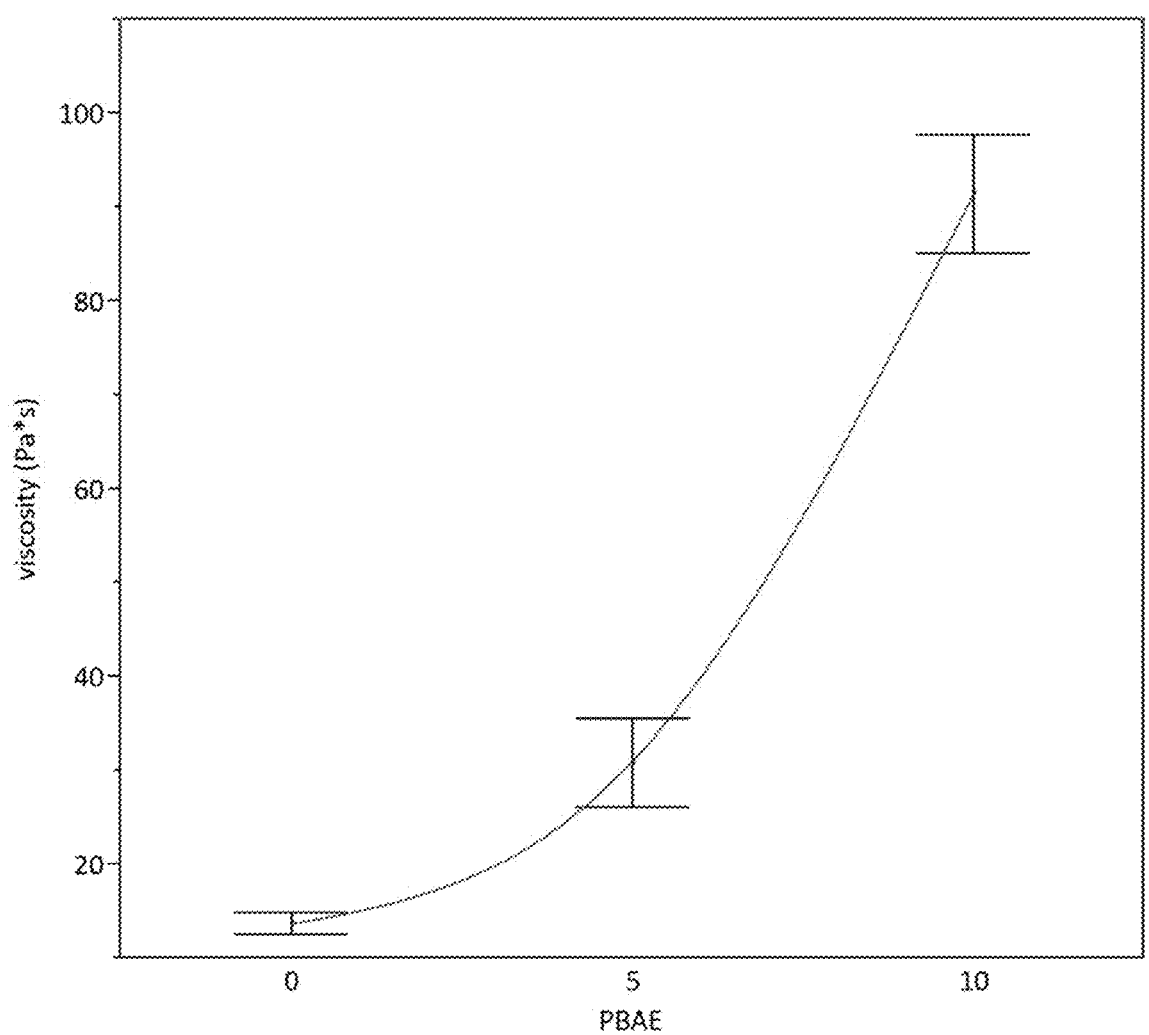
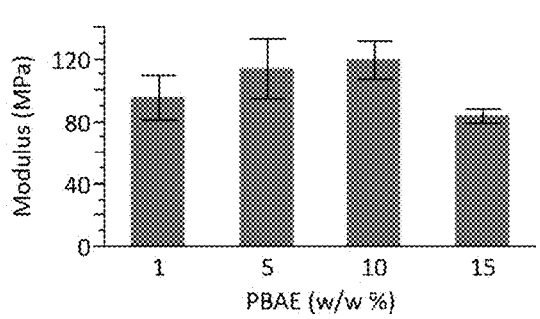
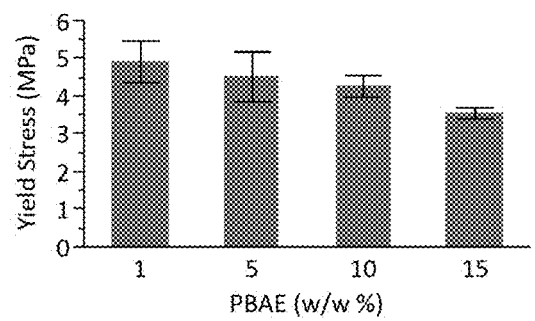

FIGURE 3
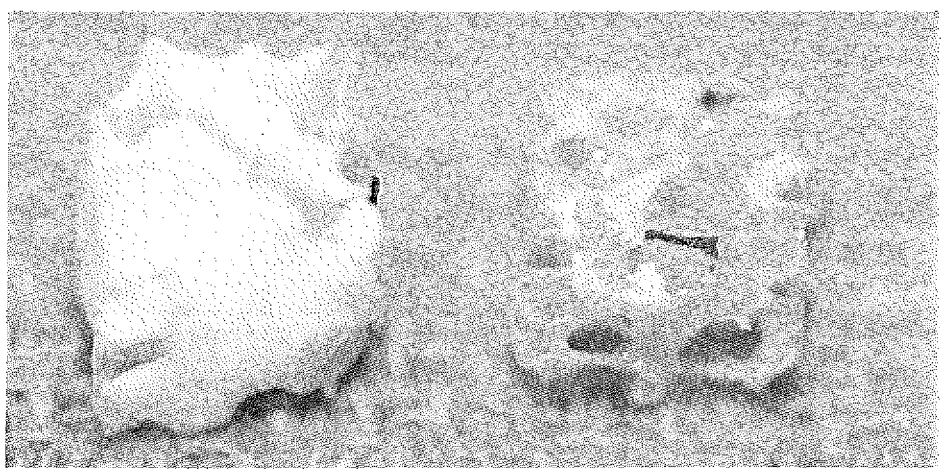
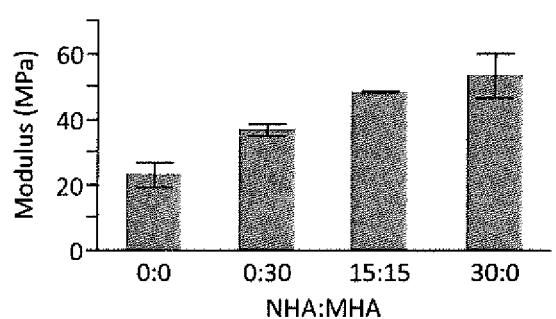 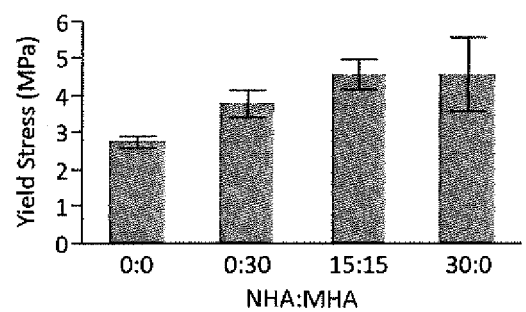

FIGURE 5
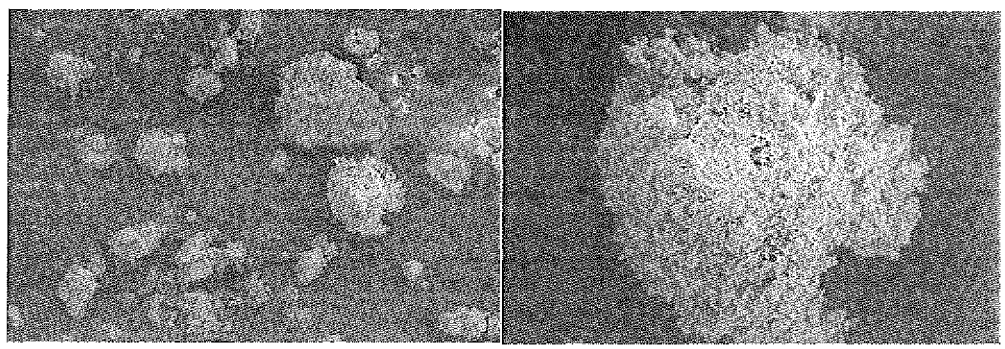
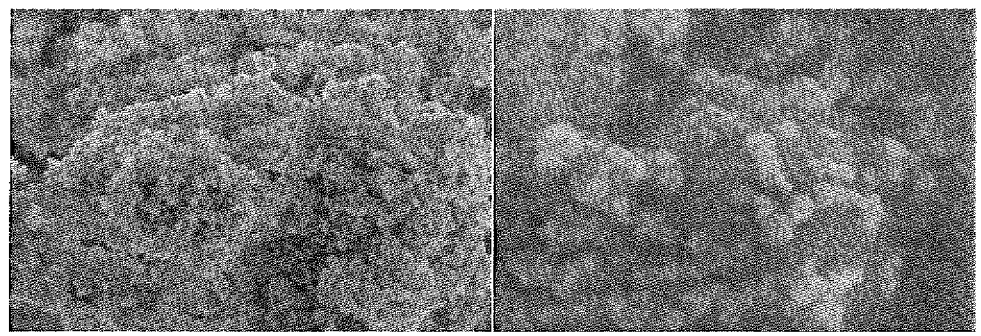

FIGURE 6
A
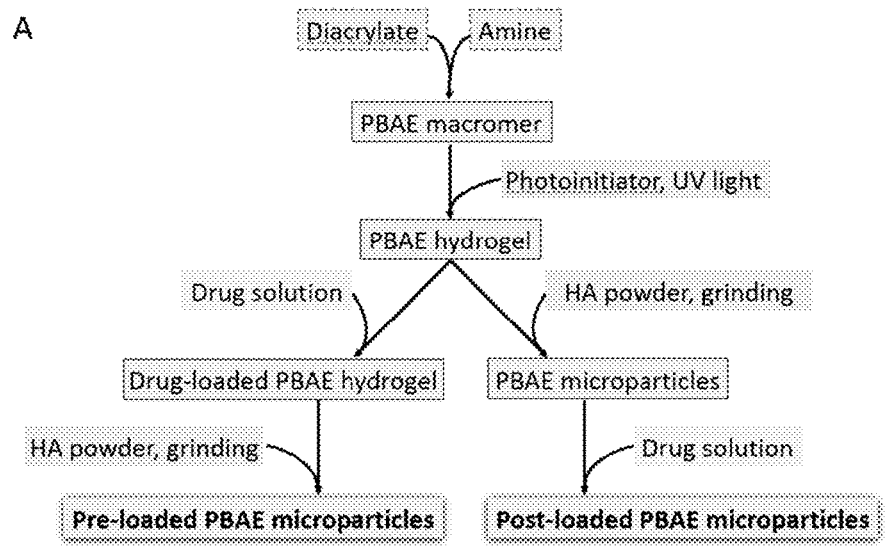
B Proposed System
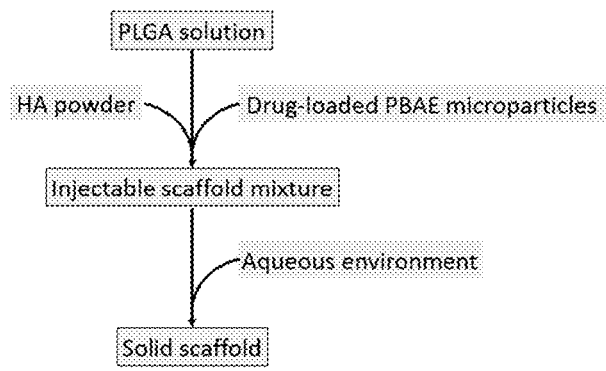
Traditional System
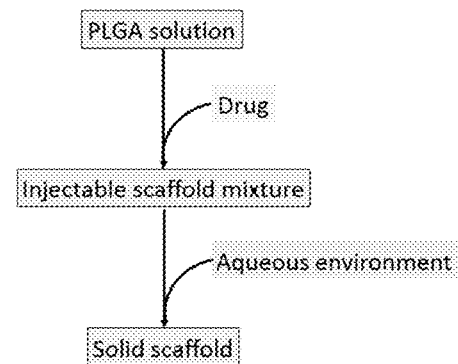

FIGURE 11
A
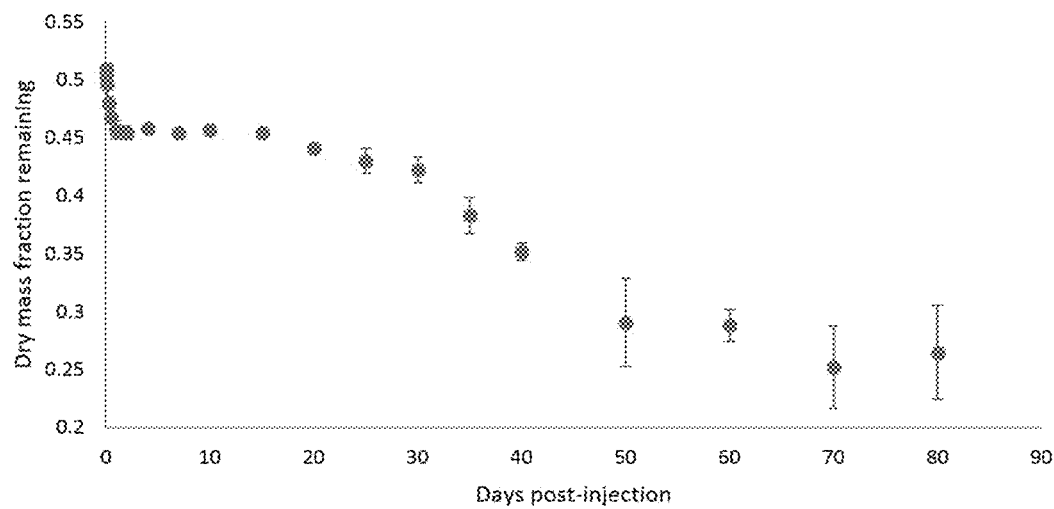
B
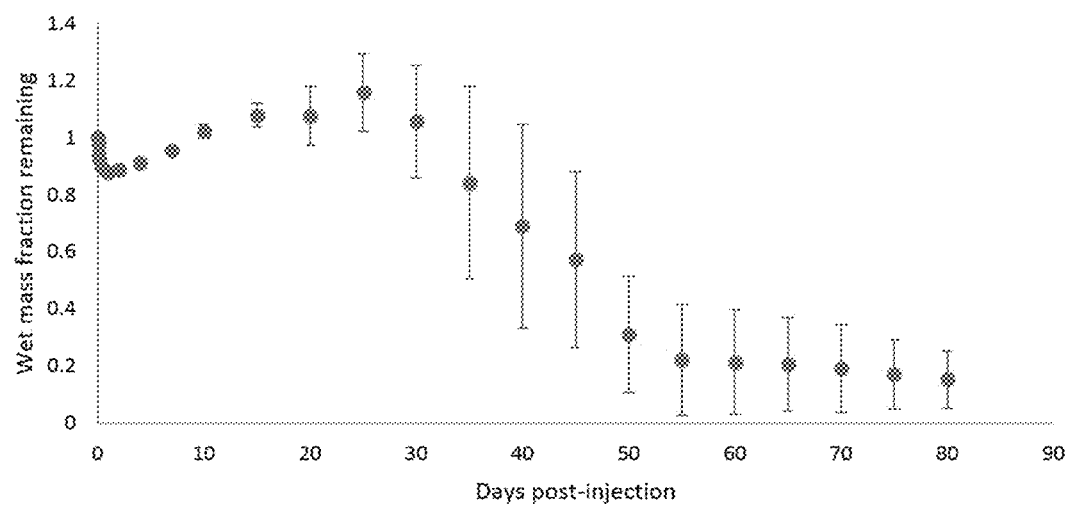

FIGURE 14
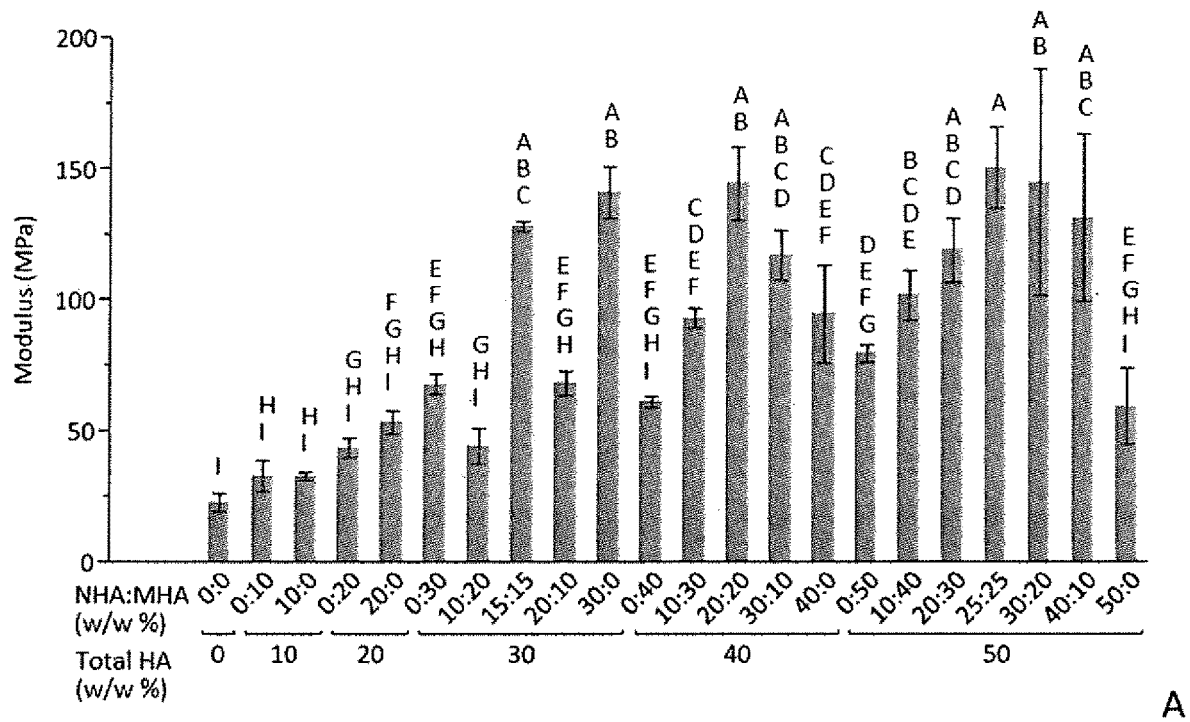
A
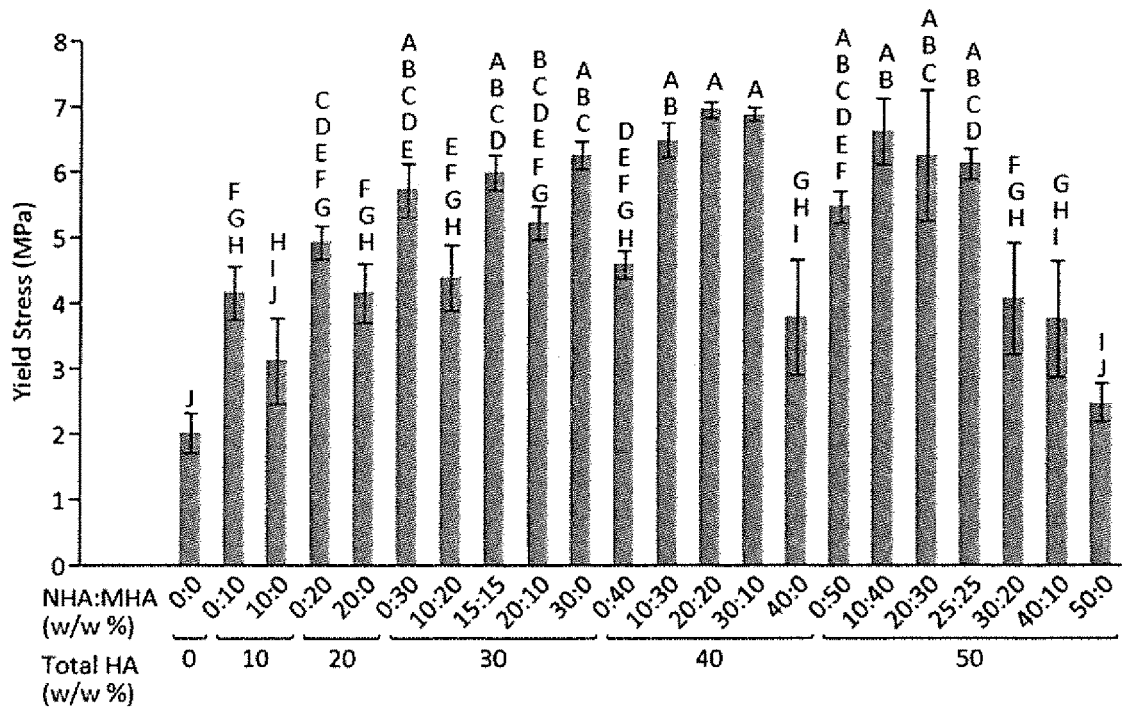
B

FIGURE 15
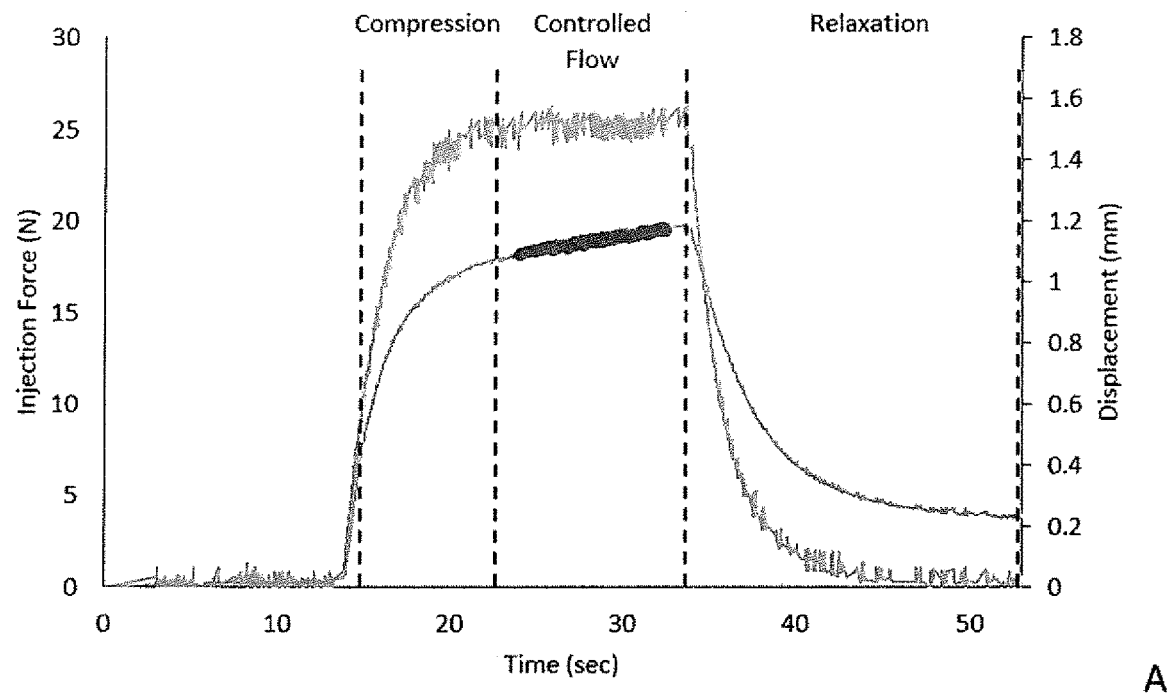
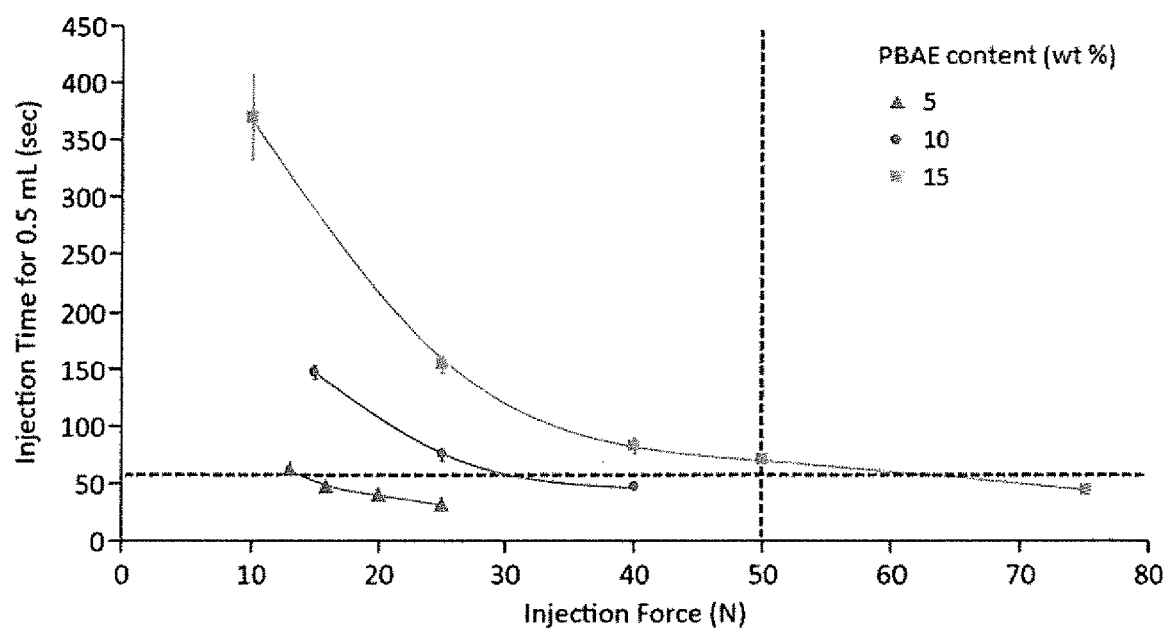

FIGURE 19
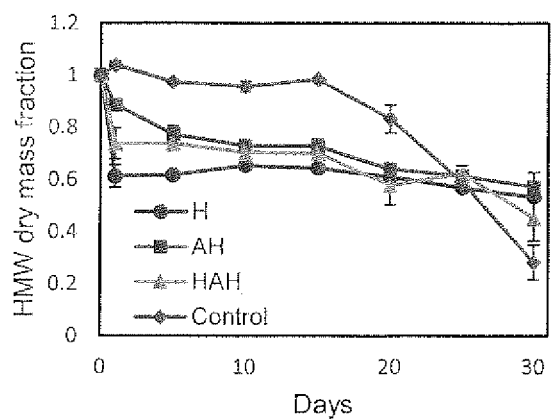
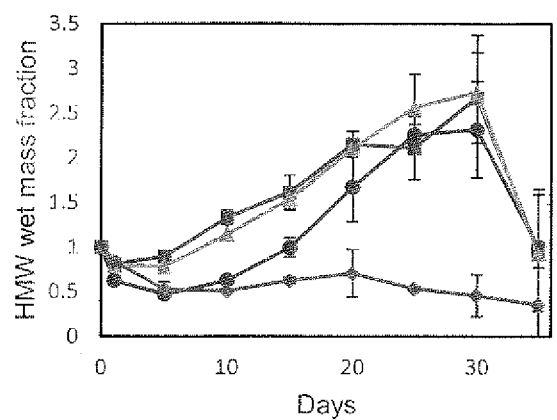
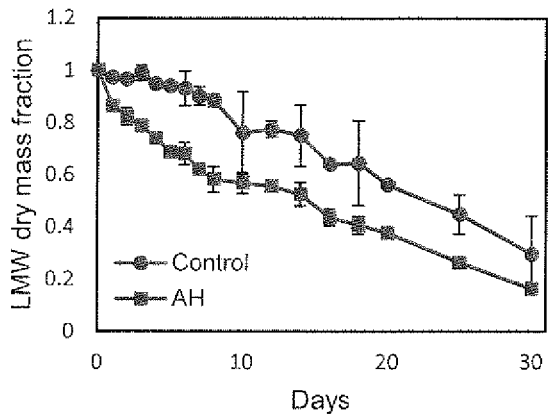
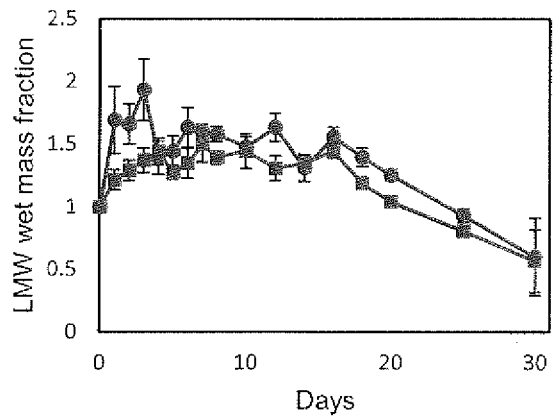

FIGURE 24
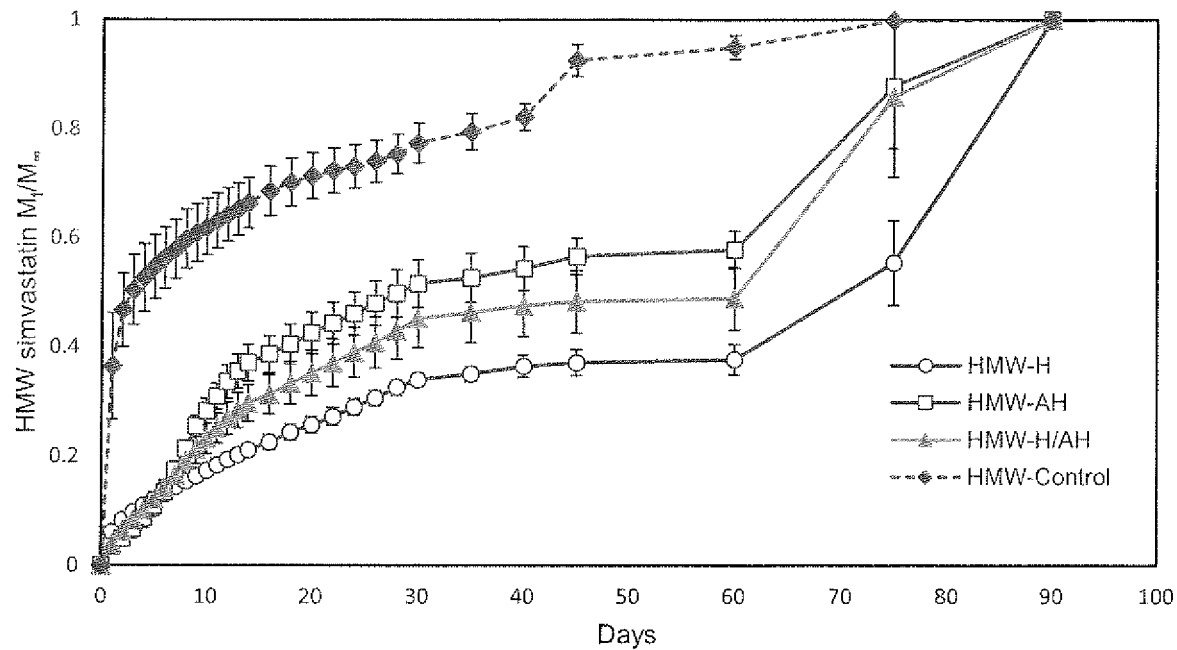
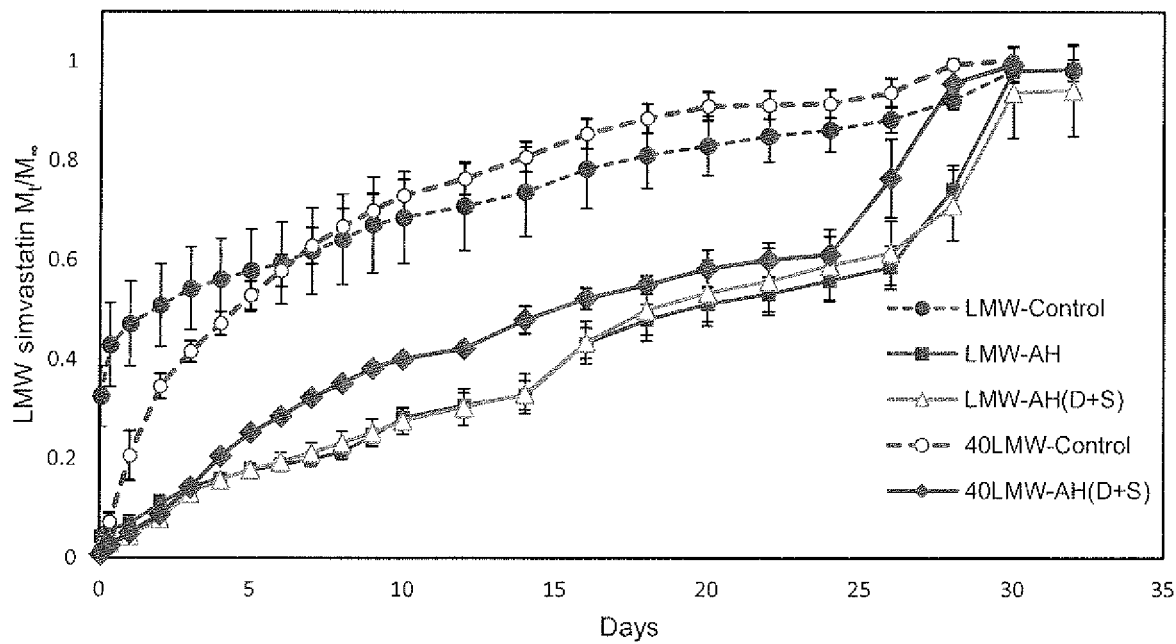

FIGURE 25
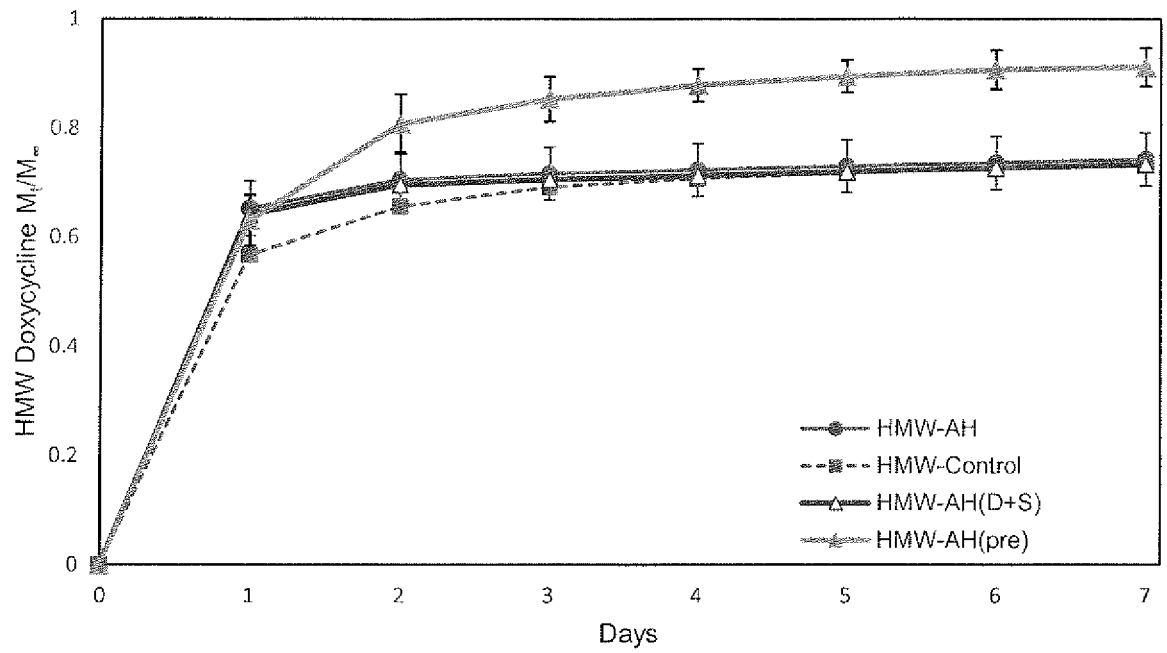
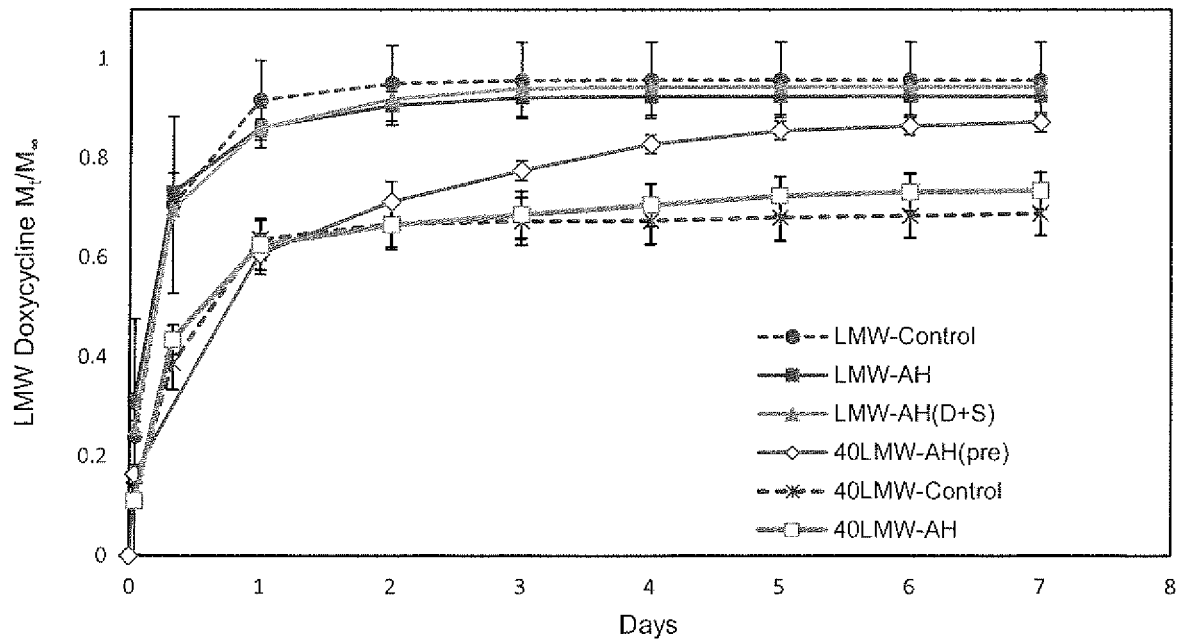

SMALL MOLECULE DRUG RELEASE FROM IN SITU FORMING DEGRADABLE SCAFFOLDS INCORPORATING HYDROGELS AND BIOCERAMIC MICROPARTICLES

RELATED APPLICATIONS

This application claims priority to U.S. Provisional Patent Application 61/975,139, filed 4 Apr. 2014, which is hereby incorporated by reference in its entirety.

GOVERNMENT INTEREST

This invention was made with Government support from National Institutes of Health grant AR060964 and National Science Foundation grants EPS-0814194 and DGE-0653710. The Government may have certain rights in the invention.

TECHNICAL FIELD

The present invention relates generally to injectable scaffolds for sustained drug delivery in recovering tissues, such as bone and the periodontium.

BACKGROUND

In situ forming implants ("ISIs") have been investigated primarily for injection into soft tissue for sustained drug delivery (Hatefi A, Amsden B. Biodegradable injectable in situ forming drug delivery systems. Journal of Controlled Release 2002; 80(1-3):9-28). These systems were conceived due to the phase separation observed when a hydrophobic polymer dissolved in a water-miscible organic solvent is introduced to an aqueous environment, resulting in solidification of the polymer matrix (Shah N H, Railkar A S, Chen F C, Tarantino R, Kumar S, Murjani M, Palmer D, Infeld M H, Malick A W. A biodegradable injectable implant for delivering micro and macromolecules using poly(lactic-co-glycolic) acid (PLGA) copolymers. Journal of Controlled Release 1993; 27(2):139-147), By mixing drugs into the polymer phase prior to injection, a drug-loaded, solid depot can form upon injection into the body. Such systems are available in FDA-approved formulations, such as ATRI-DOX®, for delivery of doxycycline into gum tissue, and ATRIGEL®, which is approved for delivery of leuprolide acetate for treatment of prostate cancer. These systems provide prolonged drug release, with an initial burst dependent on drug and solvent properties and a release period dependent on drug and polymer properties (Parent M, Nouvel C, Koerber M, Sapin A, Maincent P, Boudier A. PLGA in situ implants formed by phase inversion: Critical physicochemical parameters to modulate drug release. Journal of Controlled Release 2013; 172(1):292-304). As such, these injectable systems avoid the additional trauma that would be needed for implantation of large, solid dosage forms. Furthermore, the polymers are hydrolytically degradable, so there is no secondary surgery required to remove an implant after drug delivery is complete (Kenley R A, Lee M O, Mahoney T R, Sanders L M, Poly(lactide-co-glycolide) decomposition kinetics in vivo and in vitro. Macromolecules 1987; 20(10):2398-2403). Because these polymer systems are locally injectable and space-filling, they should be able to infiltrate and conform to complex geometries, such as a network of trabecular bone. However, these materials offer little in the way of structural support. The present invention provides an injectable system for recovering bone or periodontal tissue that provides for sustained drug delivery with structural support.

SUMMARY OF THE INVENTION

The present invention provides an injectable system for assisting in osseous tissue repair, the system comprising a degradable matrix in a solvent, a hydrogel and a ceramic. The degradable matrix may be selected from PLGA, poly (lactic acid) and poly(ε-caprolactone). The ceramic may be selected from the group consisting of hydroxyapatite (HA), brushite, calcium polyphosphate, β-tricalcium phosphate, and monetite. PLGA may comprise different L:G ratios, such as between 50:50 to 95:5, further up to 100:0 to include poly(acetic acid) or 0:100 for poly(glycolic acid. PLGA may comprise a molecular weight range between 5 and 300 kDa and an endcap of carboxylate or an ester-linked hydrocarbon. The hydrogel may be selected from the group consisting of poly(β-amino ester) (PBAE), methoxy poly(ethylene glycol)-poly(lactic-co-glycolide), poly(ethylene glycol)-poly(lactic-co-glycolide)-poly(ethylene glycol), alginate hydrogels, and hyaluronan hydrogels-poly(lactic-co-valerolactone). The solvent may be selected from the group consisting of N-methyl-2-pyrrolidone, dimethyl sulfoxide, ethyl acetate, ethyl benzoate, and triacetin.

In certain embodiments, the injectable system may comprise between 15 and 45 w/w % as the degradable matrix and between 15 and 45 w/w % (+/−10%) as the ceramic and between 3-25 w/w % (+/−10%) as the hydrogel. In other embodiments, the injectable system may comprise 193 w/w % degradable matrix, 45.5 w/w % solvent, 30 w/w % ceramic and 5 w/w % drug-loaded hydrogel. In yet further embodiments, the injectable system may comprise 18 w/w % degradable matrix, 42 w/w % solvent, 30 w/w % ceramic and 10 w/w % drug-loaded hydrogel.

The hydrogel may be pre-loaded with a therapeutic agent. For example, the therapeutic agent may be selected from the group consisting of coldronate, alendronate, etidronate, zoledronate, simvastatin, lovastatin, rosuvastatin, SVAK-12, bone morphogenetic proteins, parathyroid hormone (1-34), metronidazole, doxycycline, vancomycin, gentamycin, ciprofloxacin, ketoprofen, celecoxib, diclofenac, meloxicam or mixtures thereof.

The present invention also provides methods of preparing an in situ injectable system for osseous tissue, comprising mixing a hydrogel, a ceramic and a degradable matrix. The hydrogel may be preloaded or be admixed at the point of care with at least one pharmaceutical agent. The degradable matrix may be further cross-linked. The hydrogel may be mixed with the degradable matrix prior to cross-linking.

BRIEF DESCRIPTION OF THE DRAWINGS

FIG. 1 shows mechanical properties of cylindrical scaffolds prepared with different MHA content and tested at multiple strain rates. A) Compressive modulus. B) Yield stress. Data are grouped by displacement rate and ordered by increasing MHA content. Shared letters denote statistical similarity, and columns without a single shared letter are significantly different. Data are mean±standard deviation (n=3).

FIG. 2 shows representations of viscosity and mechanical properties for scaffolds containing various hydrogel microparticle content, formulated with 30% total NHA and the remainder of the weight composed of 30% PLGA in NMP. Shared letters denote statistical similarity, and columns without a single shared letter are significantly different. Data are mean±standard deviation (n=3).

FIG. 3 shows, using SAWBONES® open cell rigid polyurethane foams made to mimic trabecular bone architecture, two 5×5×5 mm$^3$ samples with and without the mixture injected, demonstrating the space-filling capability of the mixture. The samples receiving injections were immersed in buffer for 3 days to ensure complete solidification of the PLGA. Also included are graphs showing mechanical properties of Sawbones injected with varying weight percentages of NHA and MHA. Again, 30% NHA provided the most benefit, and 15% NHA/15% MHA were comparable. Modulus is lower than pure scaffolds due to imperfect geometry and the inferior mechanical properties of the Sawbones themselves.

FIG. 5 shows composite PBAE particles, with homogeneous distribution of HA throughout particles. HA and PBAE are indistinguishable, though at higher magnification, spherical nanostructures can be seen all over the surface of the material. Because PBAE was polymerized around HA, there is no discrete HA powder visible, and all HA content is encased in polymer, which supports the superior drug loading properties of these composite microparticles.

FIG. 6 shows PBAE microparticle and injectable scaffold fabrication process. A) Technique for formation of PBAE hydrogels and processing them into drug-containing pre- or post-loaded microparticles. B) Comparison of a traditional injectable PLGA system (right) to the proposed system (left).

FIG. 11 shows degradation of in situ forming PLGA scaffolds. A) Destructive mass loss showing dry mass change expressed as a fraction of pre-injection mass (n=3). B) Non-destructive mass loss showing total hydrated scaffold mass change, expressed as a fraction of pre-injection volume (n=5). Data are mean±standard deviation.

FIG. 14 shows mechanical properties of scaffolds prepared with different MHA:NHA ratios, grouped by increasing total HA content (w/w %) and subsequently ordered by increasing MHA content (w/w %). A) Compressive modulus. B) Yield stress. Shared letters denote statistical similarity, and columns without a single shared letter are significantly different. Data are mean±standard deviation (n=3).

FIG. 15 shows injectability of 30% NHA scaffold mixtures prepared with varying PBAE microparticle content. A) Representative graph of collected force (green curve, left axis) and displacement (blue curve, right axis) data, with the highlighted linear portion of the displacement used to calculate volumetric flow rate. B) Time required to inject 0.5 mL from a 16 gauge needle for various injection forces and PBAE microparticle contents. The dotted lines indicate reasonable limits for injection time for 0.5 mL (60 sec) and injection force (50 N). Data are mean±standard deviation (n=3).

FIG. 19 shows mass loss of ISIs. Remaining dry mass of A) HMW scaffolds and C) LMW scaffolds. Remaining wet mass of B) HMW scaffolds and D) LMW scaffolds. Data are mean±standard deviation (n=3).

FIG. 24 shows simvastatin release from A) HMW and B) LMW scaffolds. D+S indicates that scaffolds were co-loaded with simvastatin and doxycycline. Data are mean±standard deviation (n=3).

FIG. 25 shows doxycycline release from A) HMW and B) LMW ISIs. D+S indicates that scaffolds were co-loaded with simvastatin and doxycycline. Pre indicates that doxycycline was pre-loaded into PBAE microparticles. Data are mean±standard deviation (n=3).

DESCRIPTION

Figure 4:
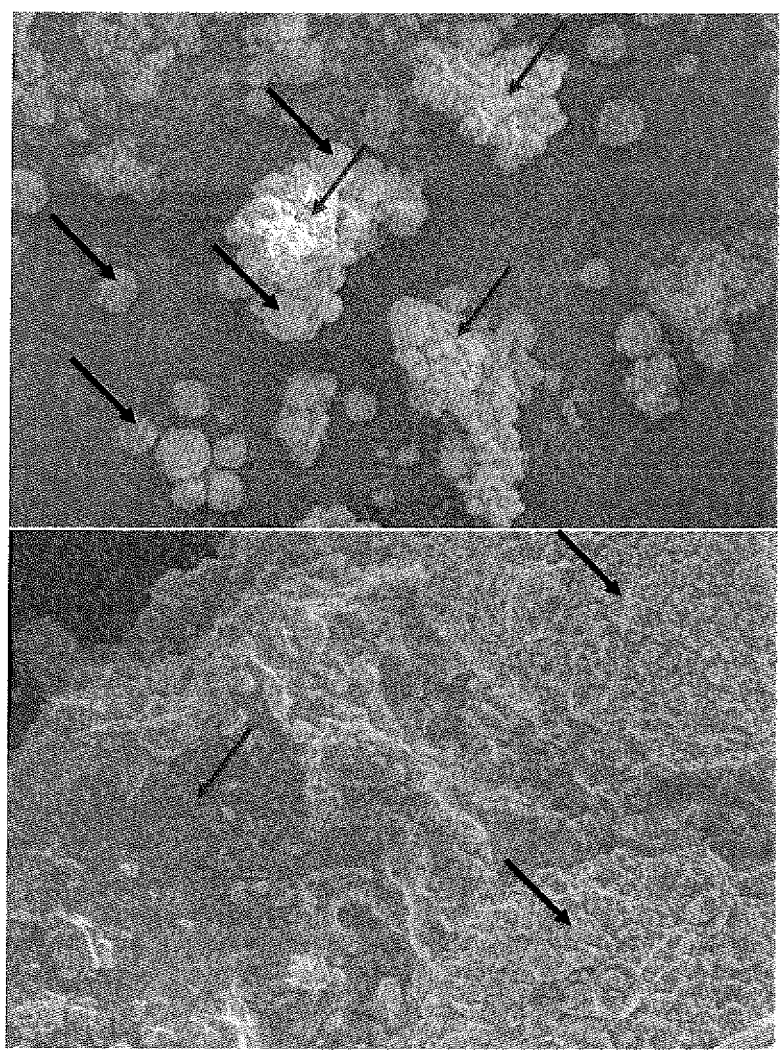
FIG. 4 shows PBAE particles, with unbound HA microparticles (black arrows) and PBAE hydrogel (white arrows) labeled. HA particles can also been seen coating the PBAE particles. At the highest magnification, HA microparticles can be seen to be composed of aggregated nanoparticles.

Controlled drug delivery systems offer a variety of potential advantages over traditional routes of administration, such as oral dosages and intravenous or subcutaneous injection of drug solutions, due to their spatial and temporal control over drug release (Allen T M, Cullis P R. Drug Delivery Systems: Entering the Mainstream. Science 2004; 303:1818-22). Traditional dosage forms result in systemic circulation of drug, and the oral route is also subject to first-pass metabolism (Veber D F, Johnson S R, Cheng H-V, Smith B R, Ward K W, Kopple K D. Molecular Properties That influence the Oral Bioavailability of Drug Candidates. Journal of Medicinal Chemistry 2002; 45:2615-23). Injections introduce a bolus of drug at high concentrations, and long-term treatment requires repeated dosing, resulting in pulsatile concentration profiles (Uhrich K E, Cannizzaro S M, Langer R S, Shakesheff K M. Polymeric systems for controlled drug release. Chemical reviews 1999; 99:3181-98). Implantable drug-loaded scaffolds can be placed at the treatment site to minimize systemic exposure and can be designed to control release kinetics by varying the chemical and physical nature of the carrier (Uhrich K E, Cannizzaro S M, Langer R S, Shakesheff K M. Polymeric systems for controlled drug release. Chemical reviews 1999; 99:3181-98; Garg T, Singh O, Arora S, Murthy R. Scaffold: a novel carrier for cell and drug delivery. Critical reviews in therapeutic drug carrier systems 2012; 29:1-63). These systems, however, generally require a surgical procedure to implant the device, and in the case of a non-degrading material, require a removal surgery. As a result, significant effort in the drug delivery field has focused on injectable, biodegradable drug carriers, such as in situ gelling, polymerizing, or precipitating systems (Hatefi A, Amsden B. Biodegradable injectable in situ forming drug delivery systems. Journal of Controlled Release 2002; 80:9-28; Packhaeuser C B, Schnieders J, Oster C G, Kissel T. In situ forming parenteral drug delivery systems: an overview. European Journal of Pharmaceutics and Biopharmaceutics 2004; 58:445-55). A space-filling scaffold capable of forming into a biodegradable solid at the treatment site is an appealing option because it can penetrate a tissue network to deliver drugs at a fixed location with minimal invasiveness and no removal surgery. Additional background for the present invention can be found as follows: Fisher, P. D., Palomino, P., Milbrandt, T. M., Hilt, J. Z., and Puleo, D. A. (2014). Improved small molecule drug release from in situ forming polylactic-co-glycolic acid) scaffolds incorporating poly(β-amino ester) and hydroxyapatite microparticles, J. Biomater. Sci. Polym. Ed. 25:1174-1196; Fisher, P. D., Venugopal, G., Milbrandt, T. A., Hilt, J. Z., and Puleo, D. A. (2015). Hydroxyapatite-reinforced in situ forming PLGA systems for intraosseous injection, J. Biomed. Mater. Res. Part A, doi: 10.1002/jbm.a.35375; Fisher, P. D., Clemens, J., Hilt, J. Z., and Puleo, D. A. (2015). Multifunctional poly(β-amino ester) hydrogel microparticles in periodontal in situ forming drug delivery systems (in review); Fisher, P. D., Milbrandt, T. M., Hilt, J. Z., and Puleo, D. A. (2013). In situ forming drug delivery scaffold for treating avascular necrosis of the femoral head. Presented at the 2013 Annual Meeting of the Society For Biomaterials, April 10-13, Boston, Mass.; Fisher, P. D., Milbrandt, T. M., Hilt, J. Z., and Puleo, D. A. (2014). Drug release and mechanical effects of poly(β-amino ester) and hydroxyapatite on in situ forming PLGA systems. Presented at the 2014 Annual Meeting of the Society For Biomaterials, April 16-19, Denver, Colo.; Fisher, P. D., Milbrandt, T. M., Hilt, J. Z., and Puleo, D. A. (2014). Improving properties of in situ forming PLGA implants via poly(β-amino ester) and hydroxyapatite additives. Presented at the 2014 Annual Meeting of the Biomedical Engineering Society, October 22-25, San Antonio, Tex.; Fisher, P. D., Milbrandt, T. M., Hilt, J. Z., and Puleo, D. A. (2015). An in situ forming, injectable PLGA composite for orthopedic applications. To be presented at the 2015 Annual Meeting of the Society For Biomaterials, April 15-18, Charlotte, N.C.

The present invention provides a system for delivery of therapeutic and structural support into bone, joint and periodontal sites. The system of the present invention provides a composition comprised of a degradable matrix, a ceramic, and a hydrogel in a solvent. Suitable degradable matrices may include, but are not limited to: PLGA with different L:G ratio, molecular weight, and endcap; poly(lactic acid); and poly(ε-caprolactone); suitable ceramics may include, but are not limited to: hydroxyapatite (HA), brushite, calcium polyphosphate, β-tricalcium phosphate, and monetite; suitable hydrogels may include, but are not limited to: poly(β-amino ester) (PBAE), methoxy poly(ethylene glycol)-poly(lactic-co-glycolide), poly(ethylene glycol)-poly(lactic-co-glycolide)-poly(ethylene glycol), alginate hydrogels, and hyaluronan hydrogels; and suitable solvents may include, but are not limited to: N-methyl-2-pyrrolidone (NMP), dimethyl sulfoxide, ethyl acetate, ethyl benzoate, and triacetin. Hydrogels may be preloaded with a pharmaceutical agent or admixed by a practitioner just prior to injection of the system.

The system of the present invention may be injected into different sites and may further incorporate multiple therapeutic agents. Accordingly, the system can be utilized in procedures requiring improved structural support with the added benefit of in situ sustained drug delivery. For example, the present invention may be utilized in dental, craniofacial, and orthopedic applications. These include adult avascular necrosis of bone, large bone segmental defects resulting from trauma, hip and knee replacement revision with bone loss, reconstruction following bone tumor resection, and treatment of periodontal defects.

The system of the present invention may further include a therapeutic agent or more thereof within the hydrogel or the matrix itself. Suitable therapeutic agents may comprise agents for decreasing inflammation, increasing osteogenesis, preventing resorption and preventing infection. These include, but are not limited to the following.

Antiresorptive: clodronate, alendronate, etidronate, and zoledronate

Osteogenic: simvastatin, lovastatin, rosuvastatin, SVAK-12, bone morphogenetic proteins, and parathyroid hormone (1-34)

Antimicrobial: metronidazole, doxycycline, vancomycin, gentamycin, and ciprofloxacin Anti-inflammatory: ketoprofen, celecoxib, diclofenac, and meloxicam The system of the present invention offers improved release kinetics, multiple release profiles, and rapid solidification compared to traditional in situ forming implants (ISIs). Incorporating drug-loaded microparticles into an injectable degradable matrix system may provide a secondary means of controlling release kinetics. Intraosseous injection in particular is a suitable application for the in situ forming system of the present invention due to the interconnected porous network of the trabecular bone that makes placement of pre-formed scaffolds difficult and removal surgery impossible. The injectable degradable systems can accommodate filler particles such as bioceramics, such as hydroxyapatite (HA), to influence microarchitecture, mechanical properties, or osteoconductivity.

Those skilled in the art will appreciate that the physical characteristics of the system can be varied by altering the concentrations of each component within the system. While, the composition of the system can be varied significantly, attention should include focus on resulting effects on drug content, mechanical properties, and "injectability". One embodiment of the present invention provides for 30 w/w % (+/−15%) of the degradable matrix in solvent (solvent provides 30-60 w/w %); 30 w/w % (+/−10%) of the bioceramic particles and 5-10 w/w % (+/−10%) of the hydrogel particles. For example, the system may comprise a 30 w/w % PLGA solution in NMP, 30 w/w % HA nanopowder and 3-20% w/w % PBAE microparticles (depending on desired drug loading; 10% PBAE does not affect mechanical properties but does increase viscosity, which makes the solution more difficult to inject).

For example, in one embodiment, the system may comprise, by weight:
  19.5% degradable matrix (e.g. PLGA)
  45.5% solvent (e.g. NMP)
  30% bioceramic (e.g. HA nanopowder)
  5% drug-loaded hydrogel (e.g. PBAE microparticles)

Such compositions provide the advantage of a low viscosity and higher injectability, but offer reduced capacity for drug loading.

In another embodiment, the system may comprise, by weight:
  18% degradable matrix (e.g. PLGA)
  42% solvent (e.g. NMP)
  30% bioceramic (e.g. HA nanopowder)
  10% drug-loaded hydrogel (e.g. PBAE microparticles)

Such compositions provide the advantage of increased drug loading but with a high viscosity/lower injectability. Increasing the hydrogel microparticle content to 15% or higher has demonstrated a negative effect on mechanical properties.

In general, increasing bioceramic content increases compressive modulus and yield stress to up until approximately 30% of the total weight of the system, and after such has either negative or no effect on these properties.

The system may further provide for a mixture of bioceramics. For example, generally, nano-HA (NHA) demonstrated more benefit than micro-HA (MHA) at equivalent concentrations, and NHA also provided the largest maximum compressive moduli and yield stresses. However, one of the highest compressive moduli was observed at 30% NHA content and with a mixture containing 15% MHA and 15% NHA, both of which provided similarly high properties. The compressive modulus of a 30% NHA mixture was comparable to that of trabecular bone, making a 30% NHA formulation a good mechanical match for the proposed system. FIG. 1 shows a graph of modulus (A) and yield stress (B) as a function of HA content.

Increasing hydrogel content increases viscosity almost exponentially, while mechanical properties are unaffected until 15% (by weight). By varying hydrogel content, a thicker or thinner mixture can be formulated with little to no mechanical implications. A more viscous injectable may be suitable for larger defects or more osteoporotic bone, since the paste will begin to solidify before it can escape the injection site. A less viscous formulation is suitable for collapsed bone or for regions of trabecular bone with lower pore size, since the injection rate can be maximized to fill dense trabecular networks. FIG. 2 shows representations of viscosity and mechanical properties for scaffolds containing various hydrogel microparticle content, formulated with 30% total NHA and the remainder of the weight composed of 30% PLGA in NMP.

The injectable system of the present invention can fill complex geometry, such as trabecular bone. FIG. 3 illustrates, using SAWBONES® open cell rigid polyurethane foams made to mimic trabecular bone architecture, two 5×5×5 mm$^3$ samples with and without the mixture injected, demonstrating the space-filling capability of the mixture. The samples receiving injections were immersed in buffer for 3 days to ensure complete solidification of the PLGA. Also included are graphs showing mechanical properties of SAWBONES® injected with varying weight percentages of NHA and MHA. Again, 30% NHA provided the most benefit, and 15% NHA/15% MHA were comparable. Modulus is lower than pure scaffolds due to imperfect geometry and the inferior mechanical properties of the Sawbones themselves.

The system of the present invention can be adapted for a variety of intraosseous treatments, with properties tuned to fit the application. Both adult and pediatric avascular necrosis are targets for this treatment, and the drug content, viscosity, and mechanical properties can be modified appropriately. In addition, compression fractures and bone cysts are other applications for such a system where local intraosseous delivery, space-filling, and solidification of a drug delivery matrix are needed.

Those skilled in the art will appreciate that the bioceramic particles can be mixed with the matrix either prior or post cross-linking of the hydrogel. For example, bioceramics, such as HA, can be mixed with a hydrogel, such as PBAE, prior to cross-linking. Recent research has explored a new composite ceramic-hydrogel microparticle instead of hydrogel microparticles coated with ceramic, creating composite ceramic-hydrogel sheets that can be easily ground into microparticles without requiring additional ceramic as a dispersant. This technique provide several advantages:

1. Composite particles retain virtually all therapeutic agent (e.g. simvastatin) (99%) after a surface wash with buffer, while previous particles retained approximately 50%. This can be attributed to absence of bioceramic aggregates, which can loosely adsorb drug that ends up washed off. Further, composite particles have a homogeneous distribution, e.g. of micro- and nanoscale HA particles, throughout the particle volume (see FIG. 4), so therapeutics should be retained within particles rather than loosely bound to free HA.
2. Composite particles contain a relatively higher hydrogel content (33 w/w % vs 25 w/w %). This allows of higher drug loading with equivalent hydrogel content, which can either increase total drug dose or reduce the viscosity of the injectable mixture at equivalent doses.

3. The fabrication process of composite particles leads to bioceramic particles uniformly distributed throughout the composite particle volume, while the previous technique resulted in bioceramic aggregates primarily on the surface of particles, as well as bioceramic aggregates unbound to any hydrogel. These microstructural differences are illustrated in the SEM images of FIG. 4.

The examples described below demonstrate varying loaded therapeutic agents within the system, as well as mechanical properties and the overall texture and viscosity to allow for injection. In general, increasing the bioceramic concentration, such as increasing micro-HA (MHA) or nano-HA (NHA) content, increases the system's compressive modulus and yield stress (generally, NHA provides more benefit than MHA at equivalent concentrations, and NHA also provides the largest maximum compressive moduli and yield stresses). By varying the concentration of hydrogel present, such as PBAE content, a thicker or thinner mixture can be formulated with little to no mechanical implications. The injectable mixture is also capable of filling complex trabecular geometry. The system of the present invention can be adapted for a variety of intraosseous treatments, with properties tuned to fit the application. Both adult and pediatric avascular necrosis are conditions that can benefit from this system, and the drug content, viscosity, and mechanical properties can be modified appropriately. In addition, compression fractures and bone cysts are other applications for such a system where local intraosseous delivery, space-filling, and solidification of a drug delivery matrix are needed.

Figure 8:
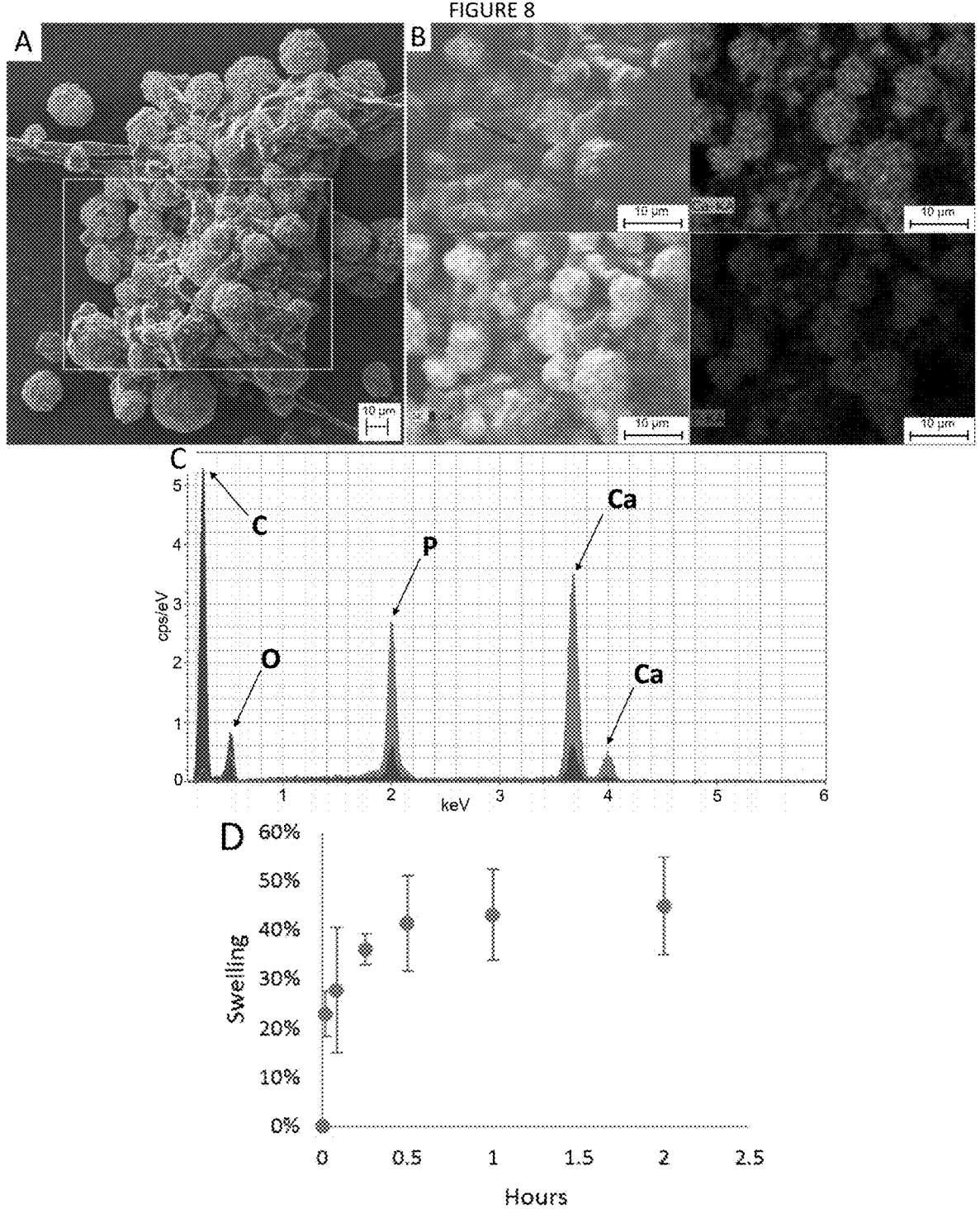
FIG. 8 shows morphology, composition, and swelling of PBAE microparticles. A) SEM image of a PBAE microparticle, with EDS performed on the highlighted portion. B) Top left: Region chosen from (A) for EDS analysis, with arrows indicating points of spectral analysis performed in (C). Bottom left: Composite overlay of calcium and phosphorous on that region. Top right: EDS detection of calcium. Bottom right: EDS detection of phosphorous. B). C) EDS spectra of an HA particle (upper right) and PBAE (lower right). D) PBAE swelling kinetics expressed as a percentage of mass increase in injection mixture (30 wt % HA mixed into 20% PLGA solution). Data are mean±standard deviation (n=3).

The present invention provides for incorporating hydrogel microparticles into a degradable matrix to provide several new functions: mechanical support, porosity, space-filling, and controlled co-delivery of antibiotics and osteogenic drugs. Combining all these functions provides a more effective space-filling scaffold and offers improved release kinetics compared to existing systems used. Further, the system of the present invention provides for acute antibiotic delivery accompanied by co-delivery of an antibiotic and an osteogenic agent with improved effects on swelling, degradation, microarchitecture, and mechanical properties. (see, e.g., bisected microCT reconstructions (FIGS. 5 and 8).

Hydrogel particle additives act as both porogens and drug delivery vehicles within the solid degradable matrix. Hydrogel microparticles also influence macro- and microstructural changes of the matrix as it degrades. Hydrogel microparticles further cause the degradable matrix to adopt a porous network microarchitecture with no difference between surface or central pore sizes, because the homogeneous distribution of hydrogel microparticles act as a template for uniform matrix precipitation. As set out in the examples, the lattice-like matrix network of hydrogel-containing implants provide sustained mechanical resilience even after the degradation period of the matrix had passed. The increased porosity and accessible surface area of hydrogel-containing degradable matrices offers many advantages when considering matrix functions as a potential scaffold rather than solely a drug delivery device.

The swelling of hydrogels provides for improved space-filling and pocket retention of implants. As set forth in the examples, even at an initial 3-day measurement, HMW-AH samples had significantly higher interfacial strength than controls, and this difference became even more pronounced as the incubation period increased. AH hydrogels were observed to swell beyond 200% of their initial mass within 2 days in PBS, and while this effect is may be muted due to the physical constraint within the matrix, there is enough of an effect to provide 4 to 10-fold higher interfacial strength than controls.

A further benefit of the present invention lies in that a scaffold that expands to fill its injection site as it solidifies is less likely to cause irritation due to movement within the pocket. Furthermore, more contact area between the implant and the tissue means that the released drug has a shorter path to enter the target tissue, and it has a smaller likelihood of being washed away. This swelling-based, space-filling approach is an alternative to other avenues that seek to reduce detachment by improving the adhesion between the polymer surface and surrounding tissue.

The present hydrogel-containing matrices demonstrated improve pocket retention through a 15-day period as compared to other studies using more adhesive components, which demonstrated increased bioadhesion in the first several hours following injection into a simulated pocket (Do M P, Neut C, Delcourt E, Seixas Certo T, Siepmann J, Siepmann F. In situ forming implants for periodontitis treatment with improved adhesive properties. Eur J Pharm Biopharm 2014 88(2): 342-50). As set forth in the examples, PLGA deformed plastically and became stiffer under compression, even at low strains and only 30 compression cycles, while the modulus of HMW-AH samples remained unchanged, demonstrating that hydrogel PBAE additives preserve elasticity. HMW-AH samples were less stiff and retained their modulus throughout cyclic compression, demonstrating that they are more suitable to withstand a dynamic mechanical environment. The lack of change for both modulus and resilience after cyclic loading with the present system provides for the development of more mechanically suitable implants.

As described herein, in situ forming scaffolds according to the present invention were characterized to determine their mechanical properties, injectability, and microarchitecture. Strength was increased approximately three-fold, while compressive modulus was improved approximately 6-fold. Scaffolds retained a uniformly porous microarchitecture, and the bioceramic particles were distributed evenly throughout the matrix. Injectability remained within clinically accepted standards. For example, ex vivo injections into intact porcine femoral heads increased compressive modulus of trabecular bone. The injectable scaffold of the present invention thus offers mechanical reinforcement coupled with drug delivery in a single injection for bone-weakening conditions, such as osteonecrosis or osteoporosis.

An implant that acutely reinforces compromised bone, controls drug release, and gradually degrades to allow regeneration of native tissue can provide a comprehensive treatment in a single injection. Scaffolds with material properties similar to trabecular bone can aid load-bearing while the drug delivery component of the scaffold exerts its effect. It is important to consider these scaffolds as a means for temporary augmentation that can acutely preserve bone while treatment occurs, not as a replacement for healthy bone tissue. Injectability is a unique concern for in situ forming scaffolds, because both bioceramic and hydrogel particle additives increase viscosity. Because prior injectable degradable matrix systems were not intended for mechanical support, and drug is usually mixed freely into the polymer solution, viscosity has not been a limiting factor when designing these systems. However, injectable bone cements and fillers have encountered issues with injectability because they are composed of a liquid phase containing high concentrations of suspended particles (Bohner M, Baroud G.

Injectability of calcium phosphate pastes. Biomaterials 2005; 26(13):1553-1563; Alves H L, Santos L A, Bergmann C P. Injectability evaluation of tricalcium phosphate bone cement. J Mater Sci: Mater Med 2008; 19(5):2241-2246). The scaffold of the present invention demonstrated the capability of filling the bone tissue in all directions. Furthermore, injected bone tissue was significantly stronger and stiffer than native tissue, suggesting that the filling that was achieved is sufficient to greatly improve mechanical properties of trabecular bone.

Injectable scaffold mixtures are capable of being injected through a standard bone biopsy needle, infiltrating trabecular bone, then solidifying to produce scaffolds with mechanical properties comparable to those of trabecular bone. This injectable scaffold offers a treatment platform for ailments requiring both drug delivery and mechanical reinforcement of trabecular bone, and it has the advantage of being easily injectable and fully resorbable.

The scaffold of the present invention provides a space-filling system that can bypass spatial limitations of fixed-form implants. Further, through investigating the present invention, while drugs showed burst release when freely mixed or encapsulated within gelatin microspheres, hydrogel particles allowed for more prolonged release. Scaffold porosity further is important to allow new bone ingrowth, and that the scaffolds will degrade over a period of months allows for accommodation of tissue regeneration.

Bioceramic additives, such as hydroxyapatite, may improve mechanical properties and bind to dianionic drugs, such as bisphosphonates, to reduce initial burst. The addition of these particle types can create a system suitable for intraosseous injection due to the mechanical reinforcement and delivery of both osteogenic and anti-resorptive treatments from a single injection. The ISI system containing drug-loaded hydrogel microparticles exhibited significantly reduced burst (81% vs 39%) and extended release (95% release by 28 days vs 10 days). Compressive modulus and yield stress of cylindrical scaffolds increased up to 30 w/w % bioceramic. Additives were demonstrated to improve both release and mechanical properties of traditional ISIs. Hydrogel microparticles and bioceramics reduced the initial burst of drug release which may be suitable for intraosseous injection where a treatment period of weeks is preferable but rapid precipitation is required. Mechanical properties can be controlled by varying bioceramic content and particle size (e.g., nano may range from 5-10 nm to 100 nm, and micro may range from 0.1-250 µm) and the system was capable of space-filling throughout a trabecular bone-like sample and improving its mechanical properties, which can acutely salvage diseased or damaged bone while the drug release component takes effect.

Bioceramics significantly increased the compressive modulus and strength of the material. Ex vivo injections resulted in good space-filling, and the injected material was constrained by the articular and metaphyseal cartilage boundaries. The addition of bioceramic particles enables in situ forming implants to be used in a variety of orthopedic applications because the mechanical properties can be adjusted simply by varying the bioceramic concentration and particle size. These composite scaffolds have a more homogeneous pore structure, and the high accessibility of these pores allows a greater surface area for potential cell access and tissue contact. The addition of bioceramics also allows these materials to be visualized during injection via fluoroscopy to ensure the target site is receiving the treatment, and the material rapidly solidifies and is effectively retained within the target tissue. Once solidified, the implanted material improves the mechanical properties of bone to prevent collapse of damaged or diseased tissue, and the material degrades over the course of 6 weeks, which is an appropriate period to allow drug release and bone repair.

The present invention also provides methods of using the system. The present invention provides for contacting or administering to a subject the system described herein. As described above, the system can be administered by injection. Those skilled in the art will appreciate that the consistency, viscosity and overall make up of the applied system will determine how the system is injected, affecting such parameters as rate of injection, as well as gauge of needle. Further parameters that can determine the rate of injection, as well as the make of the applied system are the area of the subject to receive the system. Those skilled in the art will appreciate that certain applications will demand a slower solidifying system, while others demand a faster solidifying system. Further still, a subject may receive multiple injections in order to completely fill the area requiring application of the system.

The present invention also provides methods for making the system. As described herein, the components of the system can be added together prior to injection within a subject. Those skilled in the art will appreciate that the time of adding the components altogether can be time sensitive as the fully assembled system will start to solidify. For the system described herein, solidification does not begin until the mixture comes into contact with an aqueous phase. Specifically, the system described herein offers the advantage of indefinite handling time, and the setting time only begins post-injection. Further, as described herein the components or parts thereof, can be mixed together prior to cross linking or post crosslinking. The components can be added together such that of the final system: 30 w/w % (+/−15%) comprises the degradable matrix in solvent (solvent provides 30-60 w/w % of the overall system); 30 w/w % (+/−10%) comprises bioceramic particles and 5-10 w/w % (+/−10%) comprises hydrogel particles. For example, the system may comprise a 30 w/w % PLGA solution in NMP, 30 w/w % HA nanopowder and 3-20% w/w % PBAE microparticles.

EXAMPLES

Example 1

In situ forming implants are an attractive choice for controlled drug release into a fixed location. Currently, rapidly solidifying solvent exchange systems suffer from a high initial burst, and sustained release behavior is tied to polymer precipitation and degradation rate. The present example investigated addition of hydroxyapatite (HA) and drug-loaded poly(β-amino ester) (PBAE) microparticles to in situ forming poly(lactic-co-glycolic acid) (PLGA)-based systems to prolong release and reduce burst. PBAEs were synthesized, imbibed with simvastatin (osteogenic) or clodronate (anti-resorptive), and then ground into microparticles. Microparticles were mixed with or without HA into a PLGA solution, and the mixture was injected into buffer, leading to precipitation and creating solid scaffolds with embedded HA and PBAE microparticles. Simvastatin release was prolonged through 30 days, and burst release was reduced from 81% to 39% when loaded into PBAE microparticles. Clodronate burst was reduced from 49% to 32% after addition of HA filler, but release kinetics were unaffected after loading into PBAE microparticles. Scaffold dry mass remained unchanged through day 15, with a pronounced increase in degradation rate after day 30, while wet scaffolds experienced a mass increase through day 25 due to swelling. Porosity and pore size changed throughout degradation, likely due to a combination of swelling and degradation. The system offers improved release kinetics, multiple release profiles, and rapid solidification compared to traditional in situ forming implants.

Materials

PBAE Polymer Synthesis

PBAE macromer was synthesized by reacting diethylene glycol diacrylate and isobutylamine at a 1.2:1 diacrylate: amine molar ratio at 85° C. for 16 hours. Macromer was stored in an opaque vial under refrigeration until use. To create crosslinked hydrogels from macromer, 1 wt/wt % DMPA initiator dissolved in 50 wt/wt % ethanol was vortexed with macromer. The mixture was then pipetted between two glass plates with Teflon spacers, sealed and clamped, and then exposed to a UV flood source with an intensity of 12 mW/cm$^2$ for 5 minutes to form a crosslinked hydrogel slab. These PBAE polymer slabs were washed overnight in ethanol to remove unreacted monomer and initiator, and then stored in a desiccator to remain dry until use.

PBAE Particle Formation and Drug Loading

PBAE microparticles were formed by grinding dry PBAE slabs with a mortar and pestle, with HA added during the grinding process to coat particles and prevent aggregation. HA content was preliminarily tested at 66 w/w % and 75 w/w % weight ratios, and 75% (50 v/v %) was chosen due to ease of particle fabrication. PBAE particles were sieved to less than 250 μm, and larger particles were re-ground until all material was collected through the sieve. A Zeiss Evo MA 10 scanning electron microscope (SEM) (Carl Zeiss, Thornwood, N.Y.) at 4 kV accelerating voltage was used to visualize particle morphology, and a Quantax energy-dispersive x-ray spectroscopy (EDS) detector was used for elemental analysis. A series of 10 microscope images of HA and PBAE particles were analyzed using freely available ImageJ software to calculate mean particle size.

Simvastatin was either loaded into PBAE slabs prior to particle formation (pre-loaded) or loaded directly into PBAE microparticles (post-loaded), and each method was assessed for loading efficiency as well as the percentage of drug that was weakly bound to particle surface. FIG. 6A graphically represents the processing method for creating PBAE microparticles, as well as the differences between pre- and post-loaded particles. Post-loaded particles were prepared by dissolving simvastatin in ethanol at a concentration of 100 mg/mL and pipetting drug solution over particles at a ratio of 2 μL per mg of particles. This ratio allowed particles to swell without excess solution remaining, and expected drug loads were calculated under the assumption that all drug solution was imbibed by the microparticles. Particles were lyophilized overnight, briefly re-ground and sieved to break up aggregates, and stored in a vacuum chamber with desiccant. Pre-loaded microparticles were prepared by immersing PBAE slabs in simvastatin solution, allowing the hydrogel to swell for 24 hours, and then removing the hydrogel and lyophilizing overnight to evaporate ethanol. Drug-loaded PBAE slabs were ground with 75 wt % HA into particles and stored in a vacuum chamber with desiccant. Predicted values for drug loading using the pre-loading method were obtained by calculating swelling of PBAE in solution based on mass increase and assuming drug was homogeneously present in swollen hydrogels as well as surrounding solution. The density and concentration of the drug solution was then used to calculate expected drug loading based on mass change of the PBAE samples. Clodronate was loaded into separate batches of microparticles using an identical pre-loading technique with a 50 mg/mL clodronate solution in deionized water.

Measurement of Drug Loading into PBAE

Simvastatin loading into PBAE microparticles was measured by immersing drug-loaded particles in ethanol, vortexing, and allowing the particles to swell for 24 hours. The mixtures containing ethanol and swollen PBAE microparticles were then centrifuged, and supernatants were analyzed using HPLC to detect simvastatin, as described below. Clodronate loading was measured with an identical technique using 50% ethanol, and was detected by absorbance as described below. A mass balance indicated that all drug was successfully removed from the particles during 24 hours of immersion in ethanol for simvastatin or 50% ethanol solutions for clodronate, and subsequent immersions extracted no additional drug. Loading efficiency was defined as the ratio of the total mass of drug loaded into the particles to the initial mass of drug exposed to the particles.

In addition to loading efficiency, the percentage of drug present on the surface of particles was determined by washing drug-loaded particles with 5 mL ethanol over a filter to remove loosely surface-bound simvastatin or with 5 mL deionized water to remove loosely surface-bound clodronate. The remainder of drug present in the bulk of the microparticles was extracted by immersing particles for 24 hours in ethanol for simvastatin or 50% ethanol for clodronate. Drug detected in the initial wash was deemed loosely bound to the surface of particles, while drug detected after the 24 hour soak was determined to be imbibed into the bulk of the particles.

Formation of Injectable Scaffold System

PLGA was added to NMP and stirred overnight until fully dissolved to create a 20 wt/wt % PLGA solution. Simvastatin-loaded PBAE microparticles pre-loaded using 100 mg/mL simvastatin were added at 5 wt % and mixed homogeneously prior to injection. HA was also mixed homogeneously prior to injection to bring the final mixture to 30 wt % HA. Clodronate-loaded PBAE microparticles pre-loaded with 50 mg/mL clodronate were added using an identical technique. Samples without microparticles were prepared by freely mixing 1 wt % simvastatin or clodronate into 20% PLGA solution to simulate a traditional in situ forming PLGA system. FIG. 6B illustrates the differences between the proposed system and a traditional injectable system. Simvastatin and clodronate were measured as described below.

In Vitro Drug Release

The scaffold mixture was injected dropwise through a 16 gauge, blunt-tipped dispensing needle into PBS at 5% wt/vol. Upon contacting PBS, surface PLGA immediately began to precipitate, forming semi-spherical scaffolds approximately 3 mm in diameter that sank to the bottom of the vial. Samples were kept in an incubator at 37° C. on a plate shaker for the duration of the study. Supernatant was collected and replaced at each time point, and these samples were preserved at 4° C. until analysis. Clodronate release was measured for three loading conditions: freely mixed clodronate without HA filler, freely mixed clodronate with HA filler, and clodronate pre-loaded into PBAE microparticles with HA filler. Because PBAE microparticles were fabricated with HA as a dispersing agent, drug release from loaded particles was not investigated without HA filler. Simvastatin release was measured for three loading conditions: freely mixed simvastatin without HA filler, freely mixed simvastatin with HA filler, and simvastatin pre-loaded into PBAE microparticles with HA filler.

Measurement of Drug Concentrations

Simvastatin was measured on a Hitachi Primaide HPLC system equipped with a C18 column using a mobile phase composed of 70% acetonitrile and 30% water with 0.1% trifluoroacetic acid at a flow rate of 1 mL/min, and peaks were observed at 240 nm. Clodronate from collected supernatants were measured using a Powerwave HT (Biotek; Winooski, Vt., USA). In vitro release supernatant was pipetted into a UV-grade 96-well plate (Greiner Bio-One, Frickenhausen, Germany), and baseline absorbance was measured at 240 nm. On its own, clodronate does not exhibit a distinct absorption peak, so concentration was measured by mixing supernatant with a solution of 1.5 mM copper sulfate and 1.5 mM nitric acid at pH 2 to form a clodronate-copper complex that exhibits absorption at 240 nm. A pilot experiment confirmed that HA did not significantly interfere with clodronate readings in the working range.

Characterization of Release Kinetics

Drug release from polymeric systems is often analyzed using an adaptation of the Higuchi model by Peppas et al., widely known as the power law, to characterize release kinetics (Siepmann J, Peppas N A. Modeling of drug release from delivery systems based on hydroxypropyl methylcellulose (HPMC). Advanced Drug Delivery Reviews 2001; 48:139-57):

$$\frac{M_t}{M_\infty} = kt^n \quad (1)$$

Here, $M_t$ is the mass of drug at time t, M is the total mass of drug in the system, $$\frac{M_t}{M_\infty}$$

represents Tractional release or drug at time t, k is a constant encompassing scaffold and drug properties, and it is the release exponent used to characterize drug release. In the case of the spherical geometry (consistent with scaffolds formed via dropwise injection), n=0.43 corresponds to pure Fickian diffusion, n=0.85 corresponds to pure case II (polymer relaxation-based) transport, and values in between are combinations of the two, termed anomalous transport (Siepmann J, Peppas N A. Modeling of drug release from delivery systems based on hydroxypropyl methylcellulose (HPMC). Advanced Drug Delivery Reviews 2001; 48:139-57). Plots of $$\log \frac{M_t}{M_\infty}$$

versus log t were used to determine n for each drug. The power law is applicable when $$\frac{M_t}{M_\infty} < 0.6,$$

so release data were truncated to below 60% cumulative release when calculating n.

Mass Loss and Degradation

The injectable scaffold system was prepared as described previously, using unloaded microparticles. Non-destructive degradation analysis was performed on hydrated scaffolds in order to observe the mass change of wet samples. Scaffolds were injected dropwise into PBS and incubated at 37° C. on a shaker for 80 days. Initial injected mass was recorded for each scaffold. At intervals, scaffolds were removed from PBS, gently blotted dry, and weighed. Destructive analysis of dried samples was used to analyze scaffold dry mass change. Scaffolds were injected dropwise into PBS and incubated at 37° C. on a plate shaker until analysis. At each time point, scaffolds were lyophilized for 24 hours, and dry weight was measured. Lyophilized scaffolds were also scanned using a Scanco MicroCT 40 (Scanco Medical, Switzerland) at 55 kV and 145 mA with 6 µm voxel size. The built in bone trabecular morphometry tool was used to create 3D reconstructions to visualize microarchitecture and quantify porosity and pore size at various time points during the degradation process.

Statistical Analysis

All data are presented as mean±standard deviation. Release data were analyzed in JMP 10 software, using one-way analysis of variance (ANOVA) to determine differences between release curves followed by Tukey-Kramer mean comparison tests as necessary. Comparisons between individual pairs of samples for loading efficiencies were performed using a student's two-tailed t-test. Differences were considered significant for $p<0.05$.

Results

Drug Loading into PBAE Particles.

Figure 7:
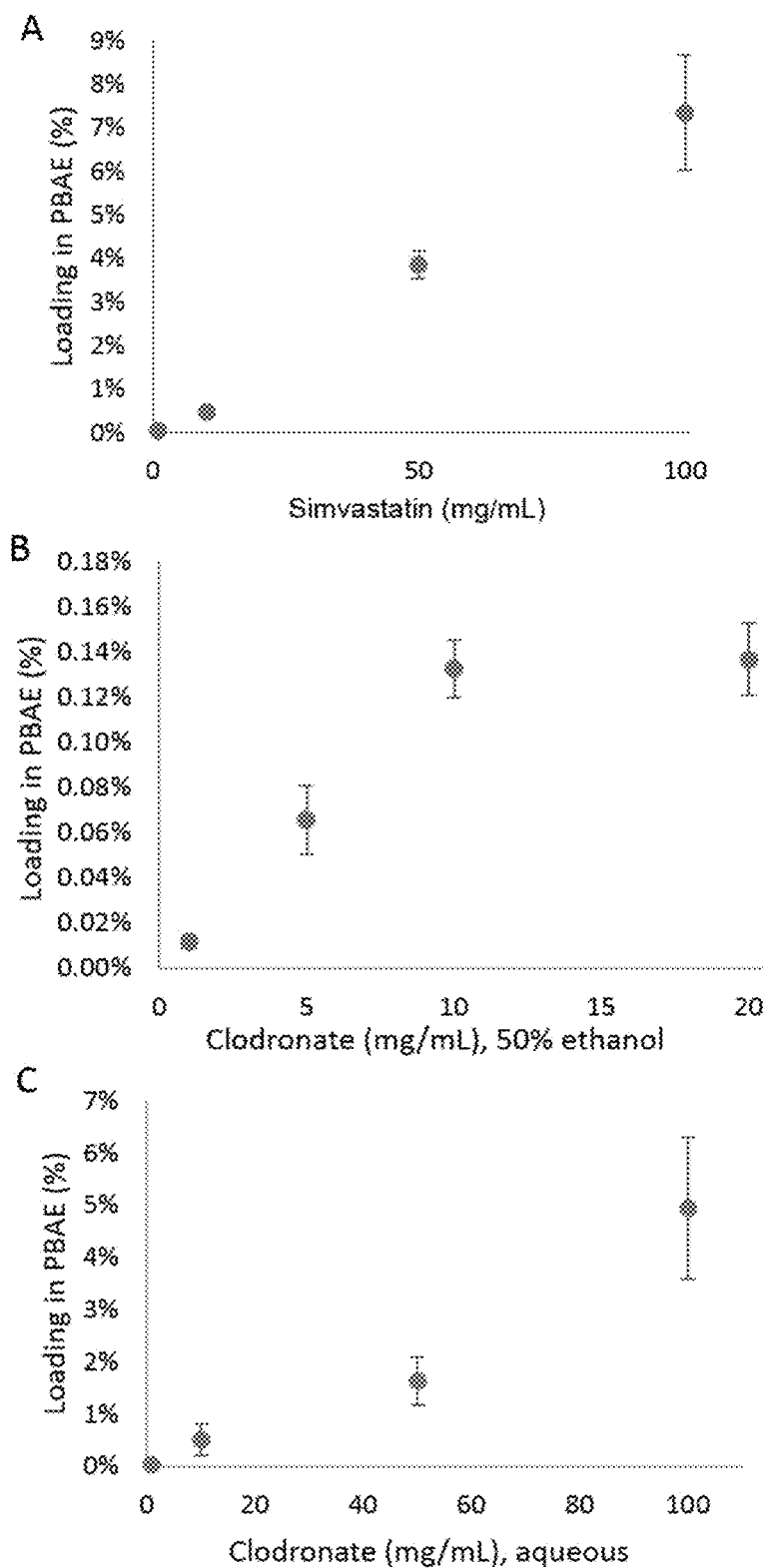
FIG. 7 shows drug loading into PBAE hydrogel. A) Simvastatin loading after soaking in 100% ethanol solutions for 24 hours. B) Loading after soaking in 50% ethanol clodronate solution for 24 hours. C) Loading after immersion in aqueous clodronate solution for 24 hours. Data are mean±standard deviation (n=3).

Drug loading into PBAE increased linearly with drug solution concentration for simvastatin (FIG. 7A) and clodronate (FIGS. 7B and 7C). Clodronate became insoluble at 20 mg/mL in 50% ethanol, while the drug remained soluble through 100 mg/mL in DI water. At 100 mg/mL clodronate, however, it was observed that hydrogel would swell to a greater degree and fracture upon handling, leading to high variability between samples (FIG. 7C), so 50 mg/mL clodronate in DI water was used for future experiments. Simvastatin was loaded into gels or particles using a 100 mg/mL solution in 100% ethanol.

HA possessed a mean particle diameter of 10 µm, while the PBAE particles produced by grinding PBAE hydrogels together with HA had a mean diameter of 68 µm. PBAE microparticles exhibited a composite structure consisting of spherical particles consistent with HA sizes embedded in an amorphous material consistent with the hydrogel nature of PBAE (FIG. 8A). The spherical HA particles exhibited a rough, granular surface morphology, compared to the smooth PBAE component. EDS elemental mapping showed calcium and phosphorous localized to the spherical particles (FIG. 8B). Point analysis of presumed HA and PBAE regions indicated higher calcium and phosphorous levels in spherical HA particles, and higher carbon and oxygen content in the PBAE region (FIG. 8C). When these microparticles were immersed in a mixture of 20% PLGA solution in NMP with 30 wt % HA added to simulate pre-injection conditions, they underwent a 47% mass increase due to swelling (FIG. 8D), with a 28% increase occurring within 5 minutes.

Figure 9:
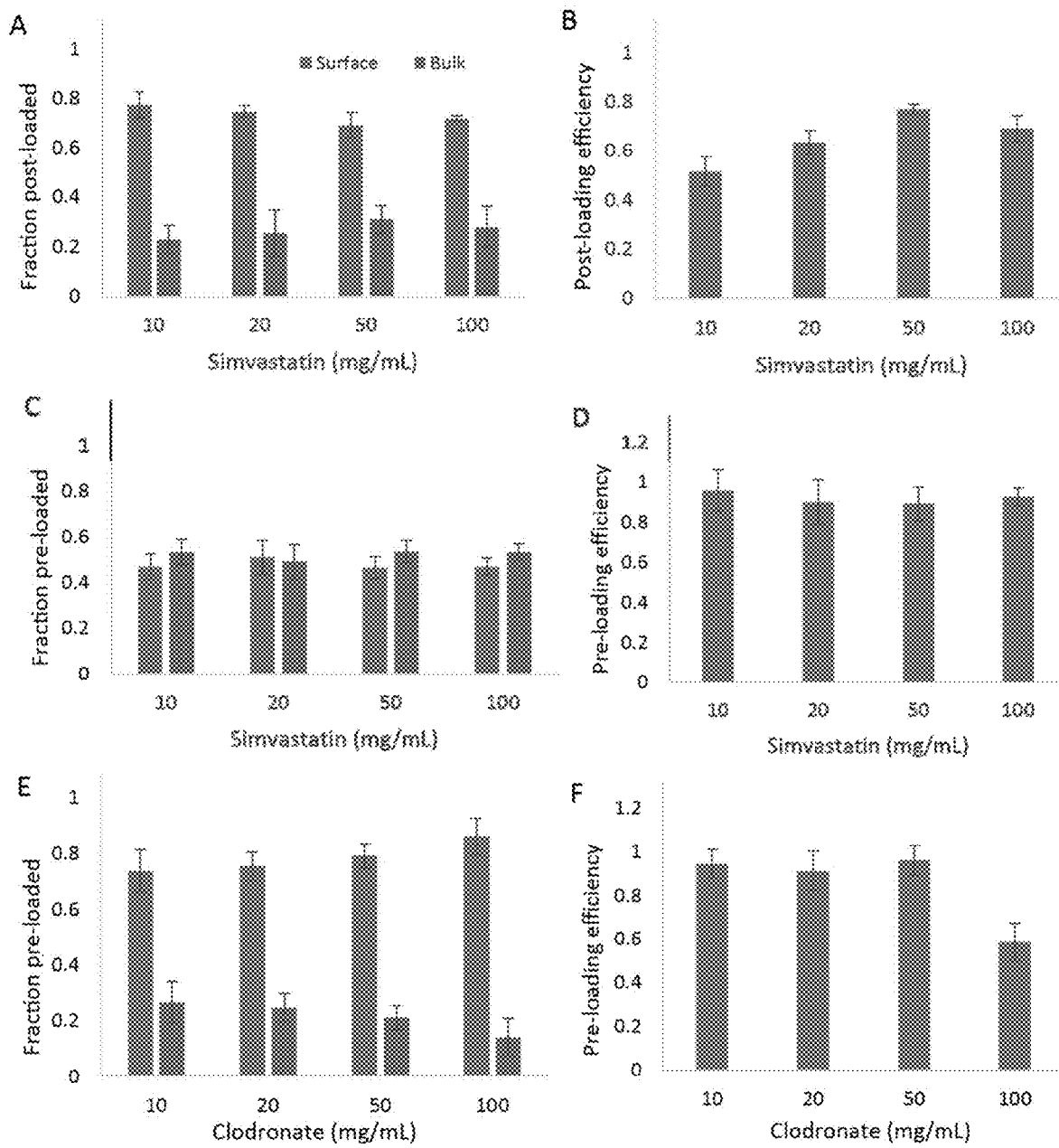
FIG. 9 shows surface vs. bulk loading in microparticles: A) simvastatin post-loaded, C) simvastatin pre-loaded, and E) clodronate pre-loaded. Loading efficiency: B) post-loaded simvastatin, D) pre-loaded simvastatin, and F) pre-loaded clodronate. Data are mean±standard deviation (n=3).

Efficiency of incorporating simvastatin into post-loaded particles ranged from 52% to 77% (FIG. 9B), and efficiency ranged from 89% to 96% in pre-loaded particles (FIG. 9D). A surface wash indicated that between 69% and 77% of simvastatin was loosely surface-bound to post-loaded particles, with no differences between simvastatin concentrations (FIG. 9C). Using the pre-loading technique, a significantly lower amount (p<0.05), between 46% and 51% of simvastatin, was loosely surface-bound, again with no concentration dependence (FIG. 9A). Pre-loaded clodronate yielded particles with 74% to 86% of drug loosely surface-bound (FIG. 9E). Clodronate loading efficiency ranged from 91% to 97% at concentrations up to 50 mg/mL, and dropped to 59% at 100 mg/mL.

In Vitro Release

Figure 10:
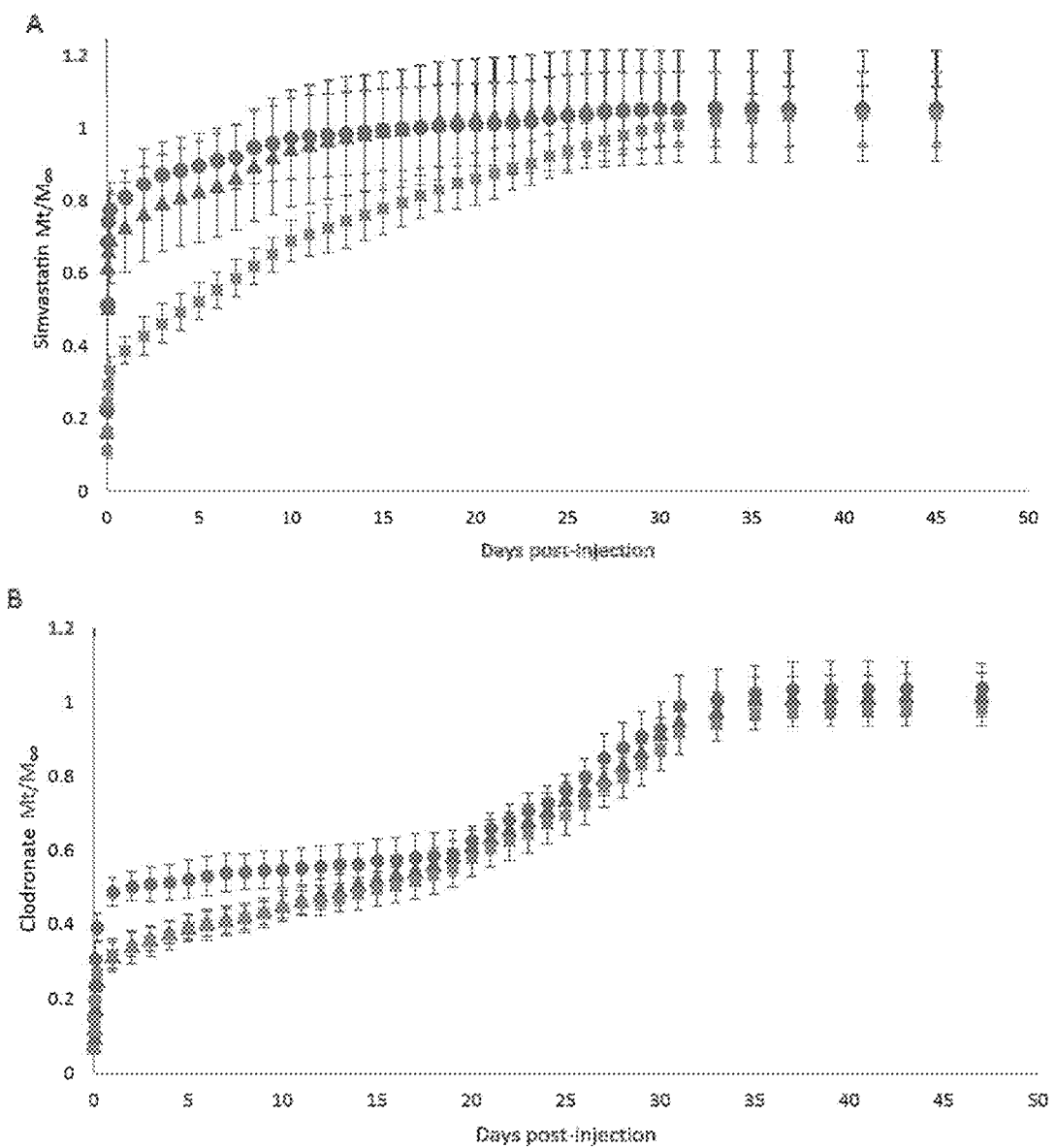
FIG. 10 shows cumulative release profiles. A) Release of simvastatin loaded freely into the PLGA solution with (Δ) or without HA (○), or loaded into PBAE (□) (n=3). B) Release of clodronate freely loaded into PLGA solution with (Δ) or without HA (○), or loaded into PBAE microparticles (□) (n=4). Data are mean±standard deviation.

Freely mixed simvastatin was 81% released within 1 day and 95% released within 10 days, with no difference between scaffolds prepared with or without HA (FIG. 10A). In both cases, there was a gradual decrease in release rate as fractional release ($M_t/M_\infty$) reached 100%. Pre-loaded simvastatin microparticles mixed into the system reduced the 1 day burst to 39% (p<0.05), followed by sustained release of 1.3%/day for 30 days. The sustained release from day 1 through day 30 was roughly linear, with no appreciable decrease in rate until completion of drug release.

Freely mixed clodronate prepared without HA exhibited a 49% burst within one day of release, while both freely mixed and pre-loaded clodronate prepared with HA produced 32% burst (p<0.05) (FIG. 10B). Freely mixed clodronate without HA gradually released at a rate of 0.6%/day through day 19, while clodronate mixed with HA or pre-loaded into microparticles released at 1.3%/day through day 19. By day 20, there was no difference in total clodronate release between each curve. All clodronate release curves showed a distinct increase in release rate to 3%/day at day 20 that continued through day 31, after which nearly all drug was released.

To characterize release kinetics, plots of $$\log \frac{M_t}{M_\infty}$$

vs log t were used to calculate n for pre-loaded simvastatin and clodronate through the first day of release. After the first day, release rates tended to be linear and were therefore expressed as a daily release rate. For initial release during the burst, simvastatin and clodronate release exhibited n=0.47 and n=0.49, respectively.

Mass Loss and Degradation

Lyophilized scaffolds exhibited an initial mass loss of 50% in the first hour, followed by an additional gradual decrease of 5% over the first day (FIG. 11A). Mass fraction remained unchanged at approximately 45% for 15 days, followed by a linear decrease in mass at a rate of 0.2%/day until day 50. Mass fraction did not change significantly after day 50, ranging from 25% to 29% through day 80. Lyophilized samples collected at day 40 and beyond were primarily powder that crumbled upon handling.

Non-destructive mass change of wet scaffolds showed an initial 12% decrease in mass over the first day, followed by a linear increase of 1.4%/day over the next 14 days (FIG. 11B). At day 15, mass fraction became more variable as some samples began to decrease in mass, while others swelled through day 30. Linear mass loss was observed from day 30 through day 55, when the remaining mass fraction stabilized at 20% until day 80.

Figure 12:
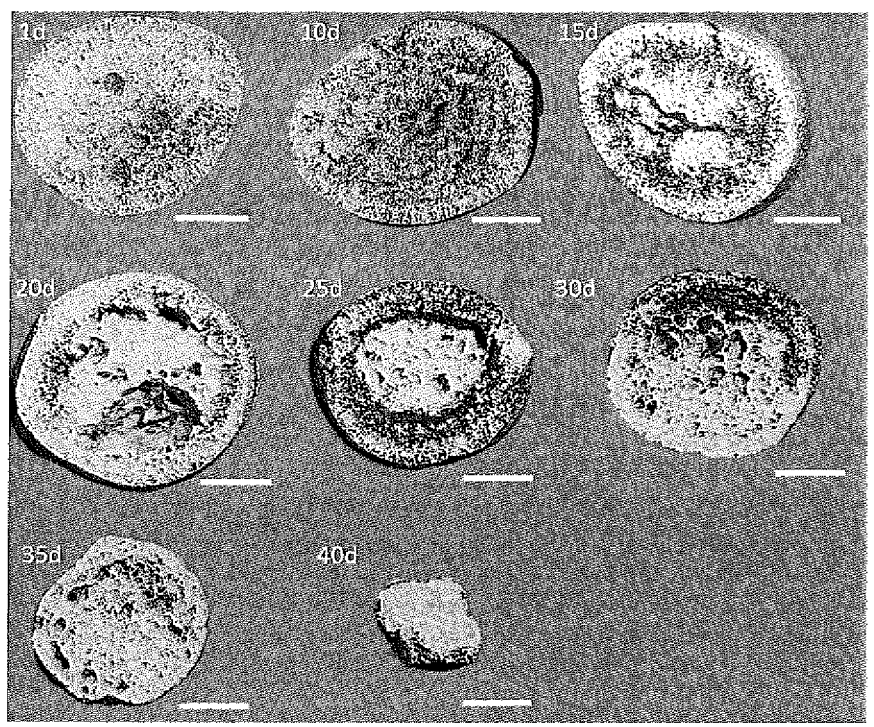
FIG. 12 shows representative microCT cut-plane images of lyophilized scaffolds showing internal microarchitecture throughout the degradation process. Scale bars are 1 mm.
Figure 13:
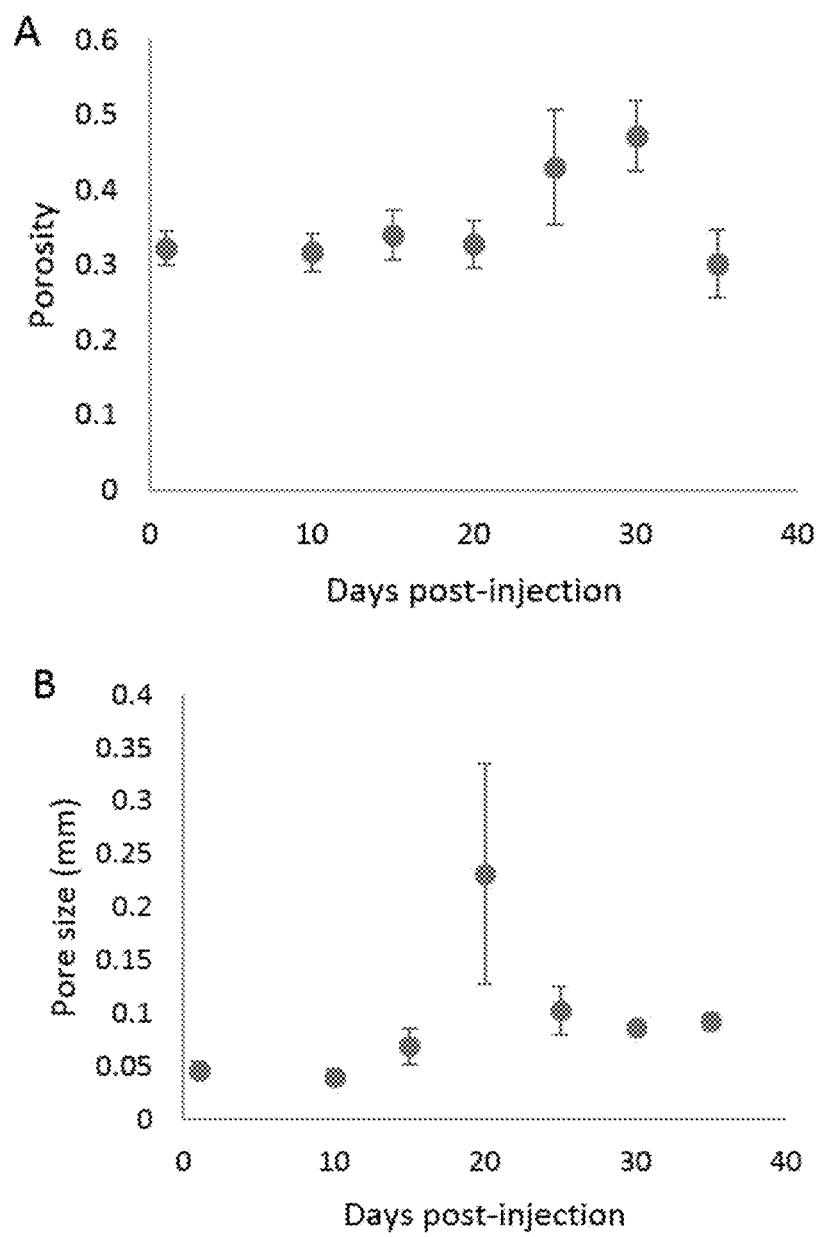
FIG. 13 shows morphometric parameters during degradation. A) Porosity and B) average pore size measured by microCT evaluation of samples through 35 days.

Qualitative assessment of microCT cutplanes roughly bisecting samples revealed a uniformly porous microstructure through day 10 (FIG. 12). By day 15, denser regions had developed in the middle and at the edges of scaffolds. By day 20, large macropores were present in the core of the scaffolds. At day 25, scaffold cores appeared more uniformly porous, and the denser regions near the edges of scaffolds had become more porous. The dense regions appeared to migrate towards one side of the scaffold by day 30, and by day 35, scaffolds had significantly decreased in size, leaving behind a uniformly porous pellet. After day 35, scaffolds were too fragile to handle, and a representative sample of residual material collected at day 40 was nonporous. MicroCT morphometry revealed an increase in porosity from 31% through day 20 to 47% by day 30, followed by a return to 30% at day 35 (FIG. 13A). Average pore size ranged from 40 to 100 μm, except for samples at day 25, which had average pore size of 231 μm (FIG. 13B).

Discussion

PBAE microparticles were successfully formed by co-grinding PBAE hydrogels with HA, forming individual PBAE particles coated with multiple, smaller HA particles. Elemental analysis confirmed that the smaller, spherical coating consisted of HA, and the underlying particles were hydrogel. Simvastatin pre-loaded into PBAE hydrogels showed both higher loading efficiency and bulk imbibition of drug, which are favorable conditions to prolong drug release relative to freely mixed drug. Swelling data were found to be an accurate predictor of drug loading into gels at various concentrations, consistent with previous drug loading results with hydrogels (Kim S, Bae Y, Okano T. Hydrogels: Swelling, Drug Loading, and Release. Pharmaceutical Research 1992; 9:283-90). It was determined that processing of particles does not appreciably affect simvastatin loading efficiency using the pre-loading technique while still providing favorable imbibition ratios of surface to bulk drug. A decrease in loading efficiency as well as a higher percentage of simvastatin present loosely bound to the surface of particles using a post-loading technique may be attributable to the free HA powder used to coat the PBAE particles absorbing a percentage of drug solution, preventing its complete penetration into the hydrogel and resulting in a majority of drug sequestered outside the hydrogel microparticles. The high levels of surface drug seen for clodronate pre-loading may be due to the fact that the PBAE used in these experiments swells to a significantly larger degree in ethanol than in water (data not shown), allowing less penetration of drug into the bulk of the gels. Additionally, clodronate was more favorably loaded into PBAEs in aqueous solutions rather than 50% ethanol solutions because its solubility was limited. The swelling kinetics of PBAEs in the injection mixture (30 wt % HA in 20% PLGA solution) suggest that particles swell appreciably due to NMP exposure prior to injection, but the magnitude of swelling is negligible compared to the amount observed in pure NMP (47% at equilibrium vs. 470% in pure NMP). This difference is due to the presence of PLGA, which dissolves readily in NMP (Lambert W J, Peck K D. Development of an in situ forming biodegradable poly-lactide-coglycolide system for the controlled release of proteins. Journal of Controlled Release 1995; 33:189-95) and prevents hydrogels from fully swelling as they would in pure NMP. Additionally, the particles may be immersed in PLGA solution for only a matter of minutes before injection, so realistically, particles may swell by only 23% if the system is injected 5 minutes after addition of microparticles to the PLGA solution.

Simvastatin release was strongly affected by its loading state. A comparison of release kinetics between injectable systems loaded with freely mixed simvastatin and simvastatin-loaded PBAE microparticles indicated that burst release can be significantly reduced and duration of release can be significantly extended by loading simvastatin into PBAE microparticles. Because simvastatin is soluble in NMP, freely mixed drug presumably was dissolved in NMP and the majority of it exited into the aqueous phase during the solvent exchange process, resulting in a large burst release. The residual 20% of simvastatin was released in a sustained manner over the next 10 days, similar to previous work on such systems using freely mixed drug (Tang Y, Singh J. Controlled delivery of aspirin: effect of aspirin on polymer degradation and in vitro release from PLGA based phase sensitive systems. International Journal of Pharmaceutics 2008; 357:119-25; Bakhshi R, Vasheghani-Farahani E, Mobedi H, Jamshidi A, Khakpour M. The effect of additives on naltrexone hydrochloride release and solvent removal rate from an injectable in situ forming PLGA implant. Polymers for Advanced Technologies 2006; 17:354-9). PBAE microparticles experience some swelling in the NMP-PLGA solution during the mixing stage prior to injection, but burst is attenuated for pre-loaded PBAE microparticles. The 39% burst release through day 1 using pre-loaded particles may be attributable to loosely surface-bound simvastatin that was likely dissolved by NMP and released during solvent exchange, similarly to freely-mixed simvastatin. Because simvastatin was loaded into PBAE with high efficiency, the release kinetics are likely a combination of the swelling, degradation, and diffusion of drug through the PBAE material as well as the PLGA phase.

Clodronate release appeared to be unaffected by loading state of the drug in PBAE microparticles, but it was instead dependent on the presence of HA in the injection mixture. This can be attributed to the formation of a complex between the bisphosphonate drug and hydroxyapatite, specifically between the two phosphonate groups of clodronate and the divalent calcium cations present in HA crystals (Nancollas G H, Tang R, Phipps R J, Henneman Z, Guide S, Wu W, et al. Novel insights into actions of bisphosphonates on bone: differences in interactions with hydroxyapatite. Bone 2006; 38:617-27). Freely mixed clodronate without HA filler was 49% released within 1 day, compared to 32% for both compositions with HA. Because clodronate is insoluble in NMP, this initial burst is likely due to free clodronate suspended in the PLGA solution being dissolved by water during solvent exchange. The increase in release rate observed around day 20 corresponded to the maximum swelling state of scaffolds, indicating that scaffolds had begun to appreciably degrade and more water could enter the system to promote more rapid clodronate dissolution. Samples prepared with HA had a lower burst and higher release rate between days 1 and 20 due to the clodronate being initially retained in the system by complexation, after which the drug was released diffusively from the solidified system. Clodronate release kinetics are consistent with the classic three-stage release profiles observed in rapidly-precipitating systems, in which an initial burst is followed by slow diffusion, and then a more rapid swelling- or degradation-mediated release occurs (Fredenberg S, Wahlgren M, Reslow M, Axelsson A. The mechanisms of drug release in polylactic-co-glycolic acid)-based drug delivery systems—A review. International Journal of Pharmaceutics 2011; 415:34-52). Interestingly, the slow diffusion stage was accelerated by the addition of HA, likely because the larger amount of drug retained in the scaffold provided a higher concentration gradient to drive diffusion.

The rapid precipitation implied by the initial burst of clodronate and simvastatin as well as the early mass loss is indicative of rapid NMP exchange, which demonstrates the potential of the system for rapid solidification. Fast precipitation is favorable for quick delivery of NMP for an initial osteogenic stimulus, and rapid formation of a solid drug delivery depot may have advantages over gradually precipitating systems with persistent gel or liquid cores for days or weeks after injection due to NMP retention (Bakhshi R, Vasheghani-Farahani F, Mobedi H, Jamshidi A, Khakpour M. The effect of additives on naltrexone hydrochloride release and solvent removal rate from an injectable in situ forming PLGA implant. Polymers for Advanced Technologies 2006; 17:354-9). Specifically, this has implications for intraosseous injection, where the system can completely precipitate within days while continuing to release drug over a period of weeks to months. In systems with freely suspended or dissolved drug, precipitation rate strongly influences burst release (Graham P D, Brodbeck K J, McHugh A J. Phase inversion dynamics of PLGA solutions related to drug delivery. Journal of Controlled Release 1999; 58:233-45; Yewey G L, Duysen E G, Cox S M, Dunn R L. Delivery of proteins from a controlled release injectable implant. Pharmaceutical biotechnology 1997; 10:93-117), and the addition of drug-loaded PBAE microparticles can allow for prolonged release and decreased burst without prolonging precipitation of the system. The rapid precipitation may also allow filler particles, such as hydroxyapatite, to provide mechanical support in future iterations of the system. After the initial burst, pre-loaded simvastatin exhibited prolonged delivery over the entire 30 day period. The lack of change in simvastatin release kinetics upon addition of 30 wt % HA was expected, because HA should not appreciably interact with statins, which lack the phosphonate groups that provide binding sites for the calcium in HA. The successful demonstration of sustained release of both hydrophilic and hydrophobic small molecule drugs with reduced burst from this system shows promise for new applications of in situ forming PLGA systems where rapid precipitation is required.

By fitting the power law to initial drug release, the release exponent n can be used to classify the mechanism of drug release from the system. For simvastatin, n of 0.47 indicates primarily Fickian diffusion based on the standard n values for a spherical scaffold of n=0.43 for pure Fickian diffusion and n=0.85 for pure Case II transport. The slightly higher release exponent compared to the pure Fickian value can be attributed to several factors, including the swelling of the PBAE hydrogel microparticles and minor swelling of the surrounding PLGA matrix. Similarly, n of 0.49 for clodronate corresponds to primarily Fickian diffusion as well. Both clodronate and simvastatin are therefore released via diffusive mechanisms prior to their sustained release, which follows a more linear trend. This data supports the idea that the burst was composed of a fraction of the loaded drug dissolved or suspended in NMP, and the rapid solvent exchange was likely responsible for the initial release. The sustained release was likely a combination of diffusion, erosion, and swelling-based mechanisms, and the superposition of these mechanisms produces release curves that are most simply expressed in daily release rates. Because simvastatin is almost insoluble in water but highly soluble in NMP, the larger burst compared to clodronate is unsurprising, as dissolved simvastatin may be transported out of the scaffold during the solvent exchange phase. Future iterations of the system may be able to further reduce burst by reducing access of drug to the NMP phase to limit the initial diffusive component of the system.

PLGA is a bulk-eroding material that degrades via hydrolysis of ester bonds, resulting in a progressive decrease in molecular weight until monomeric or oligomeric species of sufficiently low molecular weight are generated and cleared when molecular weight drops to approximately 1.5 kDa (von Burkersroda F, Schedl L, Gopferich A. Why degradable polymers undergo surface erosion or bulk erosion. Biomaterials 2002; 23:4221-31; Kenley R A, Lee M O, Mahoney T R, Sanders L M. Poly(lactide-co-glycolide) decomposition kinetics in vivo and in vitro. Macromolecules 1987; 20:2398-403). The in situ forming scaffold has the additional property of a rapid precipitation event upon injection, and due to the high aqueous miscibility of NMP, a rapid initial dry mass loss was observed within the first hour following injection as NMP entered the aqueous phase and the highly hydrophobic PLGA precipitated. By 24 hours, 46% dry mass remained, corresponding to the loss of the majority of the NMP content that composed 54 wt % of the system. The subsequent lack of dry mass change suggests that hydrolytic degradation was unable to produce small enough molecular weight species to be cleared into the surrounding aqueous environment until day 15. After day 15, the linear decrease in dry mass corresponded to clearance of degradation byproducts until all PLGA was removed from the system. The remaining 29% dry mass can be attributed to remaining HA content that composed 30% of the original mass. For wet scaffolds, the initial 12% decrease in wet mass throughout the first day of degradation supports the replacement of NMP with water due to precipitation of PLGA. The 20% increase in wet mass over the following 14 days indicates swelling of the PLGA matrix. Following this brief swelling, individual sample behavior diverged as swelling reached a maximum between 110-120% between days 20-30. The linear decrease in mass was delayed compared to dry samples because the small losses in polymer degradation byproducts were offset by increased water content as the system swelled. The lack of mass change beyond day 55 was consistent with the complete clearance of PLGA observed in dry mass studies, and the lower mass fraction remaining (20% compared to 29%) was likely due to repeated handling of samples during nondestructive measurements resulting in small amounts of HA being resuspended and removed with supernatant at each time point.

Based on microCT images, it was evident that scaffold microarchitecture underwent dramatic changes throughout the degradation process. The first indicator of change was the development of denser regions in the core and near the edges of scaffold by day 15, which may be attributable to the cessation of NMP release and the hydrophobicity of PLGA causing solid regions to condense together. At day 20, the highest pore size was observed as large, closed macropores. This phenomenon corresponds to the scaffolds at their maximum swelling state based on wet mass, and was accompanied by further densification of the core and edge regions. At day 25, the core remained dense, but macropores were no longer evident, and the edges of scaffolds were less dense and more porous, which is consistent with reports of PLGA of this molecular weight beginning to lose mass to clearance after 3 weeks (Kenley R A, Lee M O, Mahoney T R, Sanders L M. Poly(lactide-co-glycolide) decomposition kinetics in vivo and in vitro. Macromolecules 1987; 20:2398-403). At day 30, it is possible that enough polymer had been lost to allow mobility of HA content through the PLGA, which settled at the bottom of scaffolds during incubation. By day 35, scaffold density and pore distribution appeared more uniform, and scaffolds were noticeably smaller in size due to further degradation of the highly porous regions seen at day 30.

In situ forming PLGA systems have been popularized due to their ease of use and unique ability to solidify at the point of injection, forming a drug delivery depot in the tissue of interest. However, because drug release from these systems is highly dependent on solvent exchange and polymer chemistry (Graham P D, Brodbeck K J, McHugh A J. Phase inversion dynamics of PLGA solutions related to drug delivery. Journal of Controlled Release 1999; 58:233-45), release of multiple agents with unique release profiles is challenging. Additionally, low molecular weight drugs tend to exit during the solvent exchange, resulting in high initial burst (Parent M, Nouvel C, Koerber M, Sapin A, Maincent P, Boudier A. PLGA in situ implants formed by phase inversion: Critical physicochemical parameters to modulate drug release. Journal of Controlled Release 2013; 172:292-304). Multiple drug release platforms for small molecule drugs, therefore, tend to be pre-formed scaffolds or injectable suspensions of micro- or nanoparticles (Biondi M, Ungaro F, Quaglia F, Netti P A. Controlled drug delivery in tissue engineering. Advanced Drug Delivery Reviews 2008; 60:229-42; Zhang L, Radovic-Moreno A F, Alexis F, Gu F X, Basto P A, Bagalkot V, et al. Co-Delivery of Hydrophobic and Hydrophilic Drugs from Nanoparticle-Aptamer Bioconjugates. ChemMedChem 2007; 2:1268-71; Sokolsky-Papkov M, Agashi K, Olaye A, Shakesheff K, Domb A J. Polymer carriers for drug delivery in tissue engineering. Advanced Drug Delivery Reviews 2007; 59:187-206; Zhou T, Lewis H, Foster R E, Schwendeman S P. Development of a multiple-drug delivery implant for intraocular management of proliferative vitreoretinopathy. Journal of Controlled Release 1998; 55:281-95). The addition of PBAE microparticles to the in situ forming PLGA system combines the ease of use of injectable systems, the controlled release of microparticle systems, and the spatial control of solid scaffolds. Even in a rapidly-solidifying system, PBAE microparticles are capable of prolonging release of both hydrophilic and hydrophobic drugs over a 30 day period with significantly less burst than traditional injectable PLGA systems using freely mixed drug.

Conclusions

An in situ hardening, PLGA-based system offers a unique drug delivery platform due to its injectability and space-filling properties, and the addition of drug-loaded microparticles introduces the possibility for tunable release profiles for multiple pharmaceutical agents. In addition to the potential for multiple release profiles, the addition of drug-loaded PBAE microparticles enables the sustained release of water-soluble, small molecule drugs, such as clodronate, as well as lipophilic drugs, such as simvastatin, independent of PLGA precipitation. The biodegradability of the system makes this a favorable candidate for applications where a secondary surgery to remove the depleted scaffold is undesirable or impossible. Release kinetics can be multiphasic simply by loading drug freely into the PLGA solution for burst release, or into PBAE microparticles for sustained release with reduced burst. This injectable scaffold provides the simplicity of a targeted injection with the utility of an implantable drug delivery scaffold without compromising desirable release kinetics.

Example 2

In situ forming scaffolds containing hydroxyapatite micro- and nanoparticles were characterized to determine their mechanical properties, injectability, and microarchitecture. Scaffolds were prepared with various concentrations of hydroxyapatite, as well as poly($\beta$-amino ester) microparticles that facilitate drug delivery. Strength was increased three-fold, from 2 to 6 MPa, while compressive modulus was improved 6-fold, from 24 to 141 MPa, via the addition of 30% nano-hydroxyapatite, which provided greater benefits at equivalent concentrations compared to micro-hydroxyapatite. Scaffolds retained a uniformly porous microarchitecture, and hydroxyapatite particles were distributed evenly throughout the PLGA phase. Injectability, determined by the force required to inject 0.5 mL of material within 60 seconds, remained clinically acceptable at <50 N at 30% w/w hydroxyapatite and up to 10% w/w PBAE microparticles. Ex vivo injections into intact porcine femoral heads increased compressive modulus of trabecular bone from 81 to 180 MPa and strength from 3.5 to 5.9 MPa. This injectable scaffold offers mechanical reinforcement coupled with previously demonstrated drug delivery potential in a single injection for bone-weakening conditions, such as osteonecrosis or osteoporosis.

Synthesis of PBAE Microparticles

PBAE hydrogel slabs were synthesized as described previously (Anderson D G, Tweedie C A, Hossain N, Navarro S M, Brey D M, Van Vliet K J, Langer R, Burdick J A. A Combinatorial Library of Photocrosslinkable and Degradable Materials. Advanced Materials 2006; 18(19):2614-2618; Hawkins A M, Milbrandt T A, Puleo D A, Hilt J Z. Synthesis and analysis of degradation, mechanical and toxicity properties of poly(β-amino ester) degradable hydrogels. Acta Biomaterialia 2011; 7(5):1956-1964). Briefly, macromer was created by reacting diethylene glycol diacrylate with isobutylamine at 85° C. for 16 hours at a 1.2:1 molar ratio. This macromer was then photopolymerized between two glass plates with 1% w/w DMPA initiator and a 1:1 weight ratio of macromer to microparticulate hydroxyapatite (MHA) (Sigma-Aldrich, St. Louis, Mo., USA) to form a PBAE hydrogel slab. PBAE hydrogels were previously loaded with drug for use as delivery vehicles, but were left unloaded for these experiments. Microparticles were formed by grinding PBAE slabs and sieving until all collected particles were 250 μm or less in size.

NHA Synthesis

Nanoparticulate HA (NHA; nGimat, Lexington, Ky., USA) was produced at nGimat LLC's facility in Lexington, Ky., using a solution combustion process called NanoSpray Combustion$^{SM}$. This scalable process is capable of producing synthetic bone minerals, such as HA, tricalcium phosphate (TCP), and amorphous calcium phosphate (ACP), using cost-effective precursor materials. To produce NHA, a calcium carboxylate precursor and an alkyl phosphate precursor of appropriate proportions were dissolved in an organic solvent system, the solution was converted to an ultrafine spray (referred to as a NanoSpray) using a device called a Nanomiser®, and the spray was combusted under a controlled atmosphere. The average particle size for the NHA was <200 nm, as estimated by BET. X-ray diffraction confirmed the presence of the HA phase ($Ca_5(OH)(PO_4)_3$), and X-ray fluorescence spectroscopy showed that the Ca:P ratio was close to 5:3.

Formation of Cylindrical Scaffolds

PLGA (50:50 L:G, acid terminated, inherent viscosity 0.55-0.75 dL/g) was obtained from DURECT, Inc. (Birmingham, Ala., USA). All experiments used a polymer solution of 30% w/w PLGA in NMP (Sigma-Aldrich, St. Louis, Mo., USA). PBAE microparticles and MHA or NHA were mixed homogeneously into the polymer solution using a spatula. The scaffold mixture was loaded into a syringe and injected through a 16 gauge needle into a cylindrical agarose mold, where the system was allowed to solidify in phosphate-buffered saline (PBS). Scaffolds contained different concentrations of MHA or NHA, ranging from 0% to 50% w/w. All scaffolds contained 5% w/w PBAE microparticles to mimic prior drug release study conditions, unless otherwise indicated. PBS was replaced daily to prevent accumulation of NMP or low molecular weight species that were cleared from the scaffolds.

Mechanical Properties of Cylindrical Scaffolds

All compression tests were performed using a Bose ELF 3300 mechanical testing instrument. Modulus was calculated as the slope of the initial linear region of the stress-strain curve (approximately the first 5-10% strain). Yield stress was determined as the stress at which the stress-strain curve became nonlinear. To first identify any strain rate-dependence of mechanical properties, scaffolds prepared with increasing MHA content were tested in unconstrained compression to 50% strain at displacement rates of 0.006, 0.06, and 0.6 mm/s (strain rates of 0.001, 0.01, and 0.01 s$^{-1}$, respectively). The contribution of PBAE microparticles to mechanical properties was quantified by increasing PBAE content from 1% to 15% w/w in scaffolds prepared with 30% NHA.

To determine the effects of NHA versus MHA on scaffold properties, a comparison of mechanical properties for scaffolds containing different amounts of MHA and NHA was performed at a displacement rate of 1 mm/min (0.0167 mm/s, or a strain rate of 0.0028 s$^{-1}$) to 50% strain. Total HA content ranged from 0 to 50% in intervals of 10%. Scaffolds were prepared with either pure MHA, pure NHA, or different ratios of the two.

Injectability

To quantify injectability, scaffold mixtures containing 30% w/w NHA and 5, 10, or 15% w/w PBAE microparticles were loaded into a 3 mL syringe affixed with a 1.5 inch, 16 gauge needle. The loaded syringe was suspended by its flanges in a 15 mL centrifuge tube to collect the injected mixture, with the end of the tube in contact with the load cell and the plunger of the syringe in contact with the axial mover. The plunger was subjected to a series of sustained loads to simulate injection force, and the resulting displacement of the plunger was recorded. Injectability was quantified by plotting the time to inject 0.5 mL as a function of the injection force. Rational limits of 60 second injection time and 50 N injection force were set as the limits of injectability based on consultation with an orthopedic surgeon.

Microarchitecture

Effects of HA on microarchitecture were analyzed by preparing scaffolds with increasing NHA and MHA content, as well as a variety of NHA/MHA mixtures totaling 30% HA, lyophilizing these scaffolds after they had solidified in PBS for 3 days, and then scanning them with a SCANCO MicroCT 40 (SCANCO Medical AG, Switzerland) at 55 kV and 145 mA and 6 μm voxel size. Microarchitecture was quantified by porosity and material density. Scanning electron microscopy (SEM) was used to visualize micro- and nanoarchitecture of scaffolds containing 30% w/w NHA. Samples were freeze-fractured, coated with gold-palladium alloy, and imaged with a Hitachi S-4300 scanning electron microscope at 3 kV accelerating voltage.

Ex Vivo Scaffold Injections

Humeral heads were harvested from 10 week old male piglets euthanized in a separate study, and were kept frozen until use, without chemical fixation or removal of marrow. Using a 16-gauge, 2.5-inch bone biopsy needle inserted through the growth plate into the proximal humeral epiphysis, two humeral heads each received 3 mL ex vivo injections of 30% NHA/5% PBAE scaffolds. Two humeral heads were used as untreated controls. All humeral heads were scanned using microCT prior to injection, immersed in PBS for 5 days to allow scaffolds to fully solidify, and then scanned again to quantify scaffold infiltration. After 5 days in PBS, a 3 mm diameter cylindrical punch was used to remove tissue samples in the mediolateral direction, with the punch approaching through the articular cartilage and penetrating through the growth plate, for a total of 7 samples each for treatment and control groups. These cylindrical samples were trimmed to 6 mm in length, using only trabecular bone tissue between the growth plate and the articular cartilage. All samples were stored in PBS and tested the same day in unconstrained compression at a rate of 1 mm/min.

Results

Strain Rate and MHA Content

Scaffolds prepared with different MHA contents were compressed at strain rates spanning three orders of magnitude. At strain rates of 0.001, 0.01, and 0.1 $s^{-1}$ (corresponding to displacement rates of 0.006, 0.06, and 0.6 mm/s), modulus increased with MHA content (FIG. 1A). The highest modulus increased from 64 to 82 to 96 MPa for each respective strain rate, and overall, moduli ranged from 9 to 96 MPa. The lowest recorded modulus for any scaffold containing HA was 29 MPa (10% MHA, 0.001 $s^{-1}$), while scaffolds without any HA ranged from 9 to 30 MPa, increasing with strain rate. At 0.001 $s^{-1}$, significant increases in modulus occurred between 0-10% ($p<0.01$) and 30-50% MHA ($p<0.01$). At 0.01 $s^{-1}$, significant increases occurred between 0-20% ($p<0.05$) and 20-50% MHA ($p<0.0001$). At the highest strain rate of 0.1 $s^{-1}$, modulus increased between 0-10% ($p<0.01$), 10-30% ($p<0.001$), and 30-40% MHA ($p<0.001$). For equivalent scaffold formulations, average modulus increased with increasing strain rate in every case, and this trend was significant at 40% MHA between 0.01 and 0.1 s−1 ($p<0.0001$) and at 50% w/w MHA between 0.001 and 0.01 s−1 ($p<0.05$).

Yield stress followed a similar trend to modulus, however the differences between scaffold formulations and between strain rates were less pronounced (FIG. 1B). Yield stresses ranged from 1.1 to 7 MPa, and the highest yield stresses at the three strain rates of 0.001, 0.01, and 0.1 $s^{-1}$ were 4.4, 5, and 7 MPa, respectively. Addition of 10% MHA to scaffolds led to a threefold increase in yield stress at a strain rate of 0.001 $s^{-1}$ (from 1.1 to 3.3 MPa) and a twofold increase in yield stress at 0.01 $s^{-1}$ (from 2 to 4.2 MPa), while 10% MHA scaffolds experienced only a 13% increase (from 4.5 to 5.1 MPa) at a strain rate of 0.1 s−1. At 0.001 $s^{-1}$, significant increases in yield stress occurred between 0-10% ($p<0.0001$) and 40-50% MHA ($p<0.01$). At 0.01 $s^{-1}$, yield stress significantly increased at 0-10% ($p<0.0001$) and 10-30% MHA ($p<0.01$). At the highest strain rate of 0.1 $s^{-1}$, yield stress increased from 0-20% ($p<0.05$) and 20-50% MHA ($p<0.05$). Similar to modulus, average yield stress for equivalent scaffold formulations increased at every strain rate. Increasing strain rate from 0.001 to 0.01 $s^{-1}$ led to an increase in yield stress for 20% ($p<0.001$), 30% ($p<0.01$), and 40% MHA scaffolds ($p<0.001$). Further increasing strain rate from 0.01 to 0.1 s resulted in significantly increased yield stress for 0% ($p<0.0001$), 30% ($p<0.01$), 40% ($p<0.01$), and 50% MHA scaffolds ($p<0.0001$).

PBAE Content

Scaffolds prepared with 30 w/w % NHA and different PBAE microparticle contents were compressed at 1 mm/min (0.0028 $s^{-1}$). PBAE microparticle content did not significantly affect 30% NHA scaffold mechanical properties for PBAE content ranging from 1 to 10 w/w %. Moduli ranging from 96-120 MPa (FIG. 14A) and yield stresses from 4.3-4.9 MPa (FIG. 14B) were recorded in these PBAE content ranges, with the highest modulus occurring at 10% PBAE and the highest yield stress occurring at 1% PBAE. Increasing PBAE content from 10 to 15% led to a significant decrease in modulus from 120 to 84 MPa ($p<0.05$). Average yield stress of 15% PBAE scaffolds was 3.6 MPa, significantly lower than 1% PBAE scaffolds ($p<0.05$), which had an average yield stress of 4.9 MPa. Samples became more viscous and difficult to inject into molds as PBAE content was increased. Beyond 15% PBAE, the mixture could still be injected, but the scaffold began precipitating before it could flow and fill the cylindrical mold, resulting in inconsistent morphology and unreliable mechanical properties.

Ratio of MHA to NHA

Scaffolds prepared with different amounts of MHA and NHA were compressed at 1 mm/min (0.0028 $s^{-1}$). All scaffolds generally increased in modulus up to 30% w/w total HA content (FIG. 15A). In scaffolds prepared with only MHA, a linear increase in modulus from 33 to 68 MPa was observed from 10% through 30% MHA, although no significant difference was observed between groups. Modulus was significantly different between 10% and 50% MHA scaffolds ($p<0.05$). Scaffolds prepared with only NHA exhibited a large and significant increase in modulus, from 53 to 141 MPa, between 20% and 30% NHA ($p<0.0001$). Scaffolds prepared with equal amounts of NHA and MHA possessed moduli similar to 30% NHA scaffolds, with 15:15, 20:20, and 25:25 NHA:MHA scaffolds all exhibiting moduli between 128 and 151 MPa. Other scaffolds with similarly high moduli included mixed NHA and MHA scaffolds with total HA concentrations of 50% (10:40, 20:30, and 30:20 NHA:MHA). Notably, 20:10 scaffolds exhibited significantly lower modulus than 15:15 and 30:0 NHA:MHA scaffolds ($p<0.0001$). Scaffolds with 40% and 50% total had the highest modulus at a 1:1 NHA:MHA ratio, which decreased when the NHA:MHA ratio was changed in either direction.

Yield stress followed trends similar to modulus, however the magnitude of these differences was lower (FIG. 3B). For example, out of all scaffolds prepared with 30% total HA, only 30:0 and 10:20 NHA:MHA samples were significantly different ($p<0.01$). Scaffolds made with 40% pure MHA or 40% pure NHA had significantly lower yield stresses than scaffolds prepared with a mixture of NHA and MHA ($p<0.01$). At 50% total HA, scaffolds with 30% or higher NHA content possessed lower yield stresses than scaffolds composed of 25:25, 20:30, or 10:40 NHA:MHA ($p<0.01$).

Injectability

Figure 16:
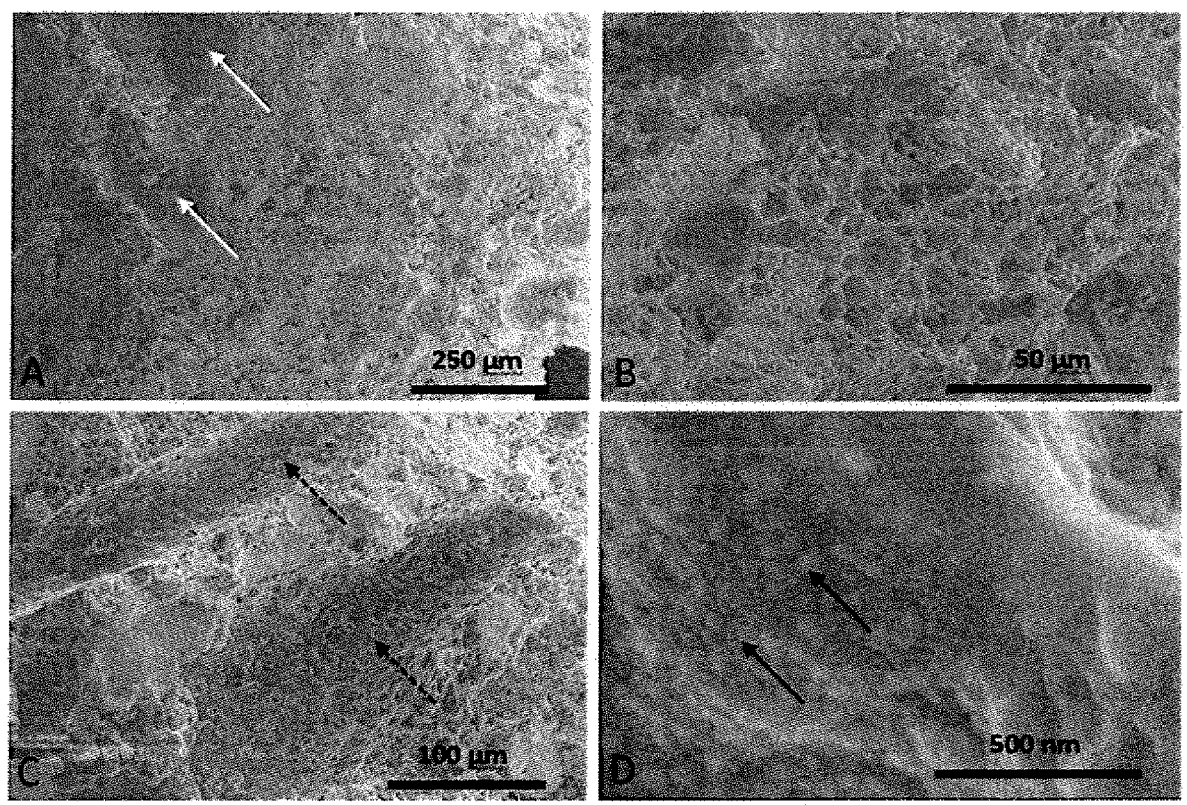
FIG. 16 shows SEM images of 30% w/w NHA scaffold microarchitecture, showing A) macropores on the order of 100 μm (white arrows), B) microporous PLGA substructure, C) elongated pores perpendicular to the surface (dotted arrows), and D) NHA nanoparticles embedded in the PLGA matrix (black arrows).

Injectable scaffold mixtures containing 5, 10, or 15 w/w % PBAE microparticle content were injected through a 16 gauge, 1.5 inch needle with a series of increasing injection forces. For each injection, the displacement of the plunger initially increased rapidly due to compression of the rubber plunger, the scaffold mixture, and any air bubbles, before reaching a period of linear displacement where flow rate was constant, followed by a relaxation period as force was removed (FIG. 16A). The linear portion of the displacement curve was used to calculate displacement rate of the syringe plunger, and the internal diameter of the syringe barrel was used to calculate volumetric flow rate. The time required to inject 0.5 mL of each mixture increased with increasing PBAE content, and it decreased with increasing injection force (FIG. 16B). Scaffolds were considered injectable if a 0.5 mL injection could be performed in 60 seconds or less, which is indicated by the horizontal dashed line in FIG. 16B. The 5% PBAE scaffolds were injectable for injection forces greater than 16 N, 10% PBAE scaffolds became injectable at 40 N, and 15% PBAE scaffolds became injectable at 75 N. The vertical dotted line at 50 N in FIG. 16B indicates the limit for a reasonable injection force, beyond which sustained forces may be uncomfortable or cause fatigue for the surgeon performing the procedure. For each scaffold composition, a logarithmic transformation of both injection force and injection time resulted in the best fit.

Microarchitecture

Figure 17:
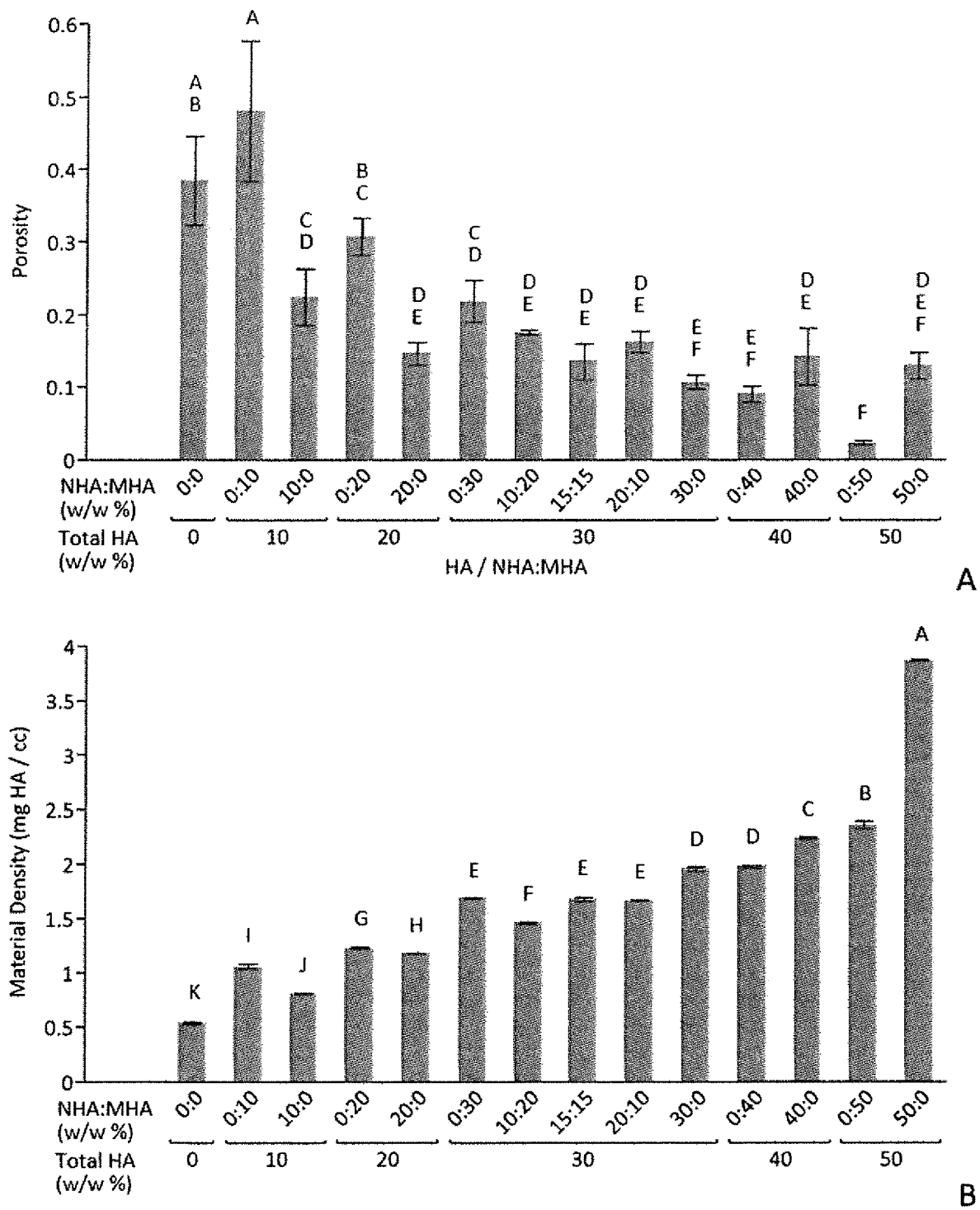
FIG. 17 shows microCT analysis of scaffolds prepared with varying NHA and MHA content, showing A) porosity and B) material density of cylindrical samples. Data are grouped by total HA content, and ordered by increasing NHA content. Shared letters denote statistical similarity, and columns without a single shared letter are significantly different. Data are mean±–standard deviation (n=3).

Visualizing the microarchitecture of scaffolds prepared with 30% w/w NHA and 5% w/w PBAE microparticles revealed two distinct levels of porosity, with NHA and PBAE particles trapped within the solid PLGA matrix. Macroscopic pores on the order of 100 μm in diameter were scattered throughout the scaffold (FIG. 17A), and the solid PLGA matrix was primarily composed of a microporous, honeycomb-like structure with pore sizes on the order of 10 μm (FIG. 17B). Elongated pores were observed at the scaffold surface (FIG. 17C). HA nanoparticles, with spherical morphology and diameters on the order of 50 nm, were present in the PLGA walls of the micropores (FIG. 17D). These particles were densely packed in 30% w/w NHA scaffolds.

Figure 18:
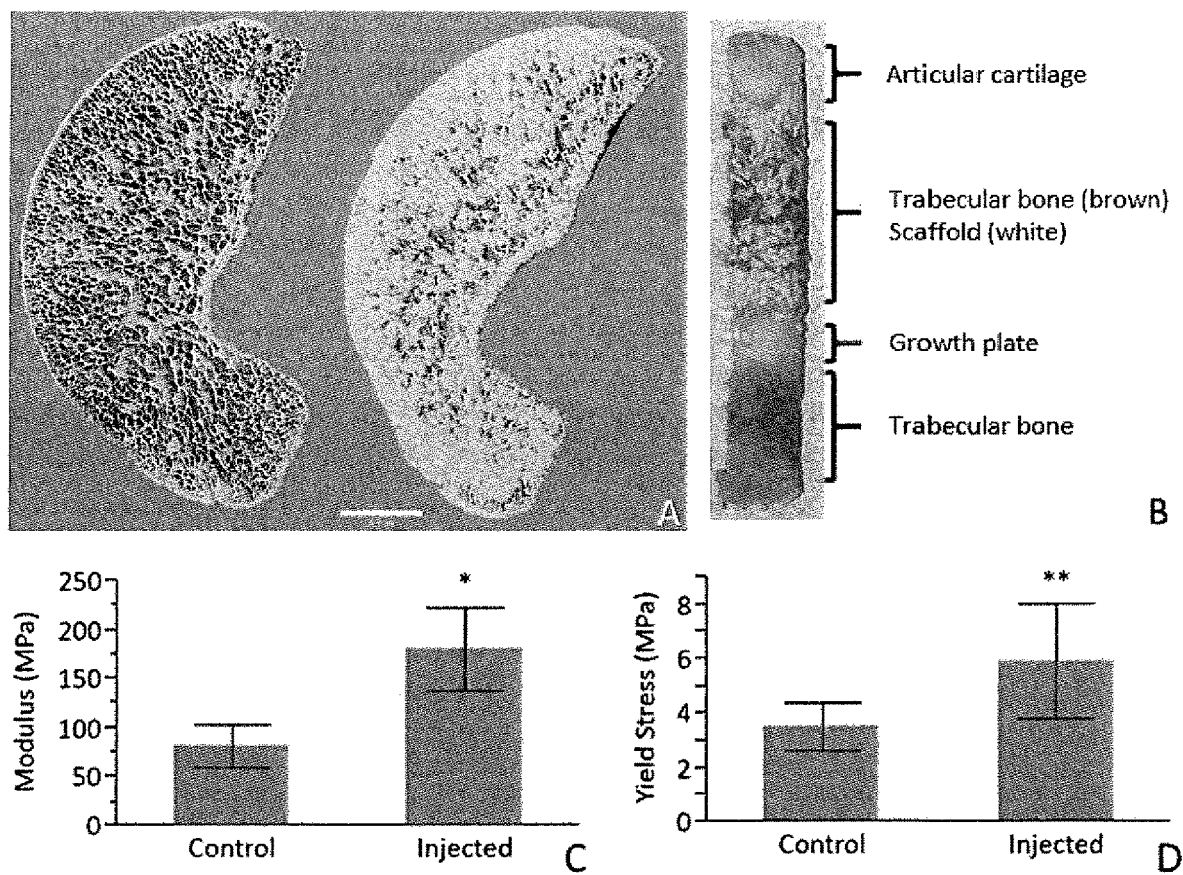
FIG. 18 shows microstructural and mechanical properties of trabecular bone samples from porcine humeral heads with or without injection of 30% NHA/5% PBAE scaffolds. A) MicroCT cutplane of humeral head prior to injection (left) and post-injection (right). B) Cylindrical bone sample containing solidified scaffold. C) Compressive modulus. D) Yield stress. Data are mean±–standard deviation (n=7). *Significantly different from Control (p<0.001). **Significantly different from Control (p<0.01). Scale bar is 5 mm.

MicroCT analysis allowed for quantification of microarchitectural parameters such as porosity and material density. Porosity generally decreased with increasing total HA content, and this trend was most pronounced in samples prepared with only MHA, which possessed porosities ranging from 2.4 to 48.1%, while samples prepared with only NHA had a porosity range of 13 to 22.5% (FIG. 18A). MHA-only samples experienced a significant decrease in porosity from 10-20% ($p<0.001$) and 30-40% ($p<0.05$), and NHA-only samples had a significant decrease in porosity from 10-30% ($p<0.05$). Samples with 30% total HA prepared with different mixtures of MHA and NHA did not exhibit significantly different porosity from each other. At equivalent weight percentages, samples prepared with pure NHA had significantly lower porosity than those prepared with MHA at 10% ($p<0.0001$), 20% ($p<0.001$), and 30% ($p<0.05$), while porosity between the two groups was not different at 40% and 50% w/w.

Material density increased with total HA content, and scaffolds prepared with NHA experienced a larger increase in density at each 10% increment of HA content (FIG. 18B). MHA scaffolds exhibited significantly higher density than NHA scaffolds at 10% ($p<0.0001$) and 20% ($p<0.01$), but due to the smaller rate of increase, they exhibited lower density than NHA scaffolds at 30%, 40%, and 50% w/w ($p<0.0001$). The 30% HA scaffolds prepared with a mixture of NHA and MHA had lower density at 10:20 NHA:MHA formulations than scaffolds prepared with 15:15 and 20:10 NHA:MHA ($p<0.0001$).

Ex Vivo Scaffold Injections

During the injection of scaffolds into the humeral heads, fluid was observed leaking out of bone near the growth plate, indicating that the scaffold was displacing marrow and filling the intertrabecular space. After the 3 mL injection into two humeral heads, there was an average reduction in free volume of 2.8 mL, corresponding to a 58% filling of the intertrabecular volume (data not shown). A comparison of cutplanes from a 3D reconstruction of the humeral heads showed scaffold material distributed throughout the bone volume, with small (sub-millimeter) regions of that were unfilled. During removal of the cylindrical cores from injected bones, it was observed that scaffold material was constrained by the articular cartilage and growth plate. Cylindrical samples of injected bone possessed a mean compressive modulus of 180 MPa, compared to 81 MPa for controls ($p<0.001$). Yield stress was also significantly higher for injected bone, with a yield stress of 5.9 MPa for injected samples compared to 3.5 MPa for controls ($p<0.01$).

Discussion

The general effects of HA additives on in situ forming PLGA scaffolds were consistent with existing research on preformed, implantable scaffolds (Huang Y X, Ren J, Chen C, Ren T B, Zhou X Y. Preparation and Properties of Poly(lactide-co-glycolide) (PLGA)/Nano-Hydroxyapatite (NHA) Scaffolds by Thermally Induced Phase Separation and Rabbit MSCs Culture on Scaffolds. Journal of Biomaterials Applications 2008; 22(5):409-432; Wei G, Ma P X. Structure and properties of nano-hydroxyapatite/polymer composite scaffolds for bone tissue engineering. Biomaterials 2004; 25(19):4749-4757; Verheyen C C P M, De Wijn J R, Van Blitterswijk C A, De Groot K. Evaluation of hydroxylapatite/poly(l-lactide) composites: Mechanical behavior. Journal of Biomedical Materials Research 1992; 26(10):1277-1296; Guan L, Davies J E. Preparation and characterization of a highly macroporous biodegradable composite tissue engineering scaffold. Journal of Biomedical Materials Research Part A 2004; 71A(3):480-487), with HA additives providing mechanical reinforcement, as evidenced by both compressive modulus and yield stress. As HA content was increased beyond a certain point (generally around 30% w/w, depending on the specific MHA and NHA content), mechanical properties either plateaued, in the case of MHA, or decreased, in the case of NHA. This effect can be attributed to the total surface area of HA relative to the volume of PLGA, which results in maximal scaffold mechanical properties when sufficient PLGA is present to bind HA together tightly without excess HA or PLGA. SEM images of the 30% NHA scaffolds showed dense packing of NHA nanoparticles embedded in the PLGA phase, which may explain why further increasing NHA content was not beneficial since particles were already in close proximity at this loading. MHA scaffolds were mechanically inferior to NHA at equivalent concentrations, likely due to the lower surface area to volume ratio of MHA, which allowed fewer PLGA:HA and HA:HA interfaces to form, and thus led to a more loosely packed HA microstructure. Additionally, there may exist a critical threshold for particle size, below which significant mechanical benefits occur in a composite (Fu S-Y, Feng X-Q, Lauke B, Mai Y-W. Effects of particle size, particle/matrix interface adhesion and particle loading on mechanical properties of particulate-polymer composites. Composites Part B: Engineering 2008; 39(6):933-961). Scaffolds with a higher NHA and MHA packing capacity could potentially be created by increasing PLGA concentration in the PLGA/NMP solution (Guan L, Davies J E. Preparation and characterization of a highly macroporous biodegradable composite tissue engineering scaffold. Journal of Biomedical Materials Research Part A 2004; 71A(3): 480-487), however, this would also increase the viscosity of the injectable mixture (Gad H, El-Nabarawi M, Abd El-Hady S. Formulation and Evaluation of PLA and PLGA in Situ Implants Containing Secnidazole and/or Doxycycline for Treatment of Periodontitis. AAPS PharmSciTech 2008; 9(3):878-884).

An in situ forming HA-PLGA-PBAE implant offers several advantages over traditional orthopedic injectables, such as poly(methyl methacrylate) (PMMA) bone cement. The heat of free radical polymerization of PMMA in situ can lead to protein denaturation and tissue necrosis (DiPisa Ja Fau-Sih G S, Sih Gs Fau-Berman A T, Berman A T. The temperature problem at the bone-acrylic cement interface of the total hip replacement. Clinical Orthopaedics and Related Research 1976; 121:95-98), whereas in situ forming PLGA scaffolds are formed via solvent exchange at ambient temperature. PMMA is not biodegradable, while PLGA degrades hydrolytically over a time period dependent on its chemical properties (Kenley R A, Lee M O, Mahoney T R, Sanders L M. Poly(lactide-co-glycolide) decomposition kinetics in vivo and in vitro. Macromolecules 1987; 20(10): 2398-2403), Biodegradation is important for a drug delivery scaffold embedded in a trabecular network, where removal surgery is impossible and a permanent implant is not ideal. Finally, the mechanical properties of PMMA are a better match for cortical bone than a trabecular bone network, while PLGA is a less stiff material that may be appropriately augmented to match trabecular bone via addition of HA filler (Saha S, Pal S. Mechanical properties of bone cement: A review. Journal of Biomedical Materials Research 1984; 18(4):435-462; Rezwan K, Chen Q Z, Blaker J J, Boccaccini A R. Biodegradable and bioactive porous polymer/inorganic composite scaffolds for bone tissue engineering. Biomaterials 2006; 27(18):3413-3431). An implant that acutely reinforces compromised bone, controls drug release, and gradually degrades to allow regeneration of native tissue can provide a comprehensive treatment in a single injection.

Interestingly, scaffolds prepared with equal amounts of NHA and MHA tended to possess comparable mechanical properties to scaffolds prepared with pure NHA or pure MHA. This similarity may be due to the tight packing of NHA in the spaces between MHA particles, resulting in scaffolds that are effectively identical to tightly packed NHA when compressed. Ultimately, the similarity between pure NHA and equally mixed NHA/MHA scaffolds is probably the result of two factors: 1) HA should be present at sufficient concentrations so that load is primarily being transmitted between tightly packed HA particles, and 2) enough PLGA should be present so that it can bind all the HA particles together. For a system intended for intraosseous injection, however, 30% NHA provides the highest mechanical properties at the lowest total HA concentration, and was therefore the most appealing formulation in terms of injectability.

Native trabecular bone in human femoral heads has a wide range of mechanical properties, with compressive moduli ranging from 100-600 MPa and yield strength ranging from 1-9 MPa (Li B, Aspden R M. Composition and mechanical properties of cancellous bone from the femoral head of patients with osteoporosis or osteoarthritis. Journal of Bone and Mineral Research 1997; 12(4):641-651; Schoenfeld C M, Lautenschlager E P, Meyer P R, Jr. Mechanical properties of human cancellous bone in the femoral head. Med & biol Engng 1974; 12(3):313-317). For conditions that may be candidates for an injectable, intraosseous treatment, these values may be reduced by 24% (yield stress) and 20% (modulus) in osteoporotic patients (Li B, Aspden R M. Composition and mechanical properties of cancellous bone from the femoral head of patients with osteoporosis or osteoarthritis. Journal of Bone and Mineral Research 1997; 12(4):641-651), or 50% (yield stress) and 72% (modulus) in osteonecrosis patients (Schoenfeld C M, Lautenschlager E P, Meyer P R, Jr. Mechanical properties of human cancellous bone in the femoral head. Med & biol Engng 1974; 12(3): 313-317). Scaffolds with material properties similar to trabecular bone can aid load-bearing while the drug delivery component of the scaffold exerts its effect (Rezwan K, Chen Q Z, Blaker J J, Boccaccini A R. Biodegradable and bioactive porous polymer/inorganic composite scaffolds for bone tissue engineering. Biomaterials 2006; 27(18):3413-3431). The average modulus of scaffolds prepared with 30% NHA was 141 MPa, and the average yield stress was 6.2 MPa, which are both within the range of trabecular bone. Although in situ forming PLGA systems have not been extensively investigated for their mechanical properties, the strength of these scaffolds is 10-fold higher than a similar system containing 33% α-tricalcium phosphate and PLGA of a lower molecular weight (Schloegl W, Marschall V, Witting M Y, Volkmer E, Drosse I, Leicht U, Schieker M, Wiggenhorn M, Schaubhut F, Zahier S and others. Porosity and mechanically optimized PLGA based in situ hardening systems. European Journal of Pharmaceutics and Biopharmaceutics 2012; 82(3):554-562). Furthermore, the yield stress was on the higher end of healthy trabecular bone, so even if scaffolds are slightly less stiff than the native bone tissue, they can withstand similar stresses to healthy bone before beginning to collapse. It is important to consider these scaffolds as a means for temporary augmentation that can acutely preserve bone while treatment occurs, not as a replacement for healthy bone tissue. For this purpose, the material properties of the 30% NHA system are sufficient.

Injectability is a unique concern for in situ forming scaffolds, because both HA and PBAE particle additives increase viscosity. Because prior injectable PLGA systems were not intended for mechanical support, and drug is usually mixed freely into the polymer solution, viscosity has not been a limiting factor when designing these systems. However, injectable bone cements and fillers have encountered issues with injectability because they are composed of a liquid phase containing high concentrations of suspended particles (Bohner M, Baroud G. Injectability of calcium phosphate pastes. Biomaterials 2005; 26(13):1553-1563; Alves H L, Santos L A, Bergmann C P. Injectability evaluation of tricalcium phosphate bone cement. J Mater Sci: Mater Med 2008; 19(5):2241-2246). For example, decreasing the liquid to powder ratio increases the required injection force and decreases the extruded fraction (Khairoun I, Boltong M G, Driessens F C M, Planell J A. Some factors controlling the injectability of calcium phosphate bone cements. J Mater Sci: Mater Med 1998; 9(8):425-428; Bohner M, Baroud G. Injectability of calcium phosphate pastes. Biomaterials 2005; 26(13):1553-1563), which is roughly analogous to increasing HA content in an injectable PLGA system. Various additives have been investigated to decrease the required injection force (Leroux L, Hatim Z, Frèche M, Lacout J L. Effects of various adjuvants (lactic acid, glycerol, and chitosan) on the injectability of a calcium phosphate cement. Bone 1999; 25(2, Supplement 1):31S-34S). Injectability will likely be a persistent, nontrivial issue for in situ forming PLGA systems containing mechanical filler. Setting NHA content to a constant 30% and varying PBAE microparticle content revealed that there is a clear limit on PBAE microparticle content (and, therefore, drug loading) beyond which the system cannot be injected without exceeding limits of injection force or injection time. Longer-duration injections may be complicated by the precipitation of PLGA into a solid (Kempe S, Metz H, Mader K. Do in situ forming PLG/NMP implants behave similar in vitro and in vivo? A non-invasive and quantitative EPR investigation on the mechanisms of the implant formation process. Journal of Controlled Release 2008; 130(3):220-225), leading to increased backpressure and a loss of injectability, while injections requiring large sustained force may be uncomfortable for the surgeon performing the procedure. The injection force limit may be circumvented by the use of an injection gun, which would improve injection time and greatly increase the injection force limit.

The space-filling and mechanical reinforcement potential of an injectable system is likely to differ in situ from simulated tests, due to the presence of a constrained geometry filled with marrow and bordered by anatomical features such as articular cartilage, cortical bone, and the growth plate. The incomplete filling of free volume by the scaffold suggests that the material establishes flow channels of low resistance, resulting in small pockets of unfilled bone. MicroCT images and cylindrical tissue samples, however, show that these unfilled regions are distributed throughout the bony network, and the scaffold was capable of filling the bone tissue in all directions. Furthermore, injected bone tissue was significantly stronger and stiffer than native tissue, suggesting that the 58% filling that was achieved is sufficient to greatly improve mechanical properties of trabecular bone.

Conclusions

The present study demonstrated the feasibility of an injectable PLGA scaffold containing PBAE and HA particles as a mechanically supportive, in situ forming scaffold. Injectable scaffold mixtures are capable of being injected through a standard bone biopsy needle, infiltrating trabecular bone, then solidifying to produce scaffolds with mechanical properties comparable to those of trabecular bone. This injectable scaffold offers a promising treatment platform for ailments requiring both drug delivery and mechanical reinforcement of trabecular bone, and it has the advantage of being easily injectable and fully resorbable. This particular system was optimized to accommodate NHA mechanical filler and PBAE microparticles for drug delivery, with the goal of an intraosseous injection into the femoral head. In situ forming PLGA systems have traditionally been viewed purely as drug delivery devices, but this study clearly demonstrates the potential for a mechanical component to these systems as well.

Example 3

Poly(β-amino ester) (PBAE) hydrogel microparticles were incorporated into a PLGA matrix to provide several new functions: mechanical support, porosity, space-filling, and controlled co-delivery of antibiotics and osteogenic drugs. PBAE-containing PLGA ISIs are more effective space-filling scaffolds and offer improved release kinetics compared to existing ISIs used to treat periodontitis.

Materials

Diethylene glycol diacrylate and poly(ethylene glycol) 400 diacrylate (PEG400DA) were bought from Polysciences, Inc. (Warrington, Pa.). High molecular weight PLGA (HMW PLGA; 50:50 lactide:glycolide, 0.55-0.75 dL/g in hexafluoroisopropanol, carboxylate-terminated) and low molecular weight PLGA (LMW PLGA; 50:50 lactide: glycolide, 0.15-0.25 dL/g in hexafluoroisopropanol, carboxylate-terminated) were purchased from DURECT (Birmingham, Ala.). 2,2-Dimethoxy-2-phenylacetophenone (DMPA), N-methyl-2-pyrrolidone (NMP), gelatin (from porcine skin, type A), glutaraldehyde (25%, grade I), agarose, trifluoroacetic acid (TFA), doxycycline hyclate, and glycine were obtained from Sigma Aldrich (St. Louis, Mo.). Simvastatin was from Haorui Pharma-Chem (Edison, N.J.).

PBAE Hydrogel Preparation

PBAE macromer was synthesized by reacting diacrylate with isobutylamine at 85° C. for 48 hours. Macromers were named according to the classification system from Anderson et al., in which the letter corresponds to a specific diacrylate and the number corresponds to a specific amine (Anderson D G, Tweedie C A, Hossain N, Navarro S M, Brey D M, Van Vliet K J, et al. A combinatorial library of photocrosslinkable and degradable materials. Adv Mater 2006; 18:2614-8).

Thus, macromer made by reacting PEG400DA with isobutylamine for 48 hours was termed H6. A macromer containing a 2:1 molar ratio of diethylene glycol diacrylate: PEG400DA was also created and will subsequently be referred to as AH6. The ratio of total acrylate to amine reactive groups was 1.2:1 for both macromers.

PBAE hydrogels were formed by adding 0.1% w/w DMPA, dissolved in ethanol, to the macromer, pipetting this mixture between two parallel glass plates, and exposing the mixture to a 365 nm UV flood source for 5 minutes to crosslink the macromer. The resulting hydrogels were washed overnight in ethanol to remove residual DMPA and unreacted monomers and then stored in a desiccator until use.

PBAE microparticles were made by swelling PBAE hydrogels in ethanol for 1 hour and then grinding them with a mortar and pestle. The slurry was passed through a 250 μm sieve using an ethanol wash, and any larger particles were re-ground until 100% of the hydrogel was sieved. The microparticle slurry was lyophilized, and the resulting microparticles were stored in a desiccator.

Injectable Mixture Formulations

A PLGA solution was formed by dissolving 30% or 40% w/w of either HMW or LMW PLGA in NMP overnight. PBAE microparticles (H6, AH6, or a mixture of the two) were added to the PLGA solution at 10% w/w and stirred until the mixture was homogeneous. Simvastatin or doxycycline (2% w/w individually or 2% w/w each for co-delivery) were added to the PLGA-PBAE-NMP suspension and mixed thoroughly. Alternatively, doxycycline was pre-loaded into AH6 microparticles by swelling the microparticles with a 3 mg/mL doxycycline solution in acetone at a ratio of 100 mg AH6 to 500 μL of solution. These swollen particles were lyophilized for 24 hours, resulting in doxycycline pre-loaded into AH6 microparticles. Pre-loaded AH6 microparticles at 10% w/w in PLGA solutions were then used in drug release studies. HMW formulations containing simvastatin were tested first, and the most promising mixtures were used in subsequent tests with doxycycline and/or LMW PLGA. Table 1 contains a list of all scaffold formulations that were examined for the drug release studies.

TABLE 1

Scaffold formulations investigated for drug release.

| Scaffold Name | PLGA | PLGA % | PBAE | Drugs |
|---|---|---|---|---|
| HMW-AH | HMW | 30 | AH6 | S/D/S + D/D(Pre) |
| HMW-H | HMW | 30 | H6 | S |
| HMW-H/AH | HMW | 30 | AH6 + H6 | S |
| HMW-Control | HMW | 30 | None | S/D |
| LMW-AH | LMW | 30 | AH6 | S/D/S + D |
| LMW-Control | LMW | 30 | None | S/D/S + D |
| 40LMW-AH | LMW | 40 | AH6 | S/D/S + D/D(Pre) |
| 40LMW-Control | LMW | 40 | None | S/D/S + D/D(Pre) |

Abbreviations:
S = simvastatin;
D = doxycycline.
(Pre) indicates drug was pre-loaded into PBAE microparticles, and
"+" indicates co-delivery of drugs from the same scaffold.

Microarchitecture and Mass Change

To observe changes in ISI mass and microarchitecture, the following drug-free formulations were prepared: HMW-AH, HMW-H, HMW-H/AH, HMW-Control, LMW-AH, and LMW-Control (Table 1). In a 96-well plate, approximately 10 mg of injectable scaffold mixture were injected dropwise from an 18-gauge needle into 300 μL of phosphate-buffered saline (PBS), pH 7.4. The syringe was weighed after each injection to calculate the mass of each scaffold. PBS was replaced daily to prevent buildup of degradation byproducts. At each time point, 3 scaffolds from each group were removed, dabbed dry, and weighed to measure the wet mass. For HMW scaffolds, samples were collected at 1 and 5 days following the injection and then every 5 days thereafter. For LMW scaffolds, samples were collected at 1 and 2 days and then every other day afterward. All collected ISIs were lyophilized for 24 hours and weighed again to determine dry mass. HMW scaffolds were then scanned using a SCANCO MicroCT 40 (SCANCO Medical AG, Switzerland) with X-ray parameters of 55 kV and 145 mA, and a 6 μm voxel size. A built-in bone trabecular morphometry analysis tool was used to create 3-D reconstructions, and measurements of porosity, mean pore size, and material density were conducted. To quantify accessible volume and surface area, simulated mercury intrusion porosimetry was run on the 3-D reconstructions using an included script. At select time points, samples were freeze-fractured, and a Hitachi S-4300 scanning electron microscope (SEM) at 4 kV accelerating voltage was used to visualize the microarchitecture of scaffolds.

Mechanical Tests

All mechanical tests were performed with a Bose ELF 3300 system. Gelatin slabs (20%) measuring 8 mm thick were crosslinked by overnight immersion in 5 mM glutaraldehyde. Unreacted aldehyde groups were quenched by placing the crosslinked gelatin slabs in a 50 mM glycine solution for 2 hours followed by serial washing with deionized water. Cylindrical samples (4 mm in diameter) were punched out of the slabs, and their mechanical properties were characterized by compressing these cylindrical samples to 10% strain at a frequency of 1 Hz for 30 seconds to mimic chewing conditions (Goktas S, Dmytryk J J, McFetridge P S. Biomechanical behavior of oral soft tissues. J Periodontol 2011; 82:1178-86). The slabs containing cylindrical holes were used as molds to inject both HMW and LMW Control and AH-containing scaffolds. After injection, the molds were capped with 2% agarose slabs, lightly clamped shut to prevent extrusion of material due to swelling, and immersed in PBS. After 3, 6, 9, 12, or 15 days, the solidified samples within the molds were subjected to compression at a displacement rate of 0.5 mm/sec. The interfacial shear strength required for push-out was calculated by dividing the maximum push-out force by the scaffold surface area in contact with the mold. Cylindrical scaffolds that had been pushed out of their molds were tested for their compressive properties under 1% strain triangular waves applied at a frequency of 1 Hz for 60 seconds. The initial modulus was determined from the first compression cycle, and the equilibrium modulus was measured during the final cycle. Resilience was calculated by integrating the linear region of the stress-strain curve. These methods followed protocols established to measure the mechanical properties of gingival tissue (Goktas S, Dmytryk J J, McFetridge P S. Biomechanical behavior of oral soft tissues. J Periodontol 2011; 82:1178-86).

Drug Release

Approximately 100 mg of each mixture (Table 1) were injected dropwise into 1 mL PBS, where the PLGA rapidly solidified into droplet-shaped scaffolds. At each time point, supernatant was entirely removed, stored in a refrigerator, and replaced with fresh PBS. A Hitachi Primaide HPLC system with a Kinetex C18 column was run isocratically at 1 mL/min with a mobile phase composed of 70% acetonitrile/30% water+0.1% TFA to detect simvastatin at 240 nm. Collected supernatant was mixed with ethanol at a 2:1 supernatant:ethanol ratio to dissolve any precipitated simvastatin prior to HPLC analysis. Doxycycline was assayed using a mobile phase composed of 30% acetonitrile/70% water+0.1% TFA running at 1 mL/min and with detection at 350 nm.

Results

Mass Change

HMW-Controls exhibited little dry mass change through the first 15 days of degradation, after which a linear decrease in mass of 4.8%/day occurred through day 30 (FIG. 19A). A significant (p<0.05) decrease in mass was observed at each time point from day 20 and onward. Over the first 5 days, the wet mass of these scaffolds decreased significantly (p<0.05) at a rate of 9.4%/day and then increased slightly between days 10 and 20, before gradually declining through day 35, although none of these later changes was significant (FIG. 19B). Both HMW-AH and HMW-H/AH scaffolds exhibited a small wet mass loss in the first day, followed by a relatively linear 6.5%/day wet mass increase through day 30 to a maximum of 273% of original mass. At day 35, scaffolds fell apart upon handling, and measurable mass decreased to 93% of the initial value. HMW-H scaffolds had a larger wet mass loss of 37% (p<0.05) after 1 day, and between days 5 and 25, an 8.6%/day mass increase occurred. A plateau was reached between days 25 and 30 prior to a large decrease in mass at day 35. After a 1-day dry mass loss of 12%, HMW-AH scaffolds lost mass at a rate of 1.7%/day until day 10. Mass loss resumed at day 15 and continued at a rate of 0.87%/day until day 30. HMW-H/AH scaffolds had a dry mass loss of 26% after day 1, and no significant mass change followed through day 30. Similarly, HMW-H scaffolds exhibited a large initial dry mass loss of 38% after 1 day, and no significant subsequent mass loss occurred until day 30 (p<0.05).

LMW-Controls exhibited a gradual dry mass decrease to 89% after 8 days, after which the mass decreased linearly at a rate of 3%/day through day 30 (FIG. 19C). LMW-Control wet mass rapidly increased to 193% through the first 5 days, then sharply declined and fluctuated around 150% through day 16 (FIG. 19D). Beyond day 16, a linear mass loss of 7%/day occurred through day 30. LMW-AH scaffolds decreased steadily in dry mass at a rate of 5%/day for the first 8 days, followed by a brief plateau through 12 days, and terminating with a linear mass loss of 2%/day through day 30. LMW-AH wet mass increased for the first 5 days and plateaued, fluctuating around 150% through day 16. After day 16, a mass loss of 7%/day occurred through day 30.

Microarchitecture

Figure 20:
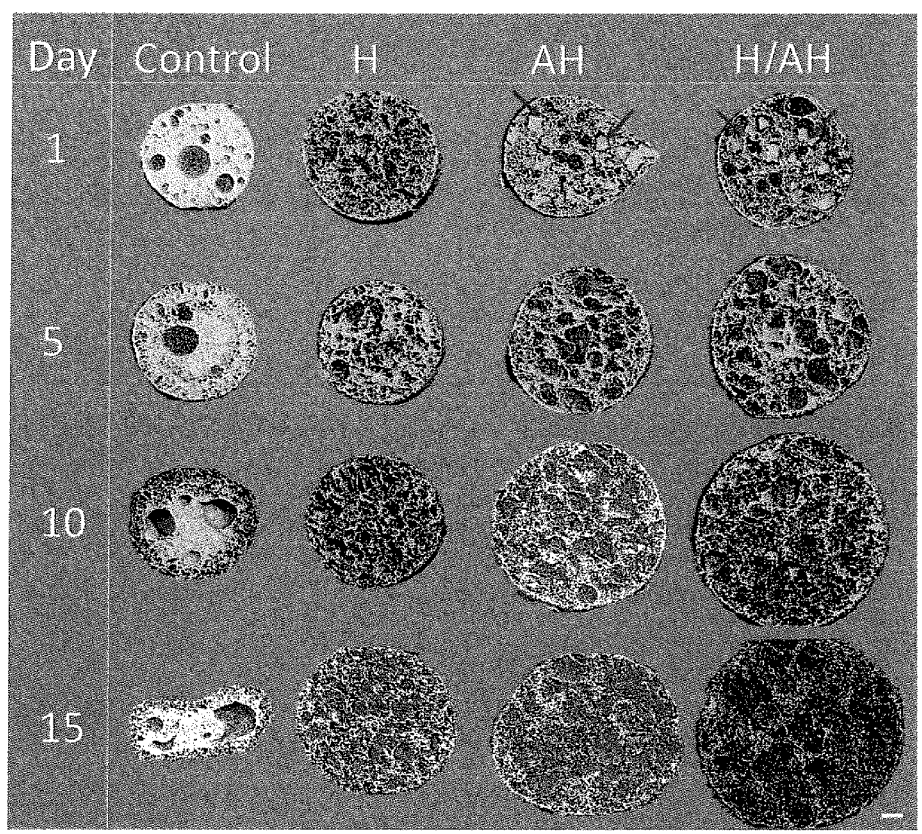
FIG. 20 shows bisected microCT reconstructions of HMW ISIs containing no additives (Control) or 10% PBAE particles (H, AH, or H/AH). White indicates material present in the cut plane. Arrows indicate solid material within pores.

LMW samples were unable to be analyzed using microCT due to their fragility following lyophilization, resulting in structural collapse and unreliable scan data. The microarchitecture of HMW-Controls changed dramatically throughout the first 15 days of degradation, leading to collapse, while HMW ISIs containing PBAE additives possessed a more uniform pore structure and swelled visibly throughout the 15 day period (FIG. 20). After 1 day, HMW-Controls were composed of a dense solid phase with large, homogeneously distributed spherical pores with diameters on the order of 0.5 mm to 2 mm. By day 5, some large pores remained in the core of the scaffold, while most were present near the edges and were oriented radially. By day 10, the radial pores were more numerous, surrounding the dense core, and by day 15, the scaffolds had collapsed. HMW-H scaffolds possessed a uniformly porous microarchitecture by day 1, and there were little microstructural changes until day 15, when noticeable swelling had occurred. At day 15, HMW-Controls had a 17% increase over initial volume, while HMW-H, HMW- H/AH, and HMW-AH had increases of 33%, 84%, and 95%, respectively. HMW-AH and HMW-H/AH scaffolds both initially possessed porous networks with radiopaque regions inside these pores, which is indicative of non-degraded PBAE material (FIG. 2, arrows). By day 5, scaffolds were noticeably swollen, and there was little evidence of non-degraded PBAE material, resulting in a uniformly porous microarchitecture; swelling increased progressively through day 15. None of the scaffolds containing PBAE additives collapsed within the 15-day period.

HMW ISIs generally increased in both porosity (FIG. 21A) and volume (FIG. 21B) as they degraded. Specifically, HMW-Controls initially possessed 24% porosity, which increased to a maximum of 54% at day 10, and then declined slightly to 46% by day 15. All PBAE-containing scaffolds steadily increased throughout the 15-day period, with initial porosities ranging from 42% (HMW-AH) to 55% (HMW-H). All PBAE-containing ISIs possessed significantly higher porosities than HMW-Controls at all time points ($p<0.001$). Among PBAE-containing ISIs, only HMW-AH at day 1 differed significantly in porosity from others. Scaffold volume, normalized to initial mass, showed that HMW-Controls increased slightly in volume by day 5 before gradually declining (FIG. 21B), and had significantly lower volume than all PBAE groups throughout degradation ($p<0.01$). HMW-H exhibited an initial decrease in scaffold volume between days 1 and 5, followed by a linear increase beyond the initial volume by day 15. Both HMW-AH and HMW-H/AH generally increased in volume throughout the 15 day period.

Figure 21:
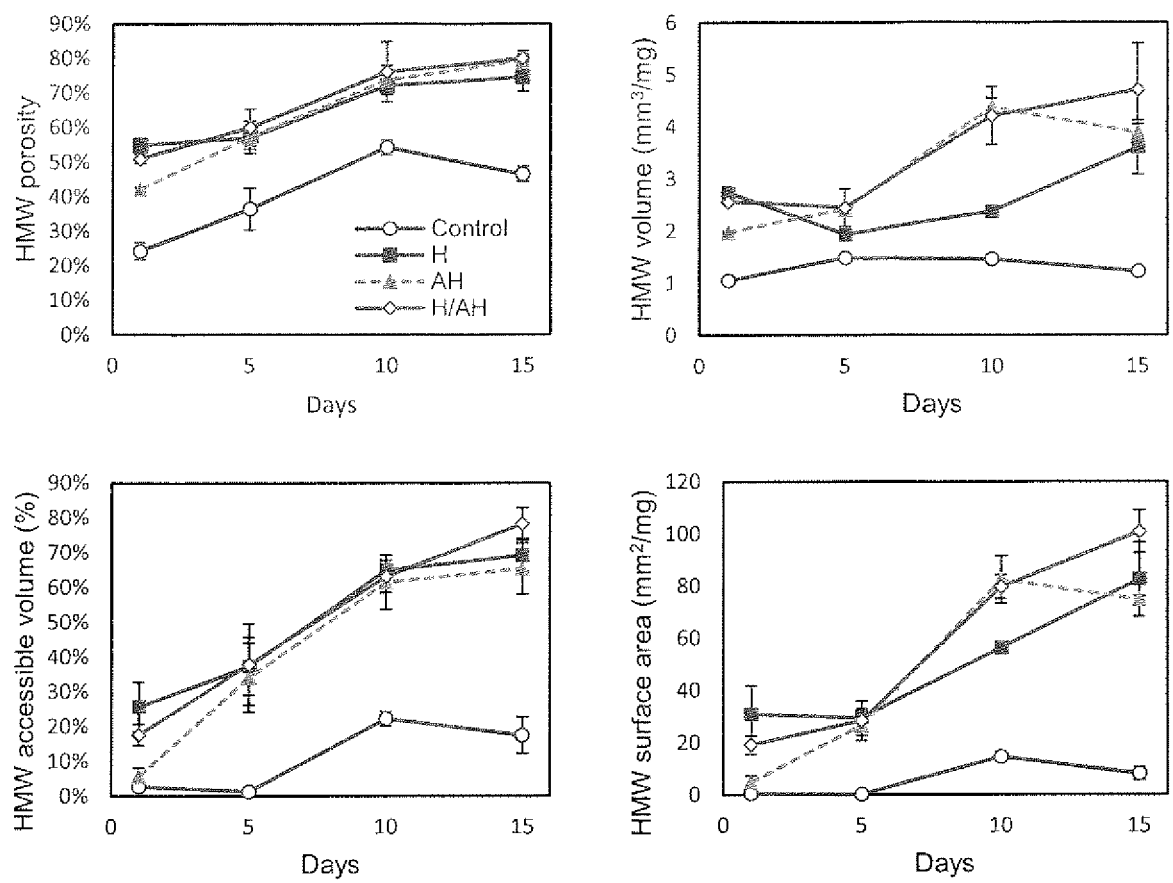
FIG. 21 shows microarchitecture of HMW scaffolds throughout degradation. A) Porosity and B) mass-normalized volume of scaffolds, evaluated using microCT. Accessibility of C) scaffold volume and D) mass-normalized surface area to a simulated 24 μm sphere. Data are mean±standard deviation (n=3).

Accessible volume was measured for various simulated penetrating sphere diameters ranging from 12 μm to 120 μm, and the volume accessible by a 24 μm sphere was compared between groups over 15 days (FIG. 21C). This diameter approximates the size of the progenitor cells that may migrate into these pores (Izumi K, Tobita T, Feinberg S E. Isolation of human oral keratinocyte progenitor/stem cells. J Dent Res 2007; 86:341-6; Lavenus S, Pilet P, Guicheux J, Weiss P, Louarn G, Layrolle P. Behaviour of mesenchymal stem cells, fibroblasts and osteoblasts on smooth surfaces. Acta Biomater 2011; 7:1525-34). At day 1, HMW-Control and HMW-AH possessed significantly lower accessible volume than did HMW-H and HMW-AH samples ($p<0.01$). At day 5 and beyond, all PBAE-containing ISIs possessed similar accessible volumes, which increased from 34-38% at day 5 to 65-78% by day 15. From days 5 through 15, controls had significantly lower accessible volume ($p<0.001$). Accessible surface area was normalized to initial scaffold mass, and measured using the same 24 μm penetrating sphere size (FIG. 21D). The trends for accessible surface area were similar to accessible volume, with HMW-Control and HMW-AH initially possessing significantly lower values than HMW-H and HMW-AH ($p<0.01$). Controls remained significantly lower than all other groups for each subsequent time point ($p<0.001$). HMW-AH increased linearly in accessible surface area through day 15 before plateauing, while both HMW-H/AH steadily increased in accessible surface area throughout degradation. HMW-H remained relatively unchanged between days 1-5 before increasing linearly through day 15.

Mechanical Properties

Figure 22:
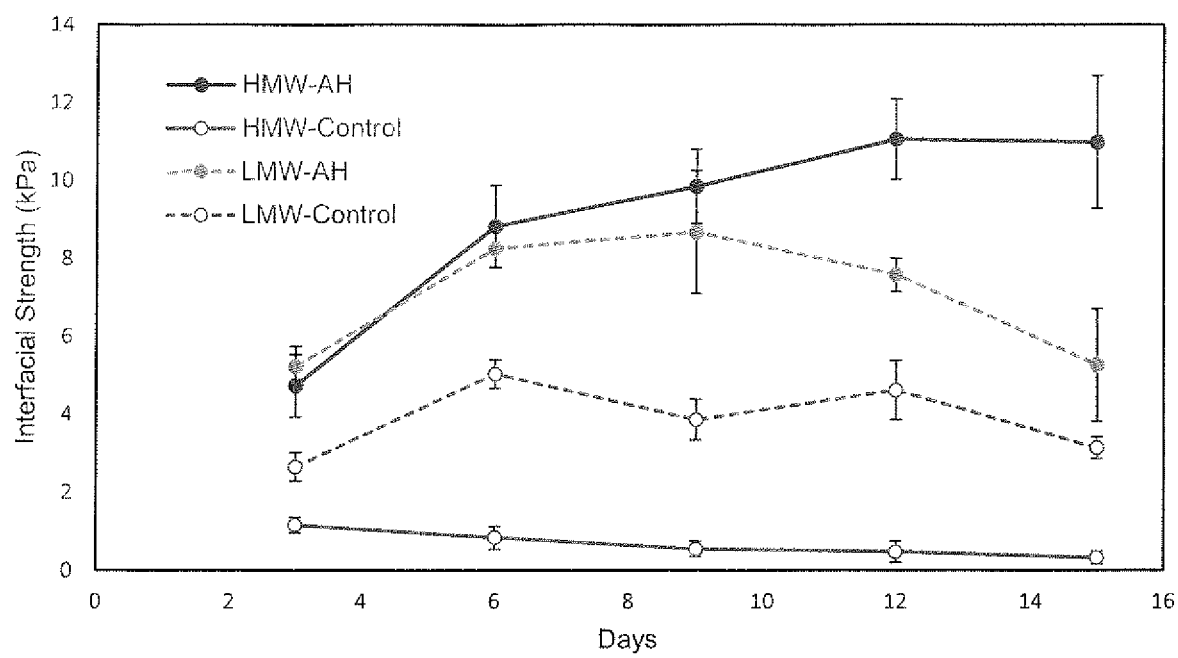
FIG. 22 shows interfacial strength measured from push-out tests on cylindrical samples within gelatin molds. Data are mean±standard deviation (n=3).

The interfacial strength between ISI and cylindrical gelatin mold, as measured by maximum push-out force, decreased over 15 days for HMW-Controls but increased over the same period for HMW-AH (FIG. 22). For HMW-Controls, the interfacial strength was 1.2 kPa at 3 days, and then decreased relatively linearly until it was significantly reduced to 0.5 kPa by day 12 ($p<0.05$). The interfacial strength of HMW-AH samples increased significantly from 4.7 kPa at day 3 to 8.8 kPa at day 6 ($p<0.01$), and the interfacial strength continued to increase, although not significantly, to 11 kPa by day 15. At every time point, the interfacial strength of HMW-AH significantly exceeded that of HMW-Controls ($p<0.001$).

Figure 23:
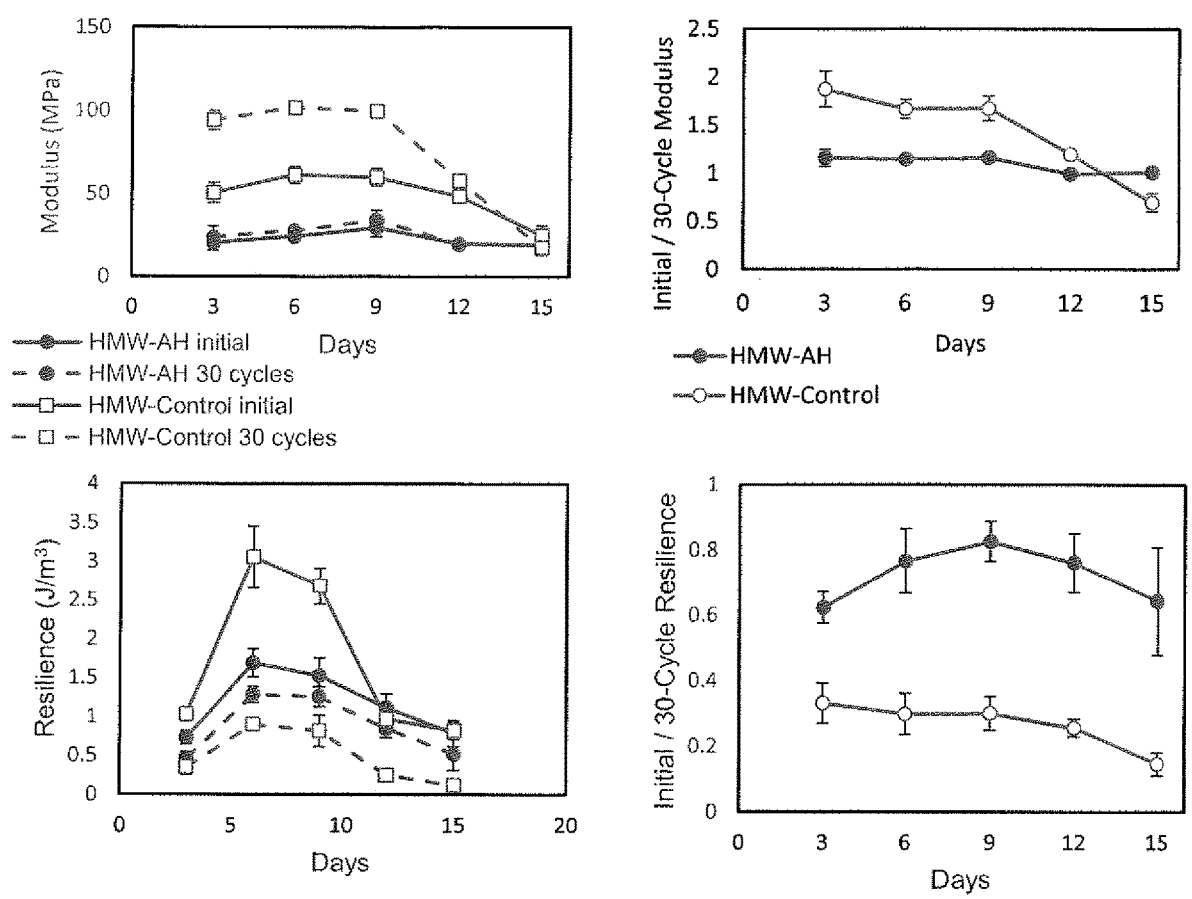
FIG. 23 shows mechanical properties of cylindrical implants subjected to 30 cycles of 1% compressive strain at 1 Hz. A) Initial and 30-cycle modulus. B) Ratio of initial to 30-cycle modulus. C) Initial and 30-cycle resilience. D) Ratio of initial to 30-cycle resilience. Data are mean±standard deviation (n=3).
Figure 23:
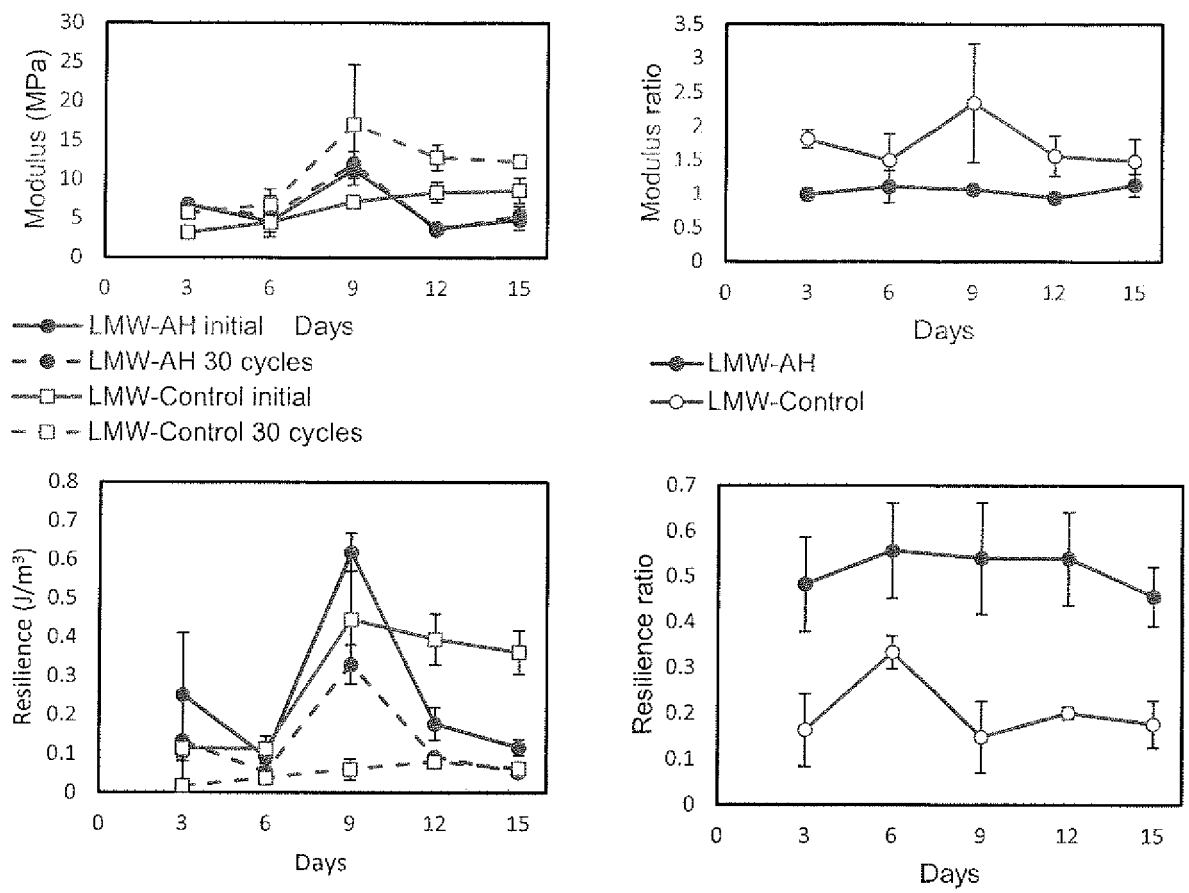

LMW samples exhibited a less dramatic difference between AH and Control groups (FIG. 22). The interfacial strength for LMW-Controls remained significantly higher than HMW-Controls and lower than HMW-AH at all time points ($p<0.01$), with interfacial strengths ranging from 2.7 to 5 kPa. LMW-AH interfacial strength increased from 5.2 kPa at day 3 to 8.7 kPa by day 9, and then decreased down to 5.3 kPa by day 15. LMW-AH samples possessed significantly higher interfacial strength than did LMW-Controls for the first 12 days tested ($p<0.005$), and the interface remained similar to that for HMW-AH samples until days 12 and 14, which were both significantly lower than corresponding HMW-AH interfacial strengths ($p<0.01$). Both HMW-Control and HMW-AH cylindrical samples exhibited initial and 30-cycle compressive moduli that remained unchanged through the first 9 days, followed by a decrease through day 15 (FIG. 23A). For HMW-Controls, initial modulus ranged between 48 and 61 MPa through the first 12 days, and then a significant decrease to 25 MPa occurred ($p<0.01$). Significant changes in HMW-AH samples were detected only between day 15 and days 6 or 9 ($p<0.05$), and over the 15-day period, these moduli ranged from a minimum of 14 MPa at day 15 to 29 MPa at day 9. The 30-cycle modulus of HMW-Controls did not change for the first 9 days, with moduli ranging from 94 to 102 MPa. Significant decreases occurred at day 12, to 58 MPa, and at day 15, to 17 MPa ($p<0.0001$). Modulus ranged from 24 MPa at day 3 to 34 MPa by day 9, and then decreased significantly to 14 MPa by day 15 ($p<0.001$). The ratio of the initial to the 30-cycle modulus did not change significantly throughout the 15 day period for HMW-AH samples, and it ranged from 0.95 at day 15 to 1.16 at day 9 (FIG. 23B). For HMW-Controls, the modulus ratio ranged from 1.67 to 1.88 over the first 9 days, and then decreased significantly to 1.2 by day 12 and 0.7 by day 15 ($p<0.01$).

Resilience of HMW-Controls and HMW-AH samples increased between days 3 and 6 before declining through day 15, and HMW-Controls exhibited the highest initial resilience and the lowest 30-cycle resilience (FIG. 23C). Resilience from the initial compression cycle of HMW-Controls increased significantly from 1 $J/m^3$ at day 3 to 3.1 $J/m^3$ at day 6 ($p<0.0001$), and then decreased significantly at day 12 to 0.97 $J/m^3$ ($p<0.0001$). The 30-cycle resilience followed the same trend, with 0.35 $J/m^3$ at day 3, which increased significantly to 0.9 $J/m^3$ by day 6, and then dropped significantly to 0.25 $J/m^3$ by day 12 ($p<0.001$). Through the first 12 days, the ratio of the initial to the 30-cycle resilience ranged from 0.26 to 0.33, and a significant decrease occurred between days 9 and 15, down to 0.15 ($p<0.05$) (FIG. 23D). HMW-AH initial resilience increased significantly between days 3 and 6, from 0.73 to 1.7 $J/m^3$ ($p<0.001$). The resilience did not change until day 15, when a significant decrease occurred from 1.53 $J/m^3$ at day 9 to 0.79 $J/m^3$ at day 15 ($p<0.01$). The 30-cycle modulus of HMW-AH samples increased significantly from 0.46 $J/m^3$ at day 3 to 1.28 $J/m^3$ at day 6 ($p<0.0001$), with subsequent significant decreases at day 12, to 0.83 $J/m^3$ ($p<0.01$), and at day 15, to 0.52 $J/m^3$3 ($p<0.05$). The ratio of these two resilience values for HMW-AH samples did not change significantly throughout the 15 day period.

LMW-Controls possessed uniformly higher ratios of initial to 30-cycle modulus at each time point compared to LMW-AH, although this difference was significant at only days 3 and 12 (p<0.05) (FIG. 23F). Similar to HMW samples, LMW-AH samples exhibited an initial to 30-cycle modulus ratio ranging from 0.94 to 1.13. While LMW-Control initial modulus increased steadily from 3.2 to 8.6 MPa between days 3 and 12, LMW-AH initial modulus fluctuated from 3.7 to 12 MPa, with a maximum at 9 days and a minimum at 12 days, resulting in no clear trend (FIG. 23E). The initial resilience of both LMW-AH and LMW-Control was highest at day 12, and in all cases, the 30-cycle resilience was lower than the initial value for both LMW-AH and LMW-Control (FIG. 23G). However, the ratio of initial to 30-cycle resilience of LMW-AH, ranging from 0.46 to 0.56, was significantly higher at every time point than the same ratio for LMW-Control (p<0.05), which ranged from 0.15 to 0.33 (FIG. 5H).

Drug Release

HMW scaffolds loaded with simvastatin released the drug over 90 days, and scaffolds containing PBAE microparticles produced release profiles with distinct regions of different release rates (FIG. 24A). HMW-Controls exhibited a significantly higher 1-day burst of 36% (p<0.001) compared to all PBAE-containing groups, which had a burst of 6% or less. HMW-Controls exhibited a declining daily release rate over the course of 40 days, with residual simvastatin released over the last 40 days as scaffolds completely degraded. HMW-H exhibited a relatively linear release rate of 1%/day through day 30, followed by a period of minimal release through day 60. HMW-AH had a release rate of 2.8%/day for the first 13 days, followed by a period of 1%/day through day 30 and then 0.25%/day through day 50. HMW-H/AH had release rates of 2.1%/day through day 13, 1%/day through day 30, and then 0.2%/day through day 50. Beyond day 60, the remaining drug was released through day 90 as scaffolds completely degraded.

LMW scaffolds released simvastatin through 30 days, and AH6 microparticle additives reduced the burst for each formulation (FIG. 24B). LMW-Controls had 47% burst followed by a roughly linear release rate of 2.1%/day through day 30. The burst was reduced to 21% for 40LMW-Controls, after which the release rate steadily declined through day 30. There was no difference in simvastatin release kinetics between LMW-AH scaffolds containing simvastatin alone or doxycycline and simvastatin together. Both LMW-AH and 40LMW-AH scaffolds had no appreciable burst, and linear release rates ranged from 2.3 to 2.5%/day through days 24 and 26, respectively. After day 24 or 26, the release rate increased to 10%/day until all drug was released.

Doxycycline exhibited similar release patterns from both HMW (FIG. 25A) and LMW ISIs (FIG. 25B), with no difference observed between PBAE-containing scaffolds and controls. Pre-loading doxycycline into PBAE microparticles resulted in a 1-day burst similar to controls, but with significantly more drug released over the remainder of the week. In all cases where the antibiotic was not pre-loaded into AH6 microparticles, release plateaued within one or two days, and drug was released incrementally for the remainder of the monitored period. In all HMW ISIs tested, release plateaued at approximately 70% of total drug, and pre-loaded doxycycline released an additional 28% over the following 6 days. For LMW ISIs, the plateau ranged from 86-95% for 30% PLGA and from 63-74% in 40% PLGA. ISIs containing 40% LMW PLGA were tested with pre-loaded doxycycline, and after an initial 63% burst, release continued up to 87% by day 7.

Discussion

PBAE additives act as both porogens and drug delivery vehicles within the solid. PLGA ISI matrix. As porogens, the 1-day mass loss of HMW-H and HMW-H/AH scaffolds indicated complete degradation of H6, which has an expected degradation time of 4-8 hours (Hawkins A M, Milbrandt T A, Puleo D A, Hilt J Z. Synthesis and analysis of degradation, mechanical and toxicity properties of poly ($\beta$-amino ester) degradable hydrogels. Acta Biomater 2011; 7:1956-64), while both HMW-AH and LMW-AH scaffolds exhibited a gradual mass loss through 10 days, which is twice the 5 day in vitro degradation time of AH6 PBAEs (Hawkins A M, Tolbert M E, Newton B, Milbrandt T A, Puleo D A, Hilt J Z. Tuning biodegradable hydrogel properties via synthesis procedure. Polymer 2013; 54:4422-6). The difference is probably due to the PLGA matrix both limiting access of water to the embedded PBAE microparticles and physically preventing them from swelling, thus slowing degradation (Clark A, Milbrandt T A, Hilt J Z, Puleo D A. Mechanical properties and dual drug delivery application of poly(lactic-co-glycolic acid) scaffolds fabricated with a poly($\beta$-amino ester) porogen. Acta Biomater 2014; 10:2125-32; Hawkins A M, Milbrandt T A, Puleo D A, Hilt J Z. Composite hydrogel scaffolds with controlled pore opening via biodegradable hydrogel porogen degradation. J Biomed Mater Res A 2014; 102:400-12). There is evidence that PBAE swelling is restricted by comparing the microCT cutplanes and implant volumes between groups, in which HMW-H, which contains the most hydrophilic PBAE, swelled more gradually and to a smaller degree than HMW-AH and HMW-H/AH formulations. Theoretically, H6 should achieve greater maximum swelling than AH6, and the maximum swelling point should occur at 4 and 36 hours, respectively (Spencer D. Oswald physical and engineering sciences second place: multiple macromer hydrogels for multiphase drug release. Kaleidoscope 2014; 11:20). HMW-H scaffolds likely delayed degradation of the PBAE as well, however, the daily sampling frequency would not detect a difference unless the degradation period of H6, which typically degrades in 4-8 hours (Hawkins A M, Milbrandt T A, Puleo D A, Hilt J Z. Synthesis and analysis of degradation, mechanical and toxicity properties of poly ($\beta$-amino ester) degradable hydrogels. Acta Biomater 2011; 7:1956-64), was prolonged beyond 24 hours. The failure of HMW-Controls to swell beyond their initial mass suggests that the loss of NMP during precipitation exceeded the water uptake of the scaffolds. Conversely, LMW-Controls were capable of entrapping water in the core of the scaffolds due to their less hydrophobic nature, and the rapid decrease in wet mass after day 3 was caused by the fragile PLGA skin rupturing, allowing the entrapped buffer to leak out. Interestingly, all HMW scaffolds containing PBAE microparticles swelled up to 250% of their original mass over a period of 30 days, while comparable LMW scaffolds swelled to a maximum of 150%. Again, LMW scaffolds were prone to rupture, which would allow water to escape, while the HMW scaffolds remained structurally intact as they swelled and therefore maintained a larger water capacity. Prior research on similar systems containing porogens such as sucrose or sodium chloride did not show such a dramatic mass changes (Krebs M D, Sutter K A, Lin A S P, Guldberg R E, Alsberg E. Injectable poly(lactic-co-glycolic) acid scaffolds with in situ pore formation for tissue engineering. Acta Biomater 2009; 5:2847-59), which suggests that the swelling behavior of PBAE hydrogel particles has a more profound effect on water uptake and retention than traditional porogens.

PBAE microparticles also influence macro- and microstructural changes of ISIs as they degrade. HMW-Controls possessed surface-adjacent smaller pores and centrally-located macropores, which is typical of these implants because PLGA at the surface tends to precipitate rapidly, while the interior precipitates more gradually, allowing voids to coalesce (Astaneh R, Erfan M, Moghimi H, Mobedi H. Changes in morphology of in situ forming PLGA implant prepared by different polymer molecular weight and its effect on release behavior. J Pharm Sci 2009; 98:135-45). PBAE microparticles caused the ISIs to adopt a porous network microarchitecture with no difference between surface or central pore sizes, because the homogeneous distribution of hydrogel microparticles acted as a template for uniform PLGA precipitation. This hypothesis is supported by the rapid swelling and increase in accessible volume observed in all PBAE-containing ISIs. The lack of collapse in HMW-AH, -H, or -H/AH implants implies that these homogeneously distributed hydrogel particles also played a role in structurally stabilizing the scaffolds. In HMW-Controls, the largest pores collapsed, whereas PBAE-containing scaffolds, with their uniform microarchitectures, were able to distribute stresses throughout the PLGA matrix and avoid collapse. It has been previously demonstrated that varying the size and distribution of pores can dramatically alter mechanical properties of materials (Li H, Oppenheimer S M, Stupp S I, Dunand D C, Brinson L C. Effects of pore morphology and bone ingrowth on mechanical properties of microporous titanium as an orthopaedic implant material. Mater Trans 2004; 45:1124-31; Yu H, Matthew H W, Wooley P H, Yang S-Y. Effect of porosity and pore size on microstructures and mechanical properties of poly-ε-caprolactone-hydroxyapatite composites. J Biomed Mater Res B Appl Biomater 2008; 866:541-7). The lattice-like PLGA network of PBAE-containing implants may also help explain the sustained mechanical resilience observed for HMW-AH implants even after the degradation period of the PBAE had passed. The increased porosity and accessible surface area of PBAE-containing ISIs offers many advantages when considering PLGA ISIs as potential scaffolds rather than simply drug delivery devices. In pre-formed PLGA scaffolds, larger accessible volume and surface area provide more opportunity for tissue ingrowth, and it is anticipated that PLGA ISIs will behave similarly in future cell culture or in vivo testing.

A persistent issue with antibiotic-releasing implants in periodontal applications is that the implant is not secure inside the periodontal pocket, which can lead to small pieces being dislodged as the implant moves within the space (Anderson H H. Treatment of chronic periodontitis: a site-specific fiber placement technique. Pract Periodontics Aesthet Dent 1996; 8:565-70). Here, push-out forces were used to measure the interfacial strength between the implant surface and a simulated tissue pocket. The opposing trends observed in push-out force for HMW-Control compared to HMW-AH samples indicate that swelling of AH hydrogels can improve space-filling and pocket retention of implants. Even at the initial 3-day measurement, HMW-AH samples had significantly higher interfacial strength than controls, and this difference became even more pronounced as the incubation period increased. Although HMW PLGA does swell to a small degree as it degrades, this behavior is offset by the shrinkage of the implant during the precipitation phase, and the net result is that the interfacial strength remains negligible. On the other hand, AH hydrogels were observed to swell beyond 200% of their initial mass within 2 days in PBS (data not shown), and although this effect is probably muted due to the physical constraint within the PLGA matrix, there is enough of an effect to provide 4 to 10-fold higher interfacial strength than controls. Preliminary studies also showed no measurable adhesion between the gelatin surface and the implants (data not shown), so any differences in interfacial strength should be solely a result of the superior space-filling due to swelling of HMW-AH implants. LMW-AH scaffolds exhibited a similar benefit compared to LMW-Controls, although this difference was less pronounced due to the natural swelling behavior of LMW-Controls, which increased interfacial strength, and the rapid degradation of material, which caused both LMW-Controls and LMW-AH to decrease in strength over the 15 day period. A scaffold that expands to fill its injection site as it solidifies is less likely to cause irritation due to movement within the pocket. Furthermore, more contact area between the implant and the tissue means that the released drug has a shorter path to enter the gingival tissue, and it has a smaller likelihood of being washed away due to exchange in the crevicular fluid. Little information is available on the magnitude of stresses experienced within gingival soft tissue, but the periodontal ligament is the soft tissue responsible for transmitting chewing force between the tooth and the underlying alveolar bone (Andersen K L, Pedersen E H, Melsen B. Material parameters and stress profiles within the periodontal ligament. Am J Orthod Dentofacial Orthop 1991; 99:427-40; Beertsen W, McCulloch C A G, Sodek J. The periodontal ligament: a unique, multifunctional connective tissue. Periodontol 2000 1997; 13:20-40). Measurements of stress in oral mucosal tissues under typical bite forces of denture wearers suggested that these tissues experience compressive stresses ranging from 5 to 40 kPa during chewing (Sawada A, Wakabayashi N, Ona M, Suzuki T. Viscoelasticity of human oral mucosa: implications for masticatory biomechanics. J Dent Res 2011; 90:590-5). According to these values, HMW-AH ISIs have initial interfacial strengths within that range, and within 6 days the interfacial strength exceeds the stress generated by a soft bite. HMW-Controls at every time point possessed interfacial strengths 1-2 orders of magnitude lower. These data suggest that patients receiving HMW-AH ISIs may be able to chew food shortly after receiving treatment without danger of loosening the implant, while controls, which approximate clinically available treatments, are more easily loosened and dislodged. This swelling-based, space-filling approach is an alternative to other avenues that seek to reduce detachment by improving the adhesion between the polymer surface and surrounding tissue. In a separate study using a more adhesive components, increased bioadhesion was observed in the first several hours following injection into a simulated pocket (Do M P, Neut C, Delcourt E, Seixas Certo T, Siepmann J, Siepmann F. In situ forming implants for periodontitis treatment with improved adhesive properties. Eur J Pharm Biopharm 2014:[Epub ahead of print]), whereas the present PBAE-containing ISIs were demonstrated to improve pocket retention through a 15-day period. An interesting approach for future studies may be to incorporate both bioadhesive and swelling additives in order to provide acute attachment followed by prolonged space-filling.

Although these periodontal ISIs are not designed as load-bearing structures, they are subject to stresses, primarily due to chewing, which typically occurs at frequencies between 0.1 and 1 Hz in humans (Tanaka E, Yamano E, Dalla-Bona D A, Watanabe M, Inubushi T, Shirakura M, et al. Dynamic compressive properties of the mandibular condylar cartilage. J Dent Res 2006; 85:571-5). The gelatin molds used in push-out studies had similar compressive modulus compared to gingival tissues in order to simulate a periodontal pocket (Goktas S, Dmytryk J J, McFetridge P S. Biomechanical behavior of oral soft tissues. J Periodontol 2011; 82:1178-86). It has been proposed that less stiff implants may reduce irritation due to the presence of material within the periodontal pocket (Qin Y, Yuan M, Li L, Li W, Xue J. Formulation and evaluation of in situ forming PLA implant containing tinidazole for the treatment of periodontitis. J Biomed Mater Res B Appl Biomater 2012; 100B:2197-202). PLGA deformed plastically and became stiffer under compression, even at low strains and only 30 compression cycles, while the modulus of HMW-AH samples remained unchanged, indicating that PBAE additives preserve elasticity. In the commercially available Atridox® system, a dressing or adhesive is used to keep the implant in place, but there is also the concern that repeated compression cycles can cause the implants to break apart, allowing pieces of material to cause local irritation or escape the periodontal pocket (Drisko C H. The use of locally-delivered doxycycline in the treatment of periodontitis. Clinical results*. J Clin Periodontol 1998; 25:947-52; Karimbux N. Clinical cases in periodontics. Chichester, West Sussex, UK: Wiley-Blackwell; 2012). Therefore, flossing and brushing are discouraged for up to a week following implantation, and patients are told to expect small pieces of material to break off (Drisko C H. The use of locally-delivered doxycycline in the treatment of periodontitis. Clinical results*. J Clin Periodontol 1998; 25:947-52). Although neither control nor PBAE-containing ISIs broke apart during the timeframe or compression cycles observed, the 30-cycle modulus of HMW-Controls was reduced dramatically between 9 and 15 days, and this difference would likely become more pronounced as time or compression cycles increased. HMW-AH samples were less stiff and retained their modulus throughout cyclic compression, which suggests they are more suitable to withstand the dynamic mechanical environment of the periodontal tissue. HMW-Controls and LMW-Controls were more resilient during the initial compression cycle, yet they were consistently less resilient than corresponding AH-containing implants after 30 cycles, indicating that the PBAE hydrogel component helps preserve resilience. The lack of change for both modulus and resilience after cyclic loading is promising for the development of more mechanically suitable implants for the periodontal pocket. Dynamic mechanical analysis is required to assess viscoelastic properties for full lifespan of the implant, but this short-term cyclic compression data suggests that the addition of only 10% hydrogel particles can greatly improve the durability of these implants. As mentioned previously, the addition of PBAE microparticles led to a lattice-like PLGA microarchitecture, which should theoretically provide more resilience than the heterogeneous structure of the controls because there are no macropores, which appear to be the source of collapse in controls. Oral soft tissues have compressive moduli ranging from 0.2 to 8 MP, and typical dental materials used to fill these soft tissues after extractions or other procedures have moduli on the order of 1-20 MPa, which are both similar to the compressive properties of ISIs developed here.

Simvastatin release kinetics from both HMW and LMW ISIs were highly dependent on PBAE microparticle content. The larger burst in controls can be attributed to simvastatin dissolved in the NMP phase being rapidly lost during solvent exchange, which has been previously reported (Fisher P D, Palomino P, Milbrandt T A, Hilt J Z, Puleo D A. Improved small molecule drug release from in situ forming poly (lactic-co-glycolic acid) scaffolds incorporating poly(beta-amino ester) and hydroxyapatite microparticles. J Biomater Sci Polym Ed 2014; 25:1174-93). Because these PBAEs swell in many organic solvents, such as NMP, acetone, and ethanol, PBAE microparticles become swollen with NMP and simvastatin during the mixing phase prior to injection. Simvastatin, which is freely soluble in NMP, is preferentially taken up by PBAEs, which act as NMP sponges, while NMP-insoluble drugs such as doxycycline remain in the PLGA phase outside the swollen particles (data not shown). These swollen microparticles act as an additional diffusive barrier to reduce initial burst of simvastatin, and once the initial hardening of the scaffold surface has occurred, simvastatin release is governed by both diffusion and PBAE degradation. The degradation profile of AH6 microparticles is reflected in the accelerated release rate from AH- and H/AH-containing scaffolds through day 13. The release profile for HMW-H/AH ISIs closely approximates the average of the HMW-H and HMW-AH curves, which suggests that the two hydrogels contribute independently to simvastatin release kinetics, and the results of their contributions are additive. Simvastatin release kinetics were more strongly affected by PBAE microparticle content in 30% LMW PLGA scaffolds than in 40% LMW PLGA scaffolds, and this difference is attributable to multiple factors. First, the higher PLGA content formulation is more viscous, which allows more rapid formation of a protective "skin" that slows solvent exchange and thus burst release. Second, 40% LMW ISIs contain more PLGA for equivalent injected masses when compared to 30% LMW ISIs, which provides more polymer volume to entrap simvastatin, further limiting burst. Interestingly, AH6 degradation did not appear to accelerate simvastatin release in LMW scaffolds as dramatically as it did in HMW scaffolds for the first 10 days. This may be due to the faster degradation time and relatively lower hydrophobicity of LMW PLGA, which allows faster simvastatin release from the PLGA phase and masks the contribution of AH6-mediated release.

Release kinetics of freely-mixed doxycycline from HMW and LMW ISIs were unaffected by the addition of PBAE microparticles, however pre-loading doxycycline into AH6 microparticles provided a measure of control. The lack of additional doxycycline release after the initial burst in freely mixed cases is probably due to the entrapment of remaining drug in the PLGA phase, and because doxycycline is substantially more hydrophilic than simvastatin, it has low mobility through the hydrophobic PLGA matrix. This plateau effect is undesirable for antibiotic delivery, because bacteria surviving the initial burst will be free to re-colonize. By pre-loading doxycycline into AH6 PBAE microparticles, the initial burst was followed by continuous release of remaining drug through 1 week, which is consistent with systemic doxycycline regimens of 1 week following scaling and root planing.

Conclusions

PLGA ISIs formulated with PBAE microparticle additives provide multiple advantages over existing periodontal ISIs. These composite ISIs are more resilient and are retained more firmly in simulated gingival tissue than PLGA alone, so there will be a lower risk of the implant deforming, loosening, and premature fragmentation, which is a concern with existing systems. Additionally, PBAE microparticles offer a secondary means of controlling drug release kinetics, and multiple drugs with independent release profiles can be delivered, instead of the single-drug systems that are currently available. Future studies will focus on the potential of these PBAE-containing ISIs to act as scaffolds for tissue regeneration, because the high porosity and open pore network is suitable for tissue ingrowth.

The foregoing descriptions of various embodiments provide illustration of the inventive concepts. The descriptions are not intended to be exhaustive or to limit the disclosed invention to the precise form disclosed. Modifications or variations are also possible in light of the above teachings. The embodiments described above were chosen to provide the best application to thereby enable one of ordinary skill in the art to utilize the inventions in various embodiments and with various modifications as are suited to the particular use contemplated. All such modifications and variations are within the scope of the invention. All publications, patents and patent applications referenced herein are to be each individually considered to be incorporated by reference in their entirety.

What is claimed:

1. An injectable system for assisting in osseous tissue repair, the system comprising a degradable matrix and composite microparticles in a solvent, the degradable matrix being selected from the group consisting of PLGA, poly (lactic acid) and poly(ε-caprolactone) and the solvent being selected from the group consisting of N-methyl-2-pyrrolidone, dimethyl sulfoxide, ethyl acetate, ethyl benzoate, and triacetin, wherein the composite microparticles comprise cross-linked poly(β-amino ester) (PBAE) microparticles embedded with a ceramic, the ceramic being embedded by dry grinding and the ceramic being selected from the group consisting of hydroxyapatite (HA), brushite, calcium polyphosphate, β-tricalcium phosphate, and monetite, and further wherein the system solidifies in situ.

2. The injectable system of claim 1, wherein the degradable matrix is PLGA, with a selected L:G ratio, molecular weight, and endcap.

3. The injectable system of claim 2, wherein the PLGA has a L:G ratio of between 50:50 and 95:5, a molecular weight between 5 and 300 kDa and an endcap of carboxylate or ester-crosslinked hydrocarbon.

4. The injectable system of claim 1, wherein between 15 and 45 w/w % is the degradable matrix between 15 and 45 w/w % (+/−10%) is the ceramic and between 3-25 w/w % (+/−10%) is the PBAE.

5. The injectable system of claim 1, wherein the system comprises 19.5 w/w % degradable matrix, 45.5 w/w % solvent, 30 w/w % ceramic and 5 w/w % drug-loaded PBAE.

6. The injectable system of claim 1, wherein the system comprises 18 w/w % degradable matrix, 42 w/w % solvent, 30 w/w % ceramic and 10 w/w % drug-loaded PBAE.

7. The injectable system of claim 1, wherein the PBAE is pre-loaded with a therapeutic agent, wherein the therapeutic agent is selected from the group consisting of coldronate, alendronate, etidronate, zoledronate, simvastatin, lovastatin, rosuvastatin, SVAK-12, bone morphogenetic proteins, parathyroid hormone (1-34), metronidazole, doxycycline, vancomycin, gentamycin, ciprofloxacin, ketoprofen, celecoxib, diclofenac, meloxicam or mixtures thereof.

8. A method of preparing the in situ injectable system of claim 1, comprising mixing the degradable matrix, microparticles and solvent.

9. The method of claim 8, wherein the microparticles are preloaded with at least one pharmaceutical agent.

10. The method of claim 8, further comprising cross-linking the degradable matrix.

11. The method of claim 9, wherein the microparticle are mixed with the degradable matrix prior to cross-linking.

12. A method of treating osseous tissue, comprising administering by injection the system of claim 1.

* * * * *